(12) United States Patent
Kufer et al.

(10) Patent No.: US 9,505,849 B2
(45) Date of Patent: Nov. 29, 2016

(54) ANTIBODY CONSTRUCTS FOR INFLUENZA M2 AND CD3

(71) Applicants: AMGEN RESEARCH (MUNICH) GMBH, Munich (DE); VIB VZW, Ghent (BE); Universiteit Gent, Ghent (BE)

(72) Inventors: Peter Kufer, Munich (DE); Tobias Raum, Munich (DE); Markus Muenz, Munich (DE); Jochen Pendzialek, Munich (DE); Walter Fiers, Destelbergen (BE); Xavier Saelens, Ypres (BE); Kenny Roose, Ettelgem (BE)

(73) Assignees: AMGEN RESEARCH (MUNICH) GMBH, Munich (DE); VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 14/774,293

(22) PCT Filed: Mar. 17, 2014

(86) PCT No.: PCT/EP2014/055311
§ 371 (c)(1),
(2) Date: Jan. 29, 2016

(87) PCT Pub. No.: WO2014/140368
PCT Pub. Date: Sep. 18, 2014

(65) Prior Publication Data
US 2016/0039948 A1 Feb. 11, 2016

Related U.S. Application Data

(60) Provisional application No. 61/792,730, filed on Mar. 15, 2013.

(51) Int. Cl.
| | | |
|---|---|---|
| *A61K 39/42* | (2006.01) | |
| *A61K 45/06* | (2006.01) | |
| *C07K 16/46* | (2006.01) | |
| *C07K 16/10* | (2006.01) | |
| *C07K 16/28* | (2006.01) | |
| *A61K 39/00* | (2006.01) | |

(52) U.S. Cl.
CPC ............ *C07K 16/468* (2013.01); *A61K 39/42* (2013.01); *A61K 45/06* (2013.01); *C07K 16/1018* (2013.01); *C07K 16/2809* (2013.01); *A61K 2039/505* (2013.01); *C07K 2317/14* (2013.01); *C07K 2317/24* (2013.01); *C07K 2317/31* (2013.01); *C07K 2317/622* (2013.01); *C07K 2317/73* (2013.01); *C07K 2317/92* (2013.01)

(58) Field of Classification Search
None
See application file for complete search history.

(56) References Cited

FOREIGN PATENT DOCUMENTS

WO WO-2012/125614 A1 9/2012

OTHER PUBLICATIONS

Fernandez-Sesma et al., A bispecific antibody recognizing influenza A virus M2 protein redirects effector cells to inhibit virus replication in vitro. *J. Virol.* 7(7): 4800-4 (1996).
Gabbard et al., A humanized anti-M2 scFv shows protective in vitro activity against influenza. *Protein Engin. Design Select.* 22(3): 189-98 (2009).
Hughey et al., Effects of antibody to the influenza A virus M2 protein on M2 surface expression and virus assembly. *Virology* 212: 411-21 (1995).
Liu et al., Monoclonal antibodies recognizing EVETPIRN epitope of influenza A virus M2 protein could protect mice from lethal influenza A virus challenge. *Immunol. Lett.* 93: 131-6 (2004).
Moran et al., Inhibition of multicycle influenza virus replication by hybrid antibody-directed cytotoxic T lymphocyte lysis. *J. Immunol.* 146(1): 321-6 (1991).
Treanor et al., Passively transferred monoclonal antibody to the M2 protein inhibits influenza A virus replication in mice. *J. Virol.* 64(3): 1375-7 (1990).
Wang et al., Therapeutic potential of a fully human monoclonal antibody against influenza A virus M2 protein. *Antiviral Res.* 80: 168-77 (2008).
International Search Report and Written Opinion of the International Searching Authority issued in connection with International Application No. PCT/EP2014/055311, dated Jul. 31, 2014.

*Primary Examiner* — Benjamin P Blumel
(74) *Attorney, Agent, or Firm* — Marshall, Gerstein & Borun LLP

(57) ABSTRACT

The present invention relates to an antibody construct comprising a first human binding domain specific for the extracellular part of the influenza envelope protein M2 (M2e) and a second domain specific for CD3. Moreover, the invention provides a nucleic acid molecule encoding the antibody construct, a vector comprising said nucleic acid molecule and a host cell transformed or transfected with said nucleic acid molecule or vector. Furthermore, the invention provides a process for the production of the antibody construct of the invention, a pharmaceutical composition comprising said antibody construct, a medical use/method of treatment relating to said antibody construct, and a kit comprising said antibody construct.

20 Claims, 5 Drawing Sheets

| Molecule name | EC$_{50}$ [pg/ml] |
|---|---|
| murM2e-hBiTE | 3111 |
| humM2e-hBiTE-1 | 257 |
| humM2e-hBiTE-2 | 1746 |
| humM2e-hBiTE-3 | 510 |
| humM2e-hBiTE-4 | 408 |
| humM2e-hBiTE-5 | 198 |
| humM2e-hBiTE-6 | 2280 |
| humM2e-hBiTE-7 | 212 |
| humM2e-hBiTE-8 | 221 |
| humM2e-hBiTE-9 | 320 |

Figure 5A

Survival of IVA BiTE treated mice infected with a Tamiflu resistant strain H5N1 H274Y

Figure 5 B

Body weight of IVA BiTE treated mice infected with a Tamiflu resistant strain H5N1 H274Y

ANTIBODY CONSTRUCTS FOR INFLUENZA M2 AND CD3

FIELD OF THE INVENTION

The present invention relates to an antibody construct comprising a first human binding domain specific for the extracellular part of the influenza envelope protein M2 and a second domain specific for CD3. Moreover, the invention provides a nucleic acid molecule encoding the antibody construct, a vector comprising said nucleic acid molecule and a host cell transformed or transfected with said nucleic acid molecule or vector. Furthermore, the invention provides a process for the production of the antibody construct of the invention, a pharmaceutical composition comprising said antibody construct, a medical use/method of treatment relating to said antibody construct, and a kit comprising said antibody construct.

BACKGROUND OF THE INVENTION

Influenza is probably the most wide-spread virus disease in the human population worldwide. Epidemics, which occur annually in most locations, cause 3-5 million severely ill patients per year worldwide. Of these, 250,000 to 500,000 have a fatal outcome. Influenza disease is also the major cause of lost work- and schooldays, which means an economic loss estimated at 87 billion dollars for the USA alone. Both influenza A and the very distantly related influenza B strains cause severe epidemics, the latter at a frequency of about 33%.

Pandemics, which emerge on average once per decade, are even deadlier, because no lingering immune memory is left in the human population. The "Spanish Flu" which spread at the end of World War I, caused an estimated 50 million victims. Also the more recent "Bird flu" was very deadly.

Hemagglutinin (HA) is the most prevalent protein on the viral capsid, and its function is to anchor the virus on its target cells. Serological evidence first suggested that epidemics arose by a few mutations in the HA gene of a circulating strain leading to partial or complete resistance to humoral immunity in the host. New pandemic strains, on the other hand, arise by reassortment, whereby a totally new HA gene (e.g. H1, H2, H3, H5, . . . ) is incorporated in a human influenza strain. These mutations and reassortments may occur in humans or, more likely, in transmissible carrier-animals, such as chickens and swine. The source of these new HA genes is usually migratory water-fowl. Their northern habitat is a well-known as a reservoir of various influenza stains. As a result, the origin of new human pandemics has often been traced to such migratory bird routes. The gradual mutations leading to new epidemics are referred to as "drift", while the appearance of a new HA gene in a human influenza strain is known as a "shift". Sequencing of HA genes of appropriate influenza strains confirmed the molecular explanation of the "drift" and "shift" phenomena.

Around 1950, the first influenza vaccines became available. These contain HA as their main antigenic component, either as inactivated whole virus, or dissociated viral capsid proteins or purified subunits. Also, attenuated viral strains were introduced. The result was and still is that these vaccines are highly virus strain specific. Each year in February, the WHO guesses which strains will likely be prevalent that year, and advises a vaccine composition consisting of two influenza A strains and one (recently even two) influenza B strains to the vaccine manufacturers. These classical vaccines, based on induction of anti-HA antibodies, protect very efficaciously provided the guess was right and the HA in the vaccine matches closely the HA in the epidemic viral strain. Because of the uncertainty of strain selection and the nearly annual change of prevalent virus challenge, the vaccination coverage is usually not very high.

The molecular nature of the HA-gene in a newly emerging pandemic strain cannot be predicted. As soon as a new virus appears in humans, its HA-gene is characterized, and a matching vaccine is prepared, tested and distributed. However, as the time to prepare a matching vaccine is on average 6 months, the influenza pandemic may already have caused considerable damage in the human population before it is possible to contain it.

The Influenza M2 protein is a proton-selective ion-channel protein, integral in the viral envelope of the influenza A virus. The channel itself is a homotetramer (i.e. it consists of four identical M2 units), where the units are helices stabilized by two disulfide bonds. It is activated by low pH. The M2 protein is also an integral membrane protein expressed on the surface of infected cells.

The M2 protein has an important role in the infectious cycle of the influenza A virus. It is located in the viral envelope. It allows the entry of protons into the viral particle (virion) from inside the endosome, thus lowering the pH inside of the virus. This causes dissociation of the viral matrix protein M1 from the ribonucleoprotein RNP; this dissociates the nucleic acid genome and the membrane, so when fusion occurs, the nucleic acid is released into the cytoplasm and not stick to the membrane, where it cannot carry out its function.

The function of the M2 channel can be inhibited by the antiviral drugs amantadine and rimantadine, which then blocks the virus from taking over the host cell. The molecule of the drug binds to the transmembrane region, sterically blocking the channel. This stops the protons from entering the virion, which then does not disintegrate. However, when one of five amino acids in the transmembrane region gets suitably substituted, the virus gains resistance to the existing M2 inhibitors. As these mutations are relatively frequent, presence of the selection factors (e.g. using amantadine for treatment of sick poultry) can lead to emergence of a resistant strain.

The amino acid sequence of the M2 protein can vary between different virus strains. One example (M2 Influenza A/Puerto Rico 8/34) is represented by SEQ ID NO: 89.

Antibodies against the M2 protein are known in the art and commercially available. They are applicable e.g. in Western Blot, immunohistochemistry, ELISA or enzyme immunoassay. These antibodies comprise polyclonal and monoclonal antibodies generated in animal hosts.

Common treatments for an influenza infection include a range of medications and therapies. They may either directly target the virus itself or may just offer relief to symptoms. The two main classes of antiviral drugs used against influenza are neuraminidase inhibitors (such as zanamivir and oseltamivir) and inhibitors of the viral M2 protein, such as amantadine and rimandatine. These drugs can reduce the severity of symptoms if taken soon after infection and can also be taken to decrease the risk of infection. Influenza viruses can show resistance to anti-viral drugs, which can result from over-use of these drugs.

In the case of neuraminidase inhibitors, different strains of influenza viruses have differing degrees of resistance against these antivirals, and it is impossible to predict what degree of resistance a future pandemic strain might have.

The M2 inhibitors are sometimes effective against influenza A if given early in the infection. In the case of amantadine, the treatment may lead to rapid production of resistant viruses, and over-use of this drug has probably contributed to the spread of resistance. Measured resistance to amantadine and rimantadine in American isolates of H3N2 has increased to 91% in 2005.

There remains hence a need for further options for the treatment of influenza. Accordingly, there is provided herewith means and methods for the solution of this problem in the form of an antibody construct comprising a first binding domain specific for the extracellular part of the influenza M2 protein and a second binding domain specific for CD3.

SUMMARY OF THE INVENTION

Thus, in a first aspect of the invention, an antibody construct is provided comprising
- (a) a first human binding domain specific for the extracellular part of the influenza envelope protein M2 (M2e), characterized by a CDR-H1 as depicted in SEQ ID NO: 1, a CDR-H2 as depicted in SEQ ID NO: 2, a CDR-H3 as depicted in SEQ ID NO: 3, a CDR-L1 as depicted in SEQ ID NO: 4, a CDR-L2 as depicted in SEQ ID NO: 5, and a CDR-L3 as depicted in SEQ ID NO: 6; and
- (b) a second domain specific for CD3.

It has been surprisingly found that the antibody constructs of the present invention which have a human binding domain specific for M2e have several advantages compared with antibody constructs using the parental murine anti-M2e binder. They not only show significantly higher affinities to M2e (see Example 7), but also a higher cytotoxic activity (see Example 8). Given the fact that "naturally" obtained unmodified binders are considered to be optimized by nature using the complete machinery of the antibody repertoire with respect to their binding capacity and biological activity, it is unexpected and surprising that modifications in the amino acid sequence including the CDR sequences result in binding domains with increased M2e binding and cytotoxic activity. In contrast, the person skilled in the art would have expected that by creating a human binding domain, suitable for medical use in humans and not eliciting immunogenicity, starting from the parental binder the characteristics of the naturally optimized binder would significantly degenerate compared to the parental binder.

In one embodiment of the antibody construct of the invention, the first binding domain comprises a VH region selected from the group consisting of VH regions as depicted in SEQ ID NO: 8, SEQ ID NO: 16, SEQ ID NO: 24, SEQ ID NO: 32, SEQ ID NO: 40, SEQ ID NO: 48, SEQ ID NO: 56, SEQ ID NO: 64, and SEQ ID NO: 72.

In another embodiment of the antibody construct of the invention, the first binding domain comprises a VL region selected from the group consisting of VL regions as depicted in SEQ ID NO: 10, SEQ ID NO: 18, SEQ ID NO: 26, SEQ ID NO: 34, SEQ ID NO: 42, SEQ ID NO: 50, SEQ ID NO: 58, SEQ ID NO: 66, and SEQ ID NO: 74.

In a further embodiment of the antibody construct of the invention, the first binding domain comprises a VH region and a VL region selected from the group consisting of pairs of a VH region and a VL region as depicted in SEQ ID NO: 8+10, SEQ ID NO: 16+18, SEQ ID NO: 24+26, SEQ ID NO: 32+34, SEQ ID NO: 40+42, SEQ ID NO: 48+50, SEQ ID NO: 56+58, SEQ ID NO: 64+66 and SEQ ID NO: 72+74.

According to another embodiment of the invention, the antibody construct is in a format selected from the group consisting of $(scFv)_2$, (single domain $mAb)_2$, scFv-single domain mAb, diabodies and oligomers of any of the foregoing.

In a preferred embodiment, the first binding domain comprises an amino acid sequence selected from the group consisting of SEQ ID NO: 12, SEQ ID NO: 20, SEQ ID NO: 28, SEQ ID NO: 36, SEQ ID NO: 44, SEQ ID NO: 52, SEQ ID NO: 60, SEQ ID NO: 68, and SEQ ID NO: 76.

In another embodiment of the antibody construct of the invention, the second binding domain is capable of binding to human and *Callithrix jacchus*, *Saguinus Oedipus* or *Saimiri sciureus* CD3 epsilon.

In a further preferred embodiment, the antibody construct of the invention has an amino acid sequence selected from the group consisting of SEQ ID NO: 14, SEQ ID NO: 22, SEQ ID NO: 30, SEQ ID NO: 38, SEQ ID NO: 46, SEQ ID NO: 54, SEQ ID NO: 62, SEQ ID NO: 70, and SEQ ID NO: 78.

The invention further provides a nucleic acid molecule having a sequence which encodes an antibody construct of the invention.

Furthermore, the invention provides a vector comprising a nucleic acid molecule of the invention.

Moreover, the invention provides a host cell transformed or transfected with the nucleic acid molecule or with the vector of the invention.

In a further embodiment, the invention provides a process for the production of an antibody construct of the invention, said process comprising culturing a host cell of the invention under conditions allowing the expression of the antibody construct of the invention and recovering the produced antibody construct from the culture.

Moreover, the invention provides a pharmaceutical composition comprising an antibody construct of the invention or produced according to the process of the invention. In one embodiment, the invention provides a pharmaceutical composition comprising an antibody construct of the invention, or produced according to the process of the invention, and a reactive oxygen scavenger for the amelioration or treatment of an influenza A virus infection.

In one embodiment, the invention provides the antibody construct of the invention or produced according to the process of the invention for use in the treatment, amelioration or future prevention of an infection with influenza A virus.

The invention also provides a method for the treatment, amelioration or future prevention of an infection with influenza A virus, comprising the step of administering to a subject in need thereof the antibody construct of the invention or produced according to the process of the invention. In a preferred embodiment, this method further comprises the step of administering a reactive oxygen scavenger.

In a further embodiment, the invention provides a kit comprising an antibody construct of the invention, or produced according to the process of the invention, a vector of the invention, and/or a host cell of the invention.

Figure 1:
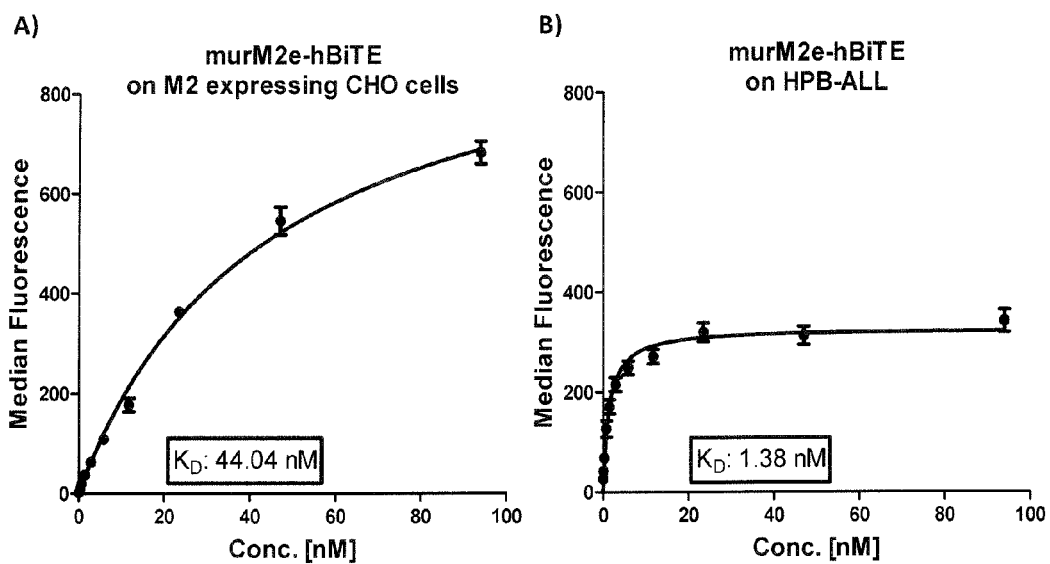
FIG. 1:
Affinity measurements of the murM2e-hBiTE on M2 expressing CHO cells (A) and human CD3, expressed by HPB-ALL cells (B). The median values of 3 measurements+/−SEM are shown.

Cytotoxic activities of murine and human-like anti-M2e× anti-CD3 bispecific (scFv)$_2$ constructs. The humM2e-hBiTEs 1-9 all show higher cytotoxic activities compared to the murM2e-hBiTE. The control constructs 1 and 2 do not show cytotoxic activity. In the table the $EC_{50}$ values of all active anti-M2e×anti-CD3 bispecific scFv constructs shown in the diagram are listed.

FIG. 4:

Survival of Influenza A infected mice treated with a daily i.v. injection of 10 µg bispecific scFv constructs or 15 µg parental monoclonal antibody (equimolar) from days 1 through 6 after virus challenge. All mice treated with humM2e-mBiTE survive until the end of the experiment, compared to 30% survival of mice treated with murM2e-mBiTE.

FIG. 5:

A) The survival of the mice after virus challenge. All treatments were administered daily from day 1 after challenge until day 6 after challenge. hM2e-mBiTE and hM2e-hBiTE were administered intravenously at a dose of 10 µg per mouse per day (in a total volume of 100 µL).

B) The morbidity curves show the body weight of all groups during the 14 days following the challenge. The body weight is expressed as the relative body weight compared to the body weight on the day of the challenge (day 0).

DETAILED DESCRIPTION OF THE INVENTION

Definitions

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The definition of the term "antibody" includes embodiments such as monoclonal, chimeric, single chain, humanized and human antibodies, as well as antibody fragments, like, inter alia, Fab fragments. Antibody fragments or derivatives further comprise F(ab')$_2$, Fv, scFv fragments or single domain antibodies such as domain antibodies or nanobodies, single variable domain antibodies or immunoglobulin single variable domain comprising merely one variable domain, which might be VHH, VH or VL, that specifically bind an antigen or epitope independently of other V regions or domains; see, for example, Harlow and Lane (1988) and (1999), loc. cit.; Kontermann and Dübel, Antibody Engineering, Springer, 2nd ed. 2010 and Little, Recombinant Antibodies for Immunotherapy, Cambridge University Press 2009. Such immunoglobulin single variable domain encompasses not only an isolated antibody single variable domain polypeptide, but also larger polypeptides that comprise one or more monomers of an antibody single variable domain polypeptide sequence.

In line with this definition all above described embodiments of the term antibody can be subsumed under the term "antibody construct". Said term also includes diabodies or Dual-Affinity Re-Targeting (DART) antibodies. Further envisaged are single chain diabodies, tandem diabodies (Tandab's), "minibodies" exemplified by a structure which is as follows: (VH-VL-CH3)$_2$, (scFv-CH3)$_2$ or (scFv-CH3-scFv)$_2$, "Fc DART" antibodies and "IgG DART" antibodies, and multibodies such as triabodies. Immunoglobulin single variable domains encompass not only an isolated antibody single variable domain polypeptide, but also larger polypeptides that comprise one or more monomers of an antibody single variable domain polypeptide sequence.

Various procedures are known in the art and may be used for the production of such antibody constructs (antibodies and/or fragments). Thus, (antibody) derivatives can be produced by peptidomimetics. Further, techniques described for the production of single chain antibodies (see, inter alia, U.S. Pat. No. 4,946,778, Kontermann and Dübel (2010), loc. cit. and Little (2009), loc. cit.) can be adapted to produce single chain antibodies specific for elected polypeptide(s). Also, transgenic animals or transgenic plants may be used to express humanized antibodies specific for polypeptides and fusion proteins of this invention. For the preparation of monoclonal antibodies, any technique, providing antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of a target polypeptide, such as CD3 epsilon (Schier, Human Antibodies Hybridomas 7 (1996), 97-105; Malmborg, J. Immunol. Methods 183 (1995), 7-13). It is also envisaged in the context of this invention that the term "antibody" comprises antibody constructs, which may be expressed in a host as described herein below, e.g. antibody constructs which may be transfected and/or transduced via, inter alia, viruses or plasmid vectors.

Furthermore, the term "antibody" as employed in the invention also relates to derivatives or variants of the antibodies described herein which display the same specificity as the described antibodies.

The terms "binding domain", "antigen-binding domain", "antigen-binding fragment" and "antibody binding region" when used herein refer to a part of an antibody molecule that comprises amino acids responsible for the specific binding between antibody and antigen. The part of the antigen that is specifically recognized and bound by the antibody is referred to as the "epitope" as described herein above. An antigen-binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, CL and CH1 domains; (2) a F(ab')₂ fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv).

Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al. (1988) Proc. Natl. Acad. Sci USA 85:5879-5883). These antibody fragments are obtained using conventional techniques known to those with skill in the art, and the fragments are evaluated for function in the same manner as are intact antibodies.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The term "human antibody" or "human binding domain" includes antibodies or binding domains having variable and constant regions corresponding substantially to human germline immunoglobulin sequences known in the art, including, for example, those described by Kabat et al. (See Kabat et al. (1991) loc. cit.). The human antibodies or human binding domains of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody or human binding domain can have at least one, two, three, four, five, or more positions replaced with an amino acid residue that is not encoded by the human germline immunoglobulin sequence. It is emphasized that the definition of human antibodies or human binding domains as used herein also contemplates fully human antibodies (or binding domains derived therefrom), which include only non-artificially and/or genetically altered human sequences of antibodies as those can be derived by using technologies using systems such as the Xenomice.

Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

As used herein, an "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term thus preferably excludes sequences generated by genomic rearrangement in an immune cell.

The pairing of a VH and VL together forms a single antigen-binding site. The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit.). The constant domains are not directly involved in antigen binding, but exhibit various effector functions, such as, for example, antibody-dependent, cell-mediated cytotoxicity and complement activation.

The term "CDR" and its plural "CDRs" refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum (Kabat et al., loc. cit.; Chothia et al., J. Mol. Biol, 1987, 196: 901; and MacCallum et al., J. Mol. Biol, 1996, 262: 732). However, the numbering in accordance with the so-called Kabat system is preferred. The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen.

In some embodiments, the antibody constructs of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antibody construct in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, J. Mol. Evol. 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antibody construct CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antibody construct activities, such as M2e binding.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i.e., Kabat et al., loc. cit.); and (2) An approach based on crystallographic studies of antigen-antibody complexes (Chothia, C. et al., J. Mol. Biol. 196: 901-917 (1987)). However, to the extent that two residue identification techniques define regions of overlapping, but not identical regions, they can be combined to define a hybrid CDR. However, in general, the CDR residues are preferably identified in accordance with the so-called Kabat (numbering) system.

The term "framework region" refers to the art-recognized portions of an antibody variable region that exist between the more divergent (i.e., hypervariable) CDRs. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800, each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues. The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1987; J. Mol. Biol. 227:799-817); and Tomlinson et al. (1995) EMBO J. 14: 4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, Calif., 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The term "binding molecule" or "antibody construct" in the sense of the present disclosure indicates a molecule or construct capable of (specifically) binding to, interacting with or recognizing the target molecules M2e and CD3. Such molecules or constructs may include proteinaceous parts and non-proteinaceous parts (e.g. chemical linkers or chemical crosslinking agents such as glutaraldehyde).

In the event that a linker is used, this linker is preferably of a length and sequence sufficient to ensure that each of the first and second domains can, independently from one another, retain their differential binding specificities. Most preferably and as documented in the appended examples, the antibody construct of the invention is a "bispecific single chain antibody construct", more prefereably a bispecific single chain Fv (scFv). Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56.

The variable domains comprised in the herein described antibody constructs may be connected by additional linker sequences. The term "peptide linker" defines in accordance with the present invention an amino acid sequence by which the amino acid sequences of the first domain and the second domain of the antibody construct of the invention are linked with each other. An essential technical feature of such peptide linker is that said peptide linker does not comprise any polymerization activity. Among the suitable peptide linkers are those described in U.S. Pat. Nos. 4,751,180 and 4,935,233 or in WO 88/09344. A preferred embodiment of a peptide linker is characterized by the amino acid sequence Gly-Gly-Gly-Gly-Ser (SEQ ID NO: 91), i.e. Gly$_4$Ser, or polymers thereof, i.e. (Gly$_4$Ser)$_x$, where x is an integer 1 or greater. The characteristics of said peptide linker (comprising e.g. the absence of the promotion of secondary structures) are known in the art and described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which do not promote any secondary structures are preferred. The linkage of said domains to each other can be provided e.g. by genetic engineering, as described in the examples. Methods for preparing fused and operatively linked (bispecific) single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

Peptide linkers which connect the at least two binding domains in the antibody construct of the invention are those peptide linkers which preferable comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or 1 amino acid(s), wherein Gly-rich linkers are preferred. A particularly preferred "single" amino acid in context of said "peptide linker" is Gly. Accordingly, said peptide linker may consist of the single amino acid Gly.

The term "multispecific" as used herein refers to a binding molecule which is an antibody construct and comprises at least a first and a second binding domain, wherein the first binding domain is capable of binding to one antigen or target, and the second binding domain is capable of binding to another antigen or target. Accordingly, antibody constructs according to the invention comprise specificities for at least two different antigens or targets and are hence at least bispecific. The term "antibody construct" according to the invention also comprises multispecific binding molecules such as trispecific binding molecules, the latter ones including three binding domains, or binding molecules having even more binding domains. Furthermore, the antibody construct according to the invention can comprise three (or more) binding domains, of which two (or more) bind to the same antigen or target.

It is also envisaged that the antibody construct of the invention has, in addition to its function to bind to the target molecules M2e and CD3, a further function. In this format, the antibody construct is a tri-functional or multifunctional antibody construct by targeting influenza infected cells through binding to M2e, mediating cytotoxic T cell activity through CD3 binding and providing a further function such as a fully functional Fc constant domain mediating antibody-dependent cellular cytotoxicity through recruitment of effector cells like NK cells, a label (fluorescent etc.), a therapeutic agent such as, e.g. a toxin or radionuclide, and/or means to enhance serum half-life, etc.

In the context of the present invention, the term "binding domain" characterizes a domain which is capable of specifically binding to/interacting with a given target epitope or a given target site on the antigen M2e or CD3.

Binding domains can be derived from a binding domain donor such as for example an antibody. It is envisaged that a binding domain of the present invention comprises at least said part of any of the aforementioned binding domains that is required for binding to/interacting with a given target epitope or a given target site on the target molecules M2e or CD3.

It is envisaged that the binding domain of the aforementioned binding domain donors is characterized by that part of these donors that is responsible for binding the respective target, i.e. when that part is removed from the binding domain donor, said donor loses its binding capability. "Loses" means a reduction of at least 50% of the binding capability when compared with the binding donor. Methods to map these binding sites are well known in the art—it is therefore within the standard knowledge of the skilled person to locate/map the binding site of a binding domain donor and, thereby, to "derive" said binding domain from the respective binding domain donors.

The term "epitope" refers to a site on an antigen to which a binding domain, such as an antibody or immunoglobulin or derivative or fragment of an antibody or of an immunoglobulin, specifically binds. An "epitope" is antigenic and thus the term epitope is sometimes also referred to herein as "antigenic structure" or "antigenic determinant". Thus, the binding domain is an "antigen-interaction-site". Said binding/interaction is also understood to define a "specific recognition". In one example, said binding domain which (specifically) binds to/interacts with a given target epitope or a given target site on the target molecules M2e and CD3 is an antibody or immunoglobulin, and said binding domain is a VH and/or VL region of an antibody or of an immunoglobulin.

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically, a conformational epitope comprises an increased number of amino acids compared with a linear epitope. With regard to recognition of conformational epitopes, the binding domain recognizes a three-dimensional structure of the antigen, preferably a peptide or protein or fragment thereof. For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

As used herein, the term "epitope cluster" denotes the entirety of epitopes lying in a defined contiguous stretch of an antigen. An epitope cluster can comprise one, two or more epitopes. The concept of epitope cluster is also used in the characterization of the features of the antibody constructs of the invention.

The terms "(capable of) binding to", "(capable of) specifically recognizing", "directed to", "specific for" and "(capable of) reacting with" mean in accordance with this invention that a binding domain is capable of specifically interacting with one or more, preferably at least two, more preferably at least three and most preferably at least four amino acids of an epitope.

As used herein, the terms "specifically interacting", "specifically binding" or "specifically bind(s)" mean that a binding domain exhibits appreciable affinity for a particular protein or antigen (in the context of the present invention: M2e and CD3, respectively) and, generally, does not exhibit significant reactivity with proteins or antigens other than M2e or CD3. "Appreciable affinity" includes binding with an affinity of about $10^{-6}$M (KD) or stronger. Preferably, binding is considered specific when binding affinity is about $10^{-12}$ to $10^{-9}$ M, $10^{-12}$ to $10^{-9}$ M, $10^{-12}$ to $10^{-19}$ M, $10^{11}$ to $10^{-9}$ M, preferably of about $10^{-11}$ to $10^{-9}$ M. Whether a binding domain specifically reacts with or binds to a target can be tested readily by, inter alia, comparing the reaction of said binding domain with a target protein or antigen (in the context of the present invention: M2e and CD3, respectively) with the reaction of said binding domain with proteins or antigens other than M2e or CD3. Preferably, a binding domain of the invention does not essentially bind or is not capable of binding to proteins or antigens other than M2e or CD3 (i.e. the first binding domain is not capable of binding to proteins other than M2e and the second binding domain is not capable of binding to proteins other than CD3).

The term "does not essentially bind", or "is not capable of binding" means that a binding domain of the present invention does not bind another protein or antigen other than M2e or CD3, i.e., does not show reactivity of more than 30%, preferably not more than 20%, more preferably not more than 10%, particularly preferably not more than 9%, 8%, 7%, 6% or 5% with proteins or antigens other than M2e or CD3, whereby binding to M2e or CD3, respectively, is set to be 100%.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-site with its specific antigen may result in a simple binding of said site to the antigen. Moreover, the specific interaction of the antigen-interaction-site with its specific antigen may alternatively or additionally result in the initiation of a signal, e.g. due to the induction of a change of the conformation of the antigen, an oligomerization of the antigen, etc.

Proteins (including fragments thereof, preferably biologically active fragments), and peptides (usually having less than 30 amino acids) comprise two or more amino acids coupled to each other via a covalent peptide bond (resulting in a chain of amino acids). The term "polypeptide" as used herein describes a group of molecules which consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a hereteromultimer is an antibody molecule, which, in its naturally occurring form, consists of two identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. A "polypeptide" when referred to herein may also be chemically modified such as pegylated. Such modifications are well known in the art.

"Isolated" when used to describe the antibody construct disclosed herein, means an antibody construct that has been identified, separated and/or recovered from a component of its production environment. Preferably, the isolated antibody construct is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody construct will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

Amino acid sequence modifications of the antibody constructs described herein are contemplated. For example, it may be desirable to improve the binding affinity and/or other biological properties of the antibody. Amino acid sequence variants of the antibody constructs are prepared by introducing appropriate nucleotide changes into the antibody constructs nucleic acid, or by peptide synthesis.

Such modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the antibody constructs, such as changing the number or position of glycosylation sites. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs). The substitutions are preferably conservative substitutions as described herein. Additionally or alternatively, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs.

A useful method for identification of certain residues or regions of the antibody constructs that are preferred locations for mutagenesis is called "alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se needs not to be predetermined. For example, to analyze the performance of a mutation at a given site, alanine scanning or random mutagenesis is conducted at a target codon or region and the expressed antibody construct variants are screened for the desired activity.

Preferably, amino acid sequence insertions include amino- and/or carboxy-terminal fusions ranging in length from 1, 2, 3, 4, 5, 6, 7, 8, 9 or 10 residues to polypeptides containing a hundred or more residues, as well as intrasequence insertions of single or multiple amino acid residues. An insertional variant of the antibody construct includes the fusion to the N-terminus or C-terminus of the antibody to an enzyme or a fusion to a polypeptide which increases the serum half-life of the antibody.

Another type of variant is an amino acid substitution variant. These variants have preferably at least 1, 2, 3, 4, 5, 6, 7, 8, 9 or 10 amino acid residues in the antibody construct replaced by a different residue. The sites of greatest interest for substitutional mutagenesis include the CDRs of the heavy and/or light chain, in particular the hypervariable regions, but FR alterations in the heavy and/or light chain are also contemplated.

For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs of the heavy and/or light chain, it is preferred that the then-obtained "substituted" sequence is at least 60%, more preferably 65%, even more preferably 70%, particularly preferably 75%, more particularly preferably 80% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the antibody construct may have different degrees of identity to their substituted sequences, e.g., CDR-L1 may have 80%, while CDR-L3 may have 90%.

Preferred substitutions (or replacements) are conservative substitutions. However, any substitution (including non-conservative substitution or one or more from the "exemplary substitutions" listed in Table 1, below) is envisaged as long as the antibody construct retains its capability to bind to M2e via the first binding domain and to CD3 via the second binding domain and/or its CDRs have an identity to the then substituted sequence (at least 60%, more preferably 65%, even more preferably 70%, particularly preferably 75%, more particularly preferably 80% identical to the "original" CDR sequence).

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE 1

Amino Acid Substitutions

| Original | Exemplary Substitutions | Preferred Substitutions |
|---|---|---|
| Ala (A) | val, leu, ile | Val |
| Arg (R) | lys, gln, asn | Lys |
| Asn (N) | gln, his, asp, lys, arg | Gln |
| Asp (D) | glu, asn | Glu |
| Cys (C) | ser, ala | Ser |
| Gln (Q) | asn, glu | Asn |
| Glu (E) | asp, gln | Asp |
| Gly (G) | ala | Ala |
| His (H) | asn, gln, lys, arg | Arg |
| Ile (I) | leu, val, met, ala, phe | Leu |
| Leu (L) | norleucine, ile, val, met, ala | Ile |
| Lys (K) | arg, gln, asn | Arg |
| Met (M) | leu, phe, ile | Leu |
| Phe (F) | leu, val, ile, ala, tyr | Tyr |
| Pro (P) | ala | Ala |
| Ser (S) | thr | Thr |
| Thr (T) | ser | Ser |
| Trp (W) | tyr, phe | Tyr |
| Tyr (Y) | trp, phe, thr, ser | Phe |
| Val (V) | ile, leu, met, phe, ala | Leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., the extracellular part of the influenza envelope protein M2. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

Other modifications of the antibody construct are contemplated herein. For example, the antibody construct may be linked to one of a variety of non-proteinaceous polymers, e.g., polyethylene glycol, polypropylene glycol, polyoxyalkylenes, or copolymers of polyethylene glycol and polypropylene glycol. The antibody construct may also be entrapped in microcapsules prepared, for example, by coacervation techniques or by interfacial polymerization (for example, hydroxymethylcellulose or gelatine-microcapsules and poly(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can e.g. be conjugated to the liposomes as described in Martin et al. J. Biol. Chem. 257: 286-288 (1982) via a disulfide interchange reaction. A further anti-viral agent is optionally contained within the liposome. See Gabizon et al. J. National Cancer Inst. 81 (19) 1484 (1989).

When using recombinant techniques, the antibody construct can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*.

The antibody construct composition prepared from the cells can be purified using, for example, hydroxyapatite chromatography, gel electrophoresis, dialysis, ion (anion/cation) exchange chromatography, and affinity chromatography, with affinity chromatography being the preferred purification technique.

The term "nucleic acid" is well known to the skilled person and encompasses DNA (such as cDNA) and RNA (such as mRNA). The nucleic acid can be double stranded and single stranded, linear and circular. The nucleic acid molecule according to the present invention is preferably comprised in a vector. The vector is preferably comprised in a host cell. Said host cell is, e.g. after transformation or transfection with the nucleic acid molecule of the invention, capable of expressing the antibody construct. For that purpose the nucleic acid molecule is operatively linked with control sequences.

A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence, which comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) are specifically suitable for the expression of the transgene in the target cell, and generally have control sequences such as a promoter sequence that drives expression of the transgene. Insertion of a vector into the target cell is usually called "transformation" for bacteria, "transfection" for eukaryotic cells, although insertion of a viral vector is also called "transduction".

As used herein, the term "host cell" is intended to refer to a cell into which a nucleic acid encoding the antibody construct of the invention is introduced by way of transformation, transfection and the like. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "expression" includes any one or more steps involved in the production of an antibody construct of the invention including, but not limited to, transcription, post-transcriptional modification, translation, post-translational modification, and secretion.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid molecule is "operably linked" when it is placed into a functional relationship with another nucleic acid molecule. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "host cell," "target cell" or "recipient cell" are intended to include any individual cell or cell culture that can be or has been a recipient for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacteria, yeast cells, animal cells, and mammalian cells, e.g., murine, rat, macaque or human.

Suitable host cells include prokaryotes and eukaryotic host cells including yeasts, fungi, insect cells and mammalian cells.

The antibody construct of the invention can be produced in bacteria. After expression, the antibody construct of the invention, preferably the antibody construct is isolated from the E. coli cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the antibody construct of the invention. Saccharomyces cerevisiae, or common baker's yeast, is the most commonly used among lower eukaryotic host microorganisms. However, a number of other genera, species, and strains are commonly available and useful herein, such as Schizosaccharomyces pombe, Kluyveromyces hosts such as, e.g., K. lactis, K. fragilis (ATCC 12424), K. bulgaricus (ATCC 16045), K. wickeramii (ATCC 24178), K. waltii (ATCC 56500), K. drosophilarum (ATCC 36906), K. thermotolerans, and K. marxianus; yarrowia (EP 402 226); Pichia pastoris (EP 183 070); Candida; Trichoderma reesia (EP 244 234); Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Suitable host cells for the expression of glycosylated antibody construct of the invention, preferably antibody derived antibody constructs are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruit fly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the present invention, particularly for transfection of Spodoptera frugiperda cells.

Plant cell cultures of cotton, corn, potato, soybean, petunia, tomato, Arabidopsis and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986. Alternatively, whole plants may be used for the antibody production, as disclosed in WO2013/006244.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL51); TRI cells (Mather et al., Annals N. Y Acad. Sci. 383: 44-68 (1982)); MRC 5 cells; FS4 cells; and a human hepatoma line (Hep G2).

When using recombinant techniques, the antibody construct of the invention can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody construct of the invention prepared from the host cells can be purified using, for example, hydroxyapatite chromatography, ion (anion/cation) exchange chromatography, gel electrophoresis, dialysis, and affinity chromatography, with affinity chromatography being the preferred purification technique.

The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose. Where the antibody construct of the invention comprises a CH3 domain, the Bakerbond ABXMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromato-focusing, SDS-PAGE, and ammonium sulfate precipitation are also available depending on the antibody to be recovered.

The term "culturing" refers to the in vitro maintenance, differentiation, growth, proliferation and/or propagation of cells under suitable conditions in a medium.

The present invention further refers to a pharmaceutical composition comprising the antibody construct of the invention.

As used herein, the term "pharmaceutical composition" relates to a composition for administration to a patient, preferably a human patient. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. In particular, the present invention provides for an uninterrupted administration of the suitable composition. As a non-limiting example, uninterrupted, i.e. continuous administration may be realized by a small pump system worn by the patient for metering the influx of therapeutic agent into the body of the patient. The pharmaceutical composition comprising the antibody construct of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the antibody constructs of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

The pharmaceutical composition according to the invention may further comprise a pharmaceutically acceptable carrier. Examples of suitable pharmaceutical carriers are well known in the art and include solutions, e.g. phosphate buffered saline solutions, water, emulsions, such as oil/water emulsions, various types of wetting agents, sterile solutions, liposomes, etc. Compositions comprising such carriers can be formulated by well known conventional methods. Formulations can comprise carbohydrates, buffer solutions, amino acids and/or surfactants. Carbohydrates may be non-reducing sugars, preferably trehalose, sucrose, octasulfate, sorbitol or xylitol. In general, as used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counter-ions, such as sodium, polyhydric sugar alcohols; amino acids, such as alanine, glycine, asparagine, 2-phenylalanine, and threonine; sugars or sugar alcohols, such as trehalose, sucrose, octasulfate, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Such formulations may be used for continuous administrations which may be intravenuous or subcutaneous with and/or without pump systems. Amino acids may be charged amino acids, preferably lysine, lysine acetate, arginine, glutamate and/or histidine. Surfactants may be detergents, preferably with a molecular weight of >1.2 KD and/or a polyether, preferably with a molecular weight of >3 KD. Non-limiting examples for preferred detergents are Tween 20, Tween 40, Tween 60, Tween 80 or Tween 85. Non-limiting examples for preferred polyethers are PEG 3000, PEG 3350, PEG 4000 or PEG 5000. Buffer systems used in the present invention can have a preferred pH of 5-9 and may comprise citrate, succinate, phosphate, histidine and acetate.

The compositions of the present invention can be administered to the subject at a suitable dose which can be determined e.g. by dose escalating studies by administration of increasing doses of the polypeptide of the invention exhibiting cross-species specificity described herein to non-chimpanzee primates, for instance macaques. As set forth above, the antibody construct of the invention exhibiting cross-species specificity described herein can be advantageously used in identical form in preclinical testing in non-chimpanzee primates and as drug in humans. These compositions can also be administered in combination with other proteinaceous and non-proteinaceous drugs. These drugs may be administered simultaneously with the composition comprising the polypeptide of the invention as defined herein or separately before or after administration of said polypeptide in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the composition of the invention might comprise, in addition to the polypeptide of the invention defined herein, further biologically active agents, depending on the intended use of the composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art. It is also envisaged that the antibody construct of the present invention is applied in a co-therapy, i.e., in combination with one or more further antiviral drugs, such as M2 inhibitors (e.g. amantadine or rimantadine) and neuraminidase inhibitors (such as zanamivir, oseltamivir or laninamivir), arbidol, peramivir, interferons, viferon, grippferon, herbal medicines, N-acetylcysteine, elderberry, antibiotics, Obatoclax Mesylate, HA-14, Alsterpaullone, L glutathione reduced, Fluocinolone acetonide, Tirofiban, Menadione Crystalline and derivatives or analogues thereof, or other antibody constructs.

According to a preferred embodiment, the present invention provides a pharmaceutical composition comprising an antibody construct according to the invention or produced according to the process of the invention, and a reactive oxygen scavenger for the amelioration or treatment of an influenza A virus infection.

A reactive oxygen scavenger (sometimes also denoted antioxidant) is in essence a molecule that decreases or even inhibits the oxidation of other molecules. In the context of the present invention said reactive oxygen scavenger is preferably biocompatible (i.e. a substance which is in the amount employed non-toxic). A reactive oxygen scavenger is a compound that prevents or reduces the formation of reactive oxygen species (ROS) or that neutralizes or at least partly neutralizes ROS. Examples of ROS include superoxide anion, peroxynitrite, hydrogen peroxide and hydroxylradicals. These molecules can be produced by cells, and excess ROS is cytotoxic and can lead to pro-inflammatory cytokine production. Infiltrating inflammatory cells such as neutrophils can produce ROS which in turn can lead to tissue damage. Oxygen radical scavengers such as apocyin, which inhibits Nox2, the catalytic subunit of NADPH oxidase, can be used to suppress ROS formation by cells. Antioxidants such as tempol can neutralize ROS.

Suitable reactive oxygen scavengers can be selected from the group comprising vitamin E (DL-a-tocopherol), vitamin C (L-ascorbic acid), co-enzyme Q10, zinc, selenium, N-acetyl-L-cycteine, N-acetyl-S-farnesyl-L-cysteine, Bilirubin, caffeic acid, citric acid, CAPE, catechin, ceruloplasmin, Coelenterazine, copper diisopropylsalicylate, deferoxamine mesylate, R-(−)-deprenyl, DMNQ, DTPA dianhydride, Ebselen, ellagic acid, (−)-epigallocatechin, L-ergothioneine, EUK-8, Ferritin, glutathione, glutathione monoethylester, a-lipoic acid, Luteolin, Manoalide, MCI-186, MnTBAP, MnTMPyP, morin hydrate, NCO-700, NDGA, p-Nitroblue, propyl gallate, Resveratrol, rutin, silymarin, L-stepholidine, taxifolin, tetrandrine, tocopherol acetate, tocotrienol, Trolox®, U-74389G, U-83836E, and uric acid (all available from Calbiochem, San Diego, Calif., U.S.A.), and phenolic compounds such as BHA (butylated hydroxyanisole), BHT (butylated hydroxytoluene), propyl gallate, TBHQ (tert-butyl hydroquinone), tocopherols, lecithin, gums and resin guiac, THBP (trihydroxybutyrophenone), dithioerythritol, sodium thionite, thiodipropionic acid, dilauryl thiodipropionate, and glycines. The amount of reactive oxygen scavenger within the pharmaceutical composition of the invention will generally for each compound be at a concentration of about 0.001 M-0.5 M, preferably at about 0.01 M-0.25 M, more preferably about 0.05 M-0.20 M, and most preferably at a concentration of 0.10 M-0.15 M.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention. The success or in vivo efficacy of the therapy using a pharmaceutical composition of the invention refers to the effectiveness of the composition for its intended purpose, i.e. the ability of the composition to cause its desired effect, e.g. depletion of influenza A infected cells. The in vivo efficacy may be monitored by established standard methods for an Influenza infection. The United States Centers for Disease Control and Prevention (CDC) maintains an up-to-date summary of available laboratory tests, such as viral cell culture (conventional), rapid cell culture (shell vials, cell mixtures), immuno-fluorescence, direct (DFA) or indirect (IFA) antibody staining, RT-PCR (singleplex and multiplex, real-time and other RNA-based) and other molecular assays, as well as rapid Influenza diagnostic tests. Further methods include, but are not limited to: Resequencing Pathogen Microarray, Electrasense® Influenza A assay, automated microarray or next generation sequence analysis. Other methods such as quantitative PCR (Polymerase Chain Reaction) assay of viral RNA may also be used. Further methods include, but are not limited to the cytotoxicity assay as depicted herein, inter alia in Example 8.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc. By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of (bispecific) single chain antibodies exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the subject's own immune system. The term "patient" includes human and other mammalian subjects that receive either prophylactic or therapeutic treatment.

The term "effective and non-toxic dose" as used herein refers to a tolerable dose of an inventive antibody construct which is high enough to cause depletion of influenza A infected cells, without or essentially without major toxic effects. Such effective and non-toxic doses may be determined e.g. by dose escalation studies described in the art and should be below the dose inducing severe adverse side events (dose limiting toxicity, DLT).

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

The appropriate dosage, or therapeutically effective amount, of the antibody construct of the invention will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies such as anti-viral therapies as needed.

The pharmaceutical compositions of this invention are particularly useful for parenteral administration, i.e., subcutaneously, intramuscularly, intravenously, intra-articular and/or intra-synovial. Parenteral administration can be by bolus injection or continuous infusion.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

As stated above, the present invention provides an antibody construct comprising a first human binding domain specific for the extracellular part of the influenza envelope protein M2 (M2e), characterized by its six CDR sequences, and a second domain specific for CD3.

The "extracellular part of M2" or "M2 extracellular domain" or "M2 ECD" or "M2e" refers to a form or fragment or part of M2 which is essentially free of transmembrane and cytoplasmic domains of M2. It will be understood by the skilled artisan that the transmembrane domain identified for the M2 polypeptide of the present invention is identified pursuant to criteria routinely employed in the art for identifying that type of hydrophobic domain. The exact boundaries of a transmembrane domain may vary but most likely by no more than about 5 amino acids at either end of the domain specifically mentioned herein. A preferred (consensus) M2-ECD is shown in SEQ ID NO: 90. In this context it is understood that the M2-ECD represents the part of M2 on the surface of a target cell.

When the present specification refers to the—target molecule M2e", the "protein M2e", the "antigen M2e" or similar expressions, it is clear to the skilled reader that these terms encompass the extracellular part of the M2 protein not only as an "isolated" M2 fragment, but also in the context of the whole M2 protein. An antibody construct having a binding domain specific for M2e will hence preferably be able to bind to M2e as being an integral part of the M2 protein.

The T cell CD3 receptor complex is a protein complex and is composed of four distinct chains. In mammals, the complex contains a CD3γ chain, a CD3δ chain, and two CD3ε (epsilon) chains. These chains associate with a molecule known as the T cell receptor (TCR) and the 4 chain to generate an activation signal in T lymphocytes.

The redirected lysis of target cells via the recruitment of T cells by a multispecific, at least bispecific, antibody construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

The affinity of the first binding domain for M2e is preferably ≤25 nM, more preferably ≤15 nM, more preferably ≤10 nM, even more preferably ≤5 nM, even more preferably ≤1 nM, even more preferably ≤0.5 nM, even more preferably ≤0.1 nM, and most preferably ≤0.05 nM or even ≤0.01 nM. The affinity can be measured for example in a cell-based assay, a Biacore assay or in a Scatchard assay, e.g. as described in the Examples. Other methods of determining the affinity are well-known to the skilled person.

Human antibodies or antibody constructs avoid some of the problems associated with antibodies/antibody constructs that possess murine or rat variable and/or constant regions. The presence of such murine or rat derived proteins can lead to the rapid clearance of the antibodies/antibody constructs or can lead to the generation of an immune response against the antibody/antibody construct by a patient. In order to avoid the utilization of murine or rat derived antibodies/antibody constructs, human or fully human antibodies can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies/antibody constructs are expected to minimize the immunogenic and allergic responses intrinsic to mouse or mouse-derivatized mAbs and thus to increase the efficacy and safety of the administered antibodies/antibody constructs. The use of fully human antibodies/antibody constructs can be expected to provide a substantial advantage in the treatment of chronic and recurring human diseases, such as inflammation, autoimmunity, and cancer, which require repeated compound administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with the generation of the first XenoMouse mouse strains, as published in 1994 (see Green et al. Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes.

This was demonstrated by their ability to induce B-cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620, filed Dec. 3, 1996, the disclosures of which are hereby incorporated by reference.

The production of the XenoMouse mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998). See also European Patent No., EP 0 463151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000, WO 03/47336. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B 1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996, 5,698,767, and 5,958,765.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against EGFRvIII in order to vitiate concerns and/or effects of HAMA or HACA response.

Cytotoxicity mediated by M2e/CD3 specific antibody constructs can be measured in various ways. Effector cells can be e.g. stimulated enriched (human) CD8 positive T cells or unstimulated (human) peripheral blood mononuclear cells (PBMC). The target cells should express the extracellular domain of M2. Target cells can be a cell line (such as CHO) which is stably or transiently transfected with M2, M2e or an M2e fusion protein. Usually EC50-values are expected to be lower with target cell lines expressing higher levels of M2e on the cell surface. The effector to target cell (E:T) ratio is usually about 10:1, but can also vary. Cytotoxic activity of M2e/CD3 specific antibody constructs can be measured in a 51-chromium release assay (incubation time of about 18 hours) or in a in a FACS-based cytotoxicity assay (incubation time of about 48 hours). Modifications of the assay incubation time (cytotoxic reaction) are also possible. Other methods of measuring cytotoxicity are well-known to the skilled person and comprise MTT or MTS assays, ATP-based assays including bioluminescent assays, the sulforhodamine B (SRB) assay, WST assay, clonogenic assay and the ECIS technology.

The cytotoxic activity mediated by M2e/CD3 specific antibody constructs of the present invention is preferably measured in a cell-based cytotoxicity assay. It is represented by the $EC_{50}$ value, which corresponds to the half maximal effective concentration (concentration of the antibody construct which induces a cytotoxic response halfway between the baseline and maximum). Preferably, the $EC_{50}$ value of the M2e/CD3 specific antibody constructs is ≤20.000 pg/ml, more preferably ≤5000 pg/ml, even more preferably ≤2500 pg/ml, even more preferably ≤2000 pg/ml, even more preferably ≤1000 pg/ml, even more preferably ≤750 pg/ml, even more preferably ≤600 pg/ml, even more preferably ≤500 pg/ml, even more preferably ≤400 pg/ml, even more preferably ≤300 pg/ml, even more preferably ≤200 pg/ml, even more preferably ≤100 pg/ml, even more preferably ≤50 pg/ml, and most preferably ≤10 pg/ml or ≤5 pg/ml.

Any of the above indicated $EC_{50}$ values can be combined with any one of the previously described scenarios for a cell-based cytotoxicity assay, where the nature of the effector cells, the nature of the target cells, the E:T ratio, the incubation time, or the readout system are specified.

The difference in cytotoxic activity between the monomeric and the dimeric isoform of individual M2e/CD3 specific antibody constructs is referred to as "potency gap". This potency gap can e.g. be calculated as ratio between $EC_{50}$ values of the molecule's monomeric and dimeric form. Potency gaps of the M2e/CD3 specific antibody constructs of the present invention are preferably ≤5, more preferably ≤4, even more preferably ≤3, even more preferably ≤2 and most preferably ≤1.

The antibody construct of the invention is a fusion protein comprising at least two binding domains, with or without peptide linkers (spacer peptides). Among the suitable peptide linkers are those described in U.S. Pat. Nos. 4,751,180 and 4,935,233 or WO 88/09344.

Another method for preparing oligomeric antibody construct derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one approach, recombinant fusion proteins comprising M2e antibody fragment or derivative fused to a leucine zipper peptide are expressed in suitable host cells, and the soluble oligomeric M2e antibody fragments or derivatives that form are recovered from the culture supernatant.

Covalent modifications of antibody constructs are included within the scope of this invention, and are generally, but not always, done post-translationally. For example, several types of covalent modifications of the antibody constructs can be introduced into the molecule by reacting specific amino acid residues of the antibody constructs with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibody constructs to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, 1983, pp. 79-86), acetylation of the N-terminal amine, and amidation of any C-terminal carboxyl group.

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody constructs is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody constructs' amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody constructs is by chemical or enzymatic coupling of glycosides to the constructs. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antibody constructs comprises linking the antibody constructs to various non-proteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antibody constructs to facilitate the addition of polymers such as PEG.

In some embodiments, the covalent modification of the antibody constructs of the invention comprises the addition of one or more labels.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter.

The term "labelling group" means any detectable label. Examples of suitable labelling groups include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antibody constructs via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc.

1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

The antibody construct of the invention may also comprise additional domains which are e.g. helpful in the isolation of the molecule or relate to an adapted pharmacokinetic profile of the molecule.

Domains helpful for the isolation of an antibody construct may be elected from peptide motives or secondarily introduced moieties, which can be captured in an isolation method, e.g. an isolation column. According to a non-limiting embodiment, such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All antibody constructs disclosed herein and characterized by the identified CDRs preferably comprise a His-tag domain, which is generally known as a repeat of consecutive His residues in the amino acid sequence of a molecule, preferably of six His residues.

In one aspect of the invention, the second binding domain is capable of binding to human CD3 and to macaque CD3, preferably to human CD3 epsilon and to macaque CD3 epsilon.

Additionally or alternatively, the second binding domain is capable of binding to *Callithrix jacchus, Saguinus oedipus* and/or *Saimiri sciureus* CD3 epsilon. According to these embodiments, one or both binding domains of the antibody construct of the invention are preferably cross-species specific for members of the mammalian order of primates. Cross-species specific CD3 binding domains are, for example, described in WO 2008/119567.

It is particularly preferred for the antibody construct of the present invention that the second binding domain specific for CD3 comprises a VL region comprising CDR-L1, CDR-L2 and CDR-L3 selected from:
(a) CDR-L1 as depicted in SEQ ID NO: 27 of WO 2008/119567, CDR-L2 as depicted in SEQ ID NO: 28 of WO 2008/119567 and CDR-L3 as depicted in SEQ ID NO: 29 of WO 2008/119567;
(b) CDR-L1 as depicted in SEQ ID NO: 117 of WO 2008/119567, CDR-L2 as depicted in SEQ ID NO: 118 of WO 2008/119567 and CDR-L3 as depicted in SEQ ID NO: 119 of WO 2008/119567; and
(c) CDR-L1 as depicted in SEQ ID NO: 153 of WO 2008/119567, CDR-L2 as depicted in SEQ ID NO: 154 of WO 2008/119567 and CDR-L3 as depicted in SEQ ID NO: 155 of WO 2008/119567.

In an alternatively preferred embodiment of the antibody construct of the present invention, the second binding domain specific for CD3 comprises a VH region comprising CDR-H1, CDR-H2 and CDR-H3 selected from:
(a) CDR-H1 as depicted in SEQ ID NO: 12 of WO 2008/119567, CDR-H2 as depicted in SEQ ID NO: 13 of WO 2008/119567 and CDR-H3 as depicted in SEQ ID NO: 14 of WO 2008/119567;
(b) CDR-H1 as depicted in SEQ ID NO: 30 of WO 2008/119567, CDR-H2 as depicted in SEQ ID NO: 31 of WO 2008/119567 and CDR-H3 as depicted in SEQ ID NO: 32 of WO 2008/119567;
(c) CDR-H1 as depicted in SEQ ID NO: 48 of WO 2008/119567, CDR-H2 as depicted in SEQ ID NO: 49 of WO 2008/119567 and CDR-H3 as depicted in SEQ ID NO: 50 of WO 2008/119567;
(d) CDR-H1 as depicted in SEQ ID NO: 66 of WO 2008/119567, CDR-H2 as depicted in SEQ ID NO: 67 of WO 2008/119567 and CDR-H3 as depicted in SEQ ID NO: 68 of WO 2008/119567;
(e) CDR-H1 as depicted in SEQ ID NO: 84 of WO 2008/119567, CDR-H2 as depicted in SEQ ID NO: 85 of WO 2008/119567 and CDR-H3 as depicted in SEQ ID NO: 86 of WO 2008/119567;
(f) CDR-H1 as depicted in SEQ ID NO: 102 of WO 2008/119567, CDR-H2 as depicted in SEQ ID NO: 103 of WO 2008/119567 and CDR-H3 as depicted in SEQ ID NO: 104 of WO 2008/119567;
(g) CDR-H1 as depicted in SEQ ID NO: 120 of WO 2008/119567, CDR-H2 as depicted in SEQ ID NO: 121 of WO 2008/119567 and CDR-H3 as depicted in SEQ ID NO: 122 of WO 2008/119567;
(h) CDR-H1 as depicted in SEQ ID NO: 138 of WO 2008/119567, CDR-H2 as depicted in SEQ ID NO: 139 of WO 2008/119567 and CDR-H3 as depicted in SEQ ID NO: 140 of WO 2008/119567;
(i) CDR-H1 as depicted in SEQ ID NO: 156 of WO 2008/119567, CDR-H2 as depicted in SEQ ID NO: 157 of WO 2008/119567 and CDR-H3 as depicted in SEQ ID NO: 158 of WO 2008/119567; and
(j) CDR-H1 as depicted in SEQ ID NO: 174 of WO 2008/119567, CDR-H2 as depicted in SEQ ID NO: 175 of WO 2008/119567 and CDR-H3 as depicted in SEQ ID NO: 176 of WO 2008/119567.

It is further preferred for the antibody construct of the present invention that the second binding domain specific for CD3 comprises a VL region selected from the group consisting of a VL region as depicted in SEQ ID NO: 35, 39, 125, 129, 161 or 165 of WO 2008/119567.

It is alternatively preferred that the second binding domain specific for CD3 comprises a VH region selected from the group consisting of a VH region as depicted in SEQ ID NO: 15, 19, 33, 37, 51, 55, 69, 73, 87, 91, 105, 109, 123, 127, 141, 145, 159, 163, 177 or 181 of WO 2008/119567.

More preferably, the antibody construct of the present invention is characterized by the second binding domain specific for CD3 and comprising a VL region and a VH region selected from the group consisting of:
(a) a VL region as depicted in SEQ ID NO: 17 or 21 of WO 2008/119567 and a VH region as depicted in SEQ ID NO: 15 or 19 of WO 2008/119567;
(b) a VL region as depicted in SEQ ID NO: 35 or 39 of WO 2008/119567 and a VH region as depicted in SEQ ID NO: 33 or 37 of WO 2008/119567;
(c) a VL region as depicted in SEQ ID NO: 53 or 57 of WO 2008/119567 and a VH region as depicted in SEQ ID NO: 51 or 55 of WO 2008/119567;
(d) a VL region as depicted in SEQ ID NO: 71 or 75 of WO 2008/119567 and a VH region as depicted in SEQ ID NO: 69 or 73 of WO 2008/119567;
(e) a VL region as depicted in SEQ ID NO: 89 or 93 of WO 2008/119567 and a VH region as depicted in SEQ ID NO: 87 or 91 of WO 2008/119567;

(f) a VL region as depicted in SEQ ID NO: 107 or 111 of WO 2008/119567 and a VH region as depicted in SEQ ID NO: 105 or 109 of WO 2008/119567;

(g) a VL region as depicted in SEQ ID NO: 125 or 129 of WO 2008/119567 and a VH region as depicted in SEQ ID NO: 123 or 127 of WO 2008/119567;

(h) a VL region as depicted in SEQ ID NO: 143 or 147 of WO 2008/119567 and a VH region as depicted in SEQ ID NO: 141 or 145 of WO 2008/119567;

(i) a VL region as depicted in SEQ ID NO: 161 or 165 of WO 2008/119567 and a VH region as depicted in SEQ ID NO: 159 or 163 of WO 2008/119567; and (j) a VL region as depicted in SEQ ID NO: 179 or 183 of WO 2008/119567 and a VH region as depicted in SEQ ID NO: 177 or 181 of WO 2008/119567.

According to a preferred embodiment of the antibody construct of the present invention, in particular the second binding domain specific for CD3, the pairs of VH-regions and VL-regions are in the format of a single chain antibody (scFv). The VH and VL regions are arranged in the order VH-VL or VL-VH. It is preferred that the VH-region is positioned N-terminally to a linker sequence. The VL-region is positioned C-terminally of the linker sequence.

A preferred embodiment of the above described antibody construct of the present invention is characterized by the second binding domain specific for CD3 and comprising an amino acid sequence selected from the group consisting of SEQ ID NOs: 23, 25, 41, 43, 59, 61, 77, 79, 95, 97, 113, 115, 131, 133, 149, 151, 167, 169, 185 or 187 of WO 2008/119567.

The formulations described herein are useful as pharmaceutical compositions in the treatment, amelioration and/or prevention of an influenza A virus infection as described herein in a patient in need thereof. The term "treatment" refers to both therapeutic treatment and prophylactic or preventative measures. Treatment includes the application or administration of the composition to the body, an isolated tissue, or cell from a patient who has an infection with influenza A virus, a symptom of an influenza A virus infection, or a predisposition toward an influenza A virus infection, with the purpose to cure, heal, alleviate, relieve, alter, remedy, ameliorate, improve, or affect the disease, the symptom of the disease, or the predisposition toward the disease.

Those "in need of treatment" include those already with the disorder, as well as those in which the disorder is to be prevented. The term "disease" or "disorder" is any condition that would benefit from treatment with the protein formulation described herein. This includes chronic and acute disorders or diseases including those pathological conditions that predispose the mammal to the disease in question. A non-limiting example for a disease/disorder to be treated herein includes influenza infection, in particular with Influenza A virus. Influenza, commonly known as "flu", is an infectious disease of birds and mammals caused by RNA viruses of the family of Orthomyxoviridae, the influenza viruses. The genus "Influenza A" has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to hemagglutinin (HA) and neuraminidase (NA). These different types of HA and NA form the basis of the H and N distinctions. There are 16 H- and 9 N-subtypes known. The serotypes that have been confirmed in humans, ordered by the number of known human pandemic deaths, are: H1N1, H2N2, H3N2, H5N1, H7N7, H1N2, H9N2, H7N2, H7N3, and H10N7.

The most common symptoms are chills, fever, sore throat, muscle pains, (severe) headache, nasal congestion, irritated eyes, coughing, weakness, body aches, fatigue, loss of appetite and general discomfort. Influenza may produce nausea and vomiting and can occasionally lead to pneumonia.

In some embodiments, the invention provides a pharmaceutical composition comprising a therapeutically effective amount of one or more of the antibody constructs of the invention together with a pharmaceutically effective diluent, carrier, solubilizer, emulsifier, preservative, and/or adjuvant. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprise a therapeutically effective amount of an antibody construct of the invention.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody constructs of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefore. In certain embodiments, compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the antibody construct of the invention may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired human antibody or antigen binding fragment thereof of the invention or the antibody construct of the invention in a pharmaceutically acceptable vehicle. A particularly suitable vehicle for parenteral injection is sterile distilled water in which the antibody construct of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody construct.

Additional pharmaceutical compositions will be evident to those skilled in the art, including formulations involving the antibody construct of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly(2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions are generally placed into a container having a sterile access port, for example, an intravenous solution bag or vial having a stopper pierceable by a hypodermic injection needle.

One aspect of the invention includes a self-buffering formulation comprising the antibody construct of the invention, which can be used as pharmaceutical composition, as described in international patent application WO 06138181 A2 (PCT/US2006/022599), which is incorporated by reference in its entirety herein.

Excipients can be used for the composition of the invention for a wide variety of purposes, such as adjusting physical, chemical, or biological properties of formulations, e.g. adjustment of viscosity, stabilizing formulations against degradation and spoilage due to stresses that occur e.g. during manufacturing, shipping, storage, pre-use preparation, administration, etc.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention.

Salts may be used in accordance with certain embodiments of the invention in order to e.g. adjust the ionic strength and/or the isotonicity of a formulation and/or to improve the solubility and/or physical stability of a protein or other ingredient of a composition in accordance with the present invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used for the pharmaceutical compositions of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as glycerol and propylene glycol, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Mannitol is a particularly useful polyol for the pharmaceutical compositions of the present invention. Mannitol is commonly used to ensure structural stability of the cake in lyophilized formulations. It is generally used with a lyoprotectant, e.g., sucrose. Sorbitol and sucrose are among the preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they are generally not among preferred polyols for use in accordance with the present invention. In addition, sugars which form such reactive species, such as sucrose, which is hydrolyzed to fructose and glucose under acidic conditions, and consequently engenders glycation, also is not among the preferred polyols of the invention in this regard. PEG is useful to stabilize proteins and as a cryoprotectant and can be used in the invention in this regard.

Embodiments of the antibody construct of the invention formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct of the invention formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among the useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. Ca+2 ions (up to 100 mM) can increase the stability of human deoxyribonuclease. Mg+2, Mn+2, and Zn+2, however, can destabilize rhDNase. Similarly, Ca+2 and Sr+2 can stabilize Factor VIII, it can be destabilized by Mg+2, Mn+2 and Zn+2, Cu+2 and Fe+2, and its aggregation can be increased by Al+3 ions.

Embodiments of the antibody construct of the invention formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

The antibody construct of the invention generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

In another aspect, kits are provided comprising antibody construct of the invention, a nucleic acid molecule of the invention, a vector of the invention, or a host cell of the invention. The kit may comprise one or more vials containing the binding molecule and instructions for use. The kit may also contain means for administering the binding molecule of the present invention such as a syringe, pump, infuser or the like, means for reconstituting the binding molecule of the invention and/or means for diluting the binding molecule of the invention. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an antibody construct of the invention to be employed will depend, for example, upon the therapeutic context and objectives. One skilled in the art will appreciate that the appropriate dosage levels for treatment will vary depending, in part, upon the antibody construct delivered, the indication for which the antibody construct of the invention is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of an antibody construct of the invention preferably results in a decrease in severity of disease symptoms, in increase in frequency or duration of disease symptom-free periods or a prevention of impairment or disability due to the disease affliction. For treating a subject having an infection with Influenza A virus, a therapeutically effective amount of the anti-M2e/CD3 antibody construct of the invention preferably results in decrease of the symptoms as described herein before, such as duration of fever, height of fever, reduction in time and severity of other symptoms such as muscle ache, nausea, headache, tiredness, loss of appetite. The ability of a compound to decrease the symptoms described above may be evaluated in an animal model predictive of efficacy in humans. Non-limiting examples for animal species which can be used in such corresponding modes include ferrets, mice, chickens, swine or and primates such as e.g. macacas such as cynomolgus monkeys or rhesus monkeys.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

It should be understood that the inventions herein are not limited to particular methodology, protocols, or reagents, as such can vary. The discussion and examples provided herein are presented for the purpose of describing particular embodiments only and are not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

Examples

The following examples are provided for the purpose of illustrating specific embodiments or features of the present invention. These examples should not be construed as to limit the scope of this invention. The examples are included for purposes of illustration, and the present invention is limited only by the claims.

1. Generation of Anti-M2e Bispecific Constructs

A murine monoclonal antibody directed against M2e was generated. The VH and VL sequence of the murine monoclonal anti-M2e antibody (as depicted in SEQ ID NOs: 80 and 82, respectively) were amplified by flanking primers containing suitable restriction sites and combined to a single-chain Fv by insertion of a sequence coding for a glycine-serine $(G_4S)_3$ linker. The described murine anti-M2e scFv (SEQ ID NO: 84) was fused to a cross-species-specific human CD3 binder or a mouse CD3 binder (SEQ ID NO: 88) by a sequence coding for a $G_4S$ linker. Bispecific anti-M2e constructs with a second binding moiety specific for human CD3 are called "hBiTE", bispecific anti-M2e constructs with a second binding moiety specific for mouse CD3 are called "mBiTE".

2. Cloning and Expression of the Influenza A M2 Protein

The coding sequence for the full length M2 protein (containing the M2e consensus sequence as described by Schotsaert, De Filette et al. (2009)) was amplified using standard PCR methods, and flanking primers containing restriction sites which were introduced at the beginning and at the end of the DNA fragment. The restriction sites EcoRI at the 5' end and SalI at the 3' end were used in the following cloning procedures. The fragment was digested with EcoRI and SalI and cloned into pEF-DHFR (pEF-DHFR is described in Mack, Riethmuller et al. (1995)) following standard protocols. A sequence verified plasmid was used to transfect CHO/dhfr-cells (ATCC No. CRL 9096). Cells were cultivated in RPMI 1640 with stabilized glutamine, supplemented with 10% FCS, 1% penicillin/streptomycin (all obtained from Biochrom AG Berlin, Germany) and nucleosides from a stock solution of cell culture grade reagents (Sigma-Aldrich Chemie GmbH, Taufkirchen, Germany) to a final concentration of 10 µg/ml Adenosine, 10 µg/ml Deoxyadenosine and 10 µg/ml Thymidine, in an incubator at 37° C., 95% humidity and 7% $CO_2$. Transfection was performed using the PolyFect Transfection Reagent (Qiagen GmbH, Hilden, Germany) and 5 µg of plasmid DNA according to the manufacturer's protocol. After cultivation for 24 hours cells were washed once with PBS and cultivated again in RPMI 1640 with stabilized glutamine and 1% penicillin/streptomycin. Thus the cell culture medium did not contain nucleosides and thereby selection was applied on the transfected cells. Approximately 14 days after transfection the outgrowth of resistant cells was observed. After an additional 7 to 14 days the transfectants were tested for expression of the construct by FACS analysis. $2.5 \times 10^5$ cells were incubated with 50 µl of an anti-Influenza A M2 antibody (ab5416; Abcam plc, Cambridge, UK) diluted to 5 µg/ml in PBS with 2% FCS. The binding of the antibody was detected with a R-Phycoerythrin-conjugated affinity purified F(ab')2 fragment, goat anti-mouse IgG, Fc-gamma fragment specific diluted 1:200 in PBS with 2% FCS (ImmunoResearch Europe Ltd., Newmarket, Suffolk, UK). The samples were measured on a FACScalibur (BD biosciences, Heidelberg, Germany).

3. Purification of M2e/CD3 Bispecific Antibodies

Human embryonal kidney (HEK 293-F; Life Technologies, Darmstadt, Germany) cells were transiently transfected with 200 µg of a pEF-DHFR vector encoding the M2e/CD3 bispecific antibody sequence using 293 fectin (Life Technologies, Darmstadt, Germany) according to the manufacturer's instructions. Transfected cells were cultivated in Erlenmeyer cell culture flasks for 72 hours at 37° C., 135 rpm, 5% $CO_2$. Alternatively, Chinese hamster ovary CHO cells stably transfected with a pEF-DHFR vector coding the M2e/CD3 bispecific antibody sequence and growing in HyClone PF CHO LS w/L-Glutamine (Thermo Scientific, Bonn, Germany) supplemented with 1% penicillin/streptomycin (Biochrom AG, Berlin, Germany) and 20 nM or 100 nM Methotrexate (MTX) were cultivated in roller bottles until approximately 60% remaining vitality was reached. The cell culture supernatant containing the 6×His-tagged M2e/CD3 bispecific antibody molecules was cleared by centrifugation at 1400 rpm for 10 minutes, subsequent centrifugation of the supernatant at 4000 rpm for 10 minutes, followed by filtration (0.2 µm). The cleared supernatant was applied to a column filled with a zinc chloride loaded chelating gel (Fractogel EMD Chelate; Merck, Darmstadt, Germany) for immobilized metal affinity chromatography (IMAC) capture.

After sample loading, the remaining cell culture supernatant was washed out and after a pre-elution step the 6×His tagged M2e/CD3 bispecific antibodies were eluted by applying a buffer containing 500 mM imidazol (Merck, Darmstadt, Germany).

The eluted volume containing the M2e/CD3 bispecific antibody was concentrated to a volume of 3 ml using a Vivaspin 20 ultrafiltration unit (Sartorius, Goettingen, Germany) and subsequently run on a Superdex S200 (GE Healthcare, Munich, Germany) size exclusion chromatography (SEC) column to separate the monomeric antibody protein from the dimeric form and other proteins.

Fractions containing the monomeric antibody protein were pooled and protein concentration was determined by measurement of optical absorption at 280 nm wavelength and 1 cm lightpath length and multiplication with the protein sequence specific absorption factor.

4. Identification of Functional M2e-Specific Recombinant Bispecific Single Chain Antibodies Binding of the murM2e-hBiTE was tested by flow cytometry on Influenza A M2 transfected chinese hamster ovary (CHO) cells.

For flow cytometry $2.5 \times 10^5$ cells were incubated with 5 µg/ml of the purified construct in 50 µl PBS with 2% FCS. The binding of the constructs was detected with an anti-His antibody (Penta-His Antibody, BSA free, Qiagen GmbH, Hilden, Germany) at 2 µg/ml in 50 µl PBS with 2% FCS. As a second step reagent a R-Phycoerythrin-conjugated affinity purified F(ab')2 fragment, goat anti-mouse IgG (Fc-gamma fragment specific), diluted 1:200 in 50 µl PBS with 2% FCS (Dianova, Hamburg, Germany) was used. The samples were measured on a FACSCalibur (BD biosciences, Heidelberg, Germany).

CD3 binding was confirmed by flowcytometry as described in the foregoing paragraph on the human T cell line HPB-ALL. For bispecific single chain antibodies possessing a mouse CD3 binding moiety instead of the human CD3 binding moiety, binding was confirmed by flowcytometry as described in the foregoing paragraph on the murine T cell line CTLL-2.

5. Generation of Human-Like Equivalents of the Non-Human M2e Specific Recombinant Bispecific Single Chain Antibody The VH region of the murine anti-M2e recombinant bispecific single chain antibody was aligned against human antibody germline amino acid sequences. The human antibody germline VH sequence was chosen which has the closest homology to the non-human VH and a direct alignment of the two amino acid sequences was performed. There were a number of framework residues of the non-human VH that differ from the human VH framework regions ("different framework positions").

To construct a library that contains the murine CDRs and at every framework position that differs from the chosen human VH sequence both possibilities (the human and the maternal murine amino acid residue), degenerated oligonucleotides were synthesized. These oligonucleotides incorporate at the differing positions the human residue with a probability of 75% and the murine residue with a probability of 25%. For one human VH e.g. six of these oligonucleotides had to be synthesized that overlap in a terminal stretch of approximately 20 nucleotides. To this end every second primer was an antisense primer. Restriction sites needed for later cloning within the oligonucleotides were deleted.

These primers may have a length of 60 to 90 nucleotides, depending on the number of primers that were needed to span over the whole variable (V) sequence.

These e.g. six primers were mixed in equal amounts (e.g. 1 μl of each primer (primer stocks 20 to 100 μM) to a 20 μl PCR reaction) and added to a PCR mix consisting of PCR buffer, nucleotides and Taq polymerase. This mix was incubated at 94° C. for 3 minutes, 65° C. for 1 minute, 62° C. for 1 minute, 59° C. for 1 minute, 52° C. for 1 minute, 50° C. for 1 minute and at 72° C. for 10 minutes in a PCR cycler. Subsequently the product was run in an agarose gel electrophoresis and the product of a size from 200 to 400 isolated from the gel according to standard methods.

This PCR product was then used as a template for a standard PCR reaction using primers that incorporate N-terminal and C-terminal suitable cloning restriction sites. The DNA fragment of the correct size (for a VH approximately 350 nucleotides) was isolated by agarose gel electrophoresis according to standard methods. In this way sufficient VH DNA fragment was amplified. This VH fragment was now a pool of VH fragments that have each one a different amount of human and murine residues at the respective differing framework positions (pool of human-like VH).

The same procedure was performed for the VL region of the murine anti-M2e recombinant bispecific single chain antibody (pool of human-like VL).

The pool of human-like VH was then combined with the murine VL and the pool of human-like VL was combined with the murine VH in the phage display vector pComb3H5Bhis to form two libraries of functional partly human-like scFvs from which—after display on filamentous phage—anti-M2e binders were selected, screened, identified and confirmed as described in Example 4. After screening, as described in Example 6, single clones were analyzed for favorable properties and amino acid sequence. Those scFvs which contained a human-like VH or a human-like VL which were closest in amino acid sequence homology to human germline V-segments were preferred. After further characterization, as described in Patent Application No. US 2011/0293619, human-like VH and human-like VL from partly human-like anti-M2e scFvs were converted into 9 different human-like recombinant bispecific single chain antibodies (SEQ ID NOs: 14, 22, 30, 38, 46, 54, 62, 70, and 78).

6. Screening for Partly Human-Like scFvs Binding to M2e

Plasmid DNA corresponding to 4 rounds of panning was isolated from *E. coli* cultures after selection. For the production of soluble scFv-protein, VH-VL-DNA fragments were excised from the plasmids (XhoI-SpeI). These fragments were cloned via the same restriction sites in the plasmid pComb3H5BFlag/His differing from the original pComb3H5BHis in that the expression construct (e.g. scFv) includes a Flag-tag (TGD YKDDDDK) between the scFv and the His6-tag and the additional phage proteins were deleted. After ligation, each pool (human-like VH×murine VL and murine VH×human-like VL) of plasmid DNA was transformed into 100 μl heat shock competent *E. coli* TG1 and plated onto carbenicillin LB-agar. Single colonies were picked into 200 μl of LB carb (50 μg/ml).

*E. coli* transformed with pComb3H5BHis containing a VH- and VL-segment produce soluble scFv in sufficient amounts after excision of the gene III fragment and induction with 1 mM IPTG. Due to a suitable signal sequence, the scFv-chain was exported into the periplasm where it folds into a functional conformation.

Single *E. coli* TG1 bacterial colonies from the transformation plates were picked for periplasmic small scale preparations and grown for 6 hours at 37° C. in LB-medium (e.g. 10 ml) supplemented with 50 μg/ml carbenicillin and 0.1% glucose. After the 6 hours incubation time, IPTG was added to a final concentration of 1 mM, followed by overnight incubation at 30° C. After centrifugation, the bacterial pellets were dissolved in PBS (e.g. 1 ml). By four rounds of freezing at −70° C. and thawing at 37° C., the outer membrane of the bacteria was destroyed by temperature shock and the soluble periplasmic proteins including the scFvs were released into the supernatant. After elimination of intact cells and cell-debris by centrifugation, the supernatant containing the partly human-like anti-M2e-scFvs was collected and used for further examination.

Binding of the partly human-like scFvs was tested by flow cytometry on Influenza A M2 transfected chinese hamster ovary (CHO) cells (as described in Example 1).

For flow cytometry $2.5 \times 10^5$ cells were incubated with 50 μl of the periplasm preparation (as described above). The binding of the constructs was detected with an anti-Flag antibody (Monoclonal anti-FLAG M2 antibody produced in mouse, Sigma-Aldrich, Hamburg, Germany) at 0.5 μg/ml in 50 μl PBS with 2% FCS. As a second step reagent a R-Phycoerythrin-conjugated affinity purified F(ab')2 fragment, goat anti-mouse IgG (Fc-gamma fragment specific), diluted 1:200 in 50 μl PBS with 2% FCS (Dianova, Hamburg, Germany) was used. The samples were measured on a FACSCanto II (BD biosciences, Heidelberg, Germany).

ScFv clones which showed the strongest binding on M2 expressing CHO cells and did not bind to untransfected CHO cells (both based on the fluorescence signal in the flow cytometric analysis as described above) were sequenced and further characterized as described in Patent Application No. US 2011/0293619.

7. Affinity Measurement

The "affinity" or "binding affinity" $K_D$ can be determined by a cell-based assay, in which cells that naturally express the antigen or are transfected with a plasmid encoding the antigen, are incubated with different concentrations of the monomeric bispecific antibody and after a washing step are stained with a His-tag specific Fab fragment covalently linked to a fluorescent stain, e.g. fluorescein isothiocyanate (FITC). By this means, only monovalent binding can be observed and no avidity effects do influence the measurement. After another washing step and fixation (to avoid dissociation of bound molecules), the fluorescence can be measured by flow cytometry and $K_D$ values can be calculated using the "one site binding (hyperbola)" equation in a statistics software (e.g. Graphpad Prism). The procedure for the affinity measurements of M2e/CD3 bispecific antibody constructs is described in the following.

To calculate the affinities of the M2e/CD3 bispecific antibodies, a cell-based assay was performed. A 1:2 or 1:3 serial dilution of M2e/CD3 bispecific antibodies in FACS buffer (PBS/1% FCS/0.05% sodium azide) was prepared starting at a concentration of 94 nM. On a 96 well v-bottom plate $1 \times 10^4$ M2 expressing CHO cells (as described above) per well were incubated with 50 μl of the different dilutions of M2e/CD3 bispecific antibody for 4 hours at 4° C. to allow the establishment of an equilibrium of bound and unbound antibody molecules at every respective concentration. As blank value, cells were incubated in FACS buffer without the addition of the M2e/CD3 bispecific antibody. After one washing step with FACS buffer, the cells were incubated with 50 μl of anti-His Fab fragments, derived from a monoclonal anti-6×-His antibody (clone AD1.1.10; AbD Serotec, Duesseldorf, Germany), covalently linked to fluorescein isothiocyanate (FITC), at a concentration of 30 μg/ml in FACS buffer for 45 minutes at 4° C. After another washing step with FACS buffer, the cells were fixed with 2% paraformaldehyde (PFA) in FACS buffer for 15 minutes at 4° C., centrifuged and resuspended in FACS buffer and subsequently measured at a FACSCanto II (BD biosciences, Heidelberg, Germany). The measurement was performed in triplicates for every M2e/CD3 antibody concentration used. Analysis of the results was carried out with Prism 5 for Windows (GraphPad Software Inc., San Diego, Calif., USA) using the "one site binding (hyperbola)" equation.

Figure 2:
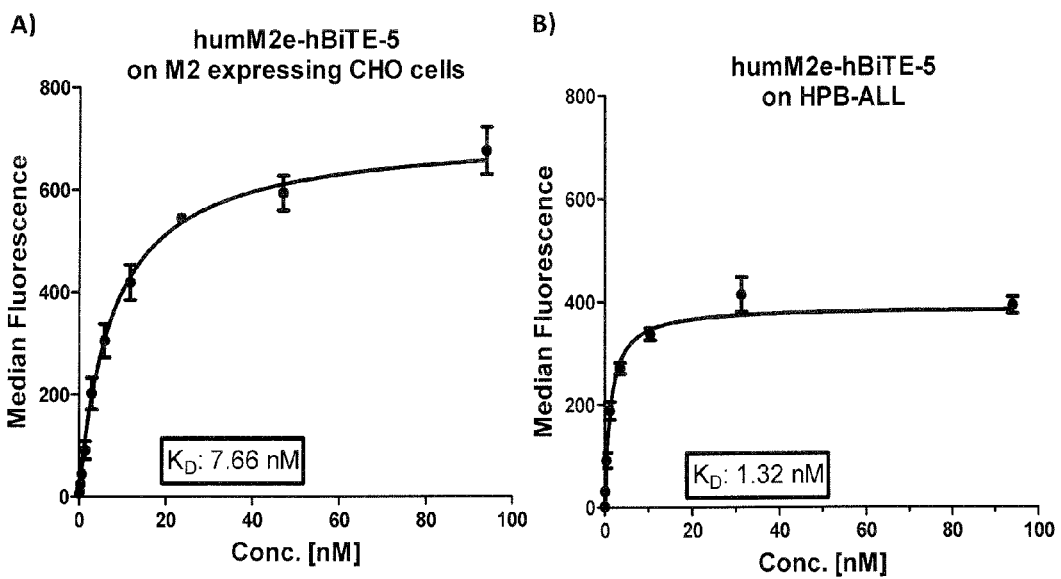
FIG. 2:
Affinity measurements of an exemplary humM2e-hBiTE. The $K_D$ value of humM2e-hBiTE (A) is lower compared to the murM2e-hBiTE (depicted in FIG. 1A) for the binding on M2 expressing CHO cells. The binding of human CD3, expressed by HPB-ALL cells, is unaffected by the different M2e binding moieties, see (B) and FIG. 1B. The median values of 3 measurements+1-SEM are shown.

Surprisingly, the human-like M2e-hBiTEs (humM2e-hBiTEs) show significantly higher affinities to M2e with $K_D$ values approximately 5.7 times lower compared to the murM2e-hBiTE, as shown for an exemplary humM2e-hBiTE in FIG. 2.

8. Cytotoxic Activity

FACS-Based Cytotoxicity Assay with Unstimulated Human T-Cells

PBMCs were isolated from human blood by density gradient centrifugation using Biocoll (Biochrom AG, Berlin, Germany). After isolation, the PBMCs were washed twice with 50 ml PBS and depletion of $CD14^+$ and $CD56^+$ cells was performed using CD14 and CD56 MicroBeads (Miltenyi Biotec GmbH, Bergisch Gladbach, Germany) according to the manufacturer's instructions. $CD14^+/CD56^+$ cells were resuspended in RPMI 1640 with stabilized glutamine/10% FCS and subsequently used as effector cells.

Influenza A M2 transfected CHO target cells (as described above) were washed twice with PBS/2% FCS and labeled with 5 μl Vybrant DiO (Life Technologies GmbH, Darmstadt, Germany) per $1 \times 10^6$ cells in RPMI (as above) at a final concentration of $1.25 \times 10^5$ cells per ml for 3 minutes at 37° C. Subsequently, the labeled target cells were washed twice with 25 ml RPMI and then used in the cytotoxicity assay.

The assay was performed in a 96-well plate in a total volume of 200 μl supplemented RPMI (as above) with an effector:target (E:T) ratio of 10:1. A starting concentration of 1.67-5 μg/ml of purified bispecific antibody and threefold dilutions thereof were used. Incubation time for the assay was 66 hours. After the incubation, the cells were resuspended and transferred into a new 96 well plate. Adhering target cells were trypsinized for 5 minutes at 37° C., resuspended in PBS/2% FCS and combined with the other cells from the respective wells. The plates were centrifuged for 4 minutes at 1200 rpm, the supernatant was discarded and the cells were resuspended in PBS plus 2% FCS plus 1 μg/ml propidium iodide (PI; Sigma-Aldrich, Munich, Germany). Cytotoxicity was determined as percentage of DiO/PI double positive cells relative to the overall number of DiO positive cells as determined by flow cytometry using a FACSCanto II (BD Biosciences, Heidelberg, Germany). All measurements were carried out in duplicates. Analysis of the results was carried out with Prism 5 for Windows (version 5.03, GraphPad Software Inc., San Diego, Calif., USA).

Figure 3:
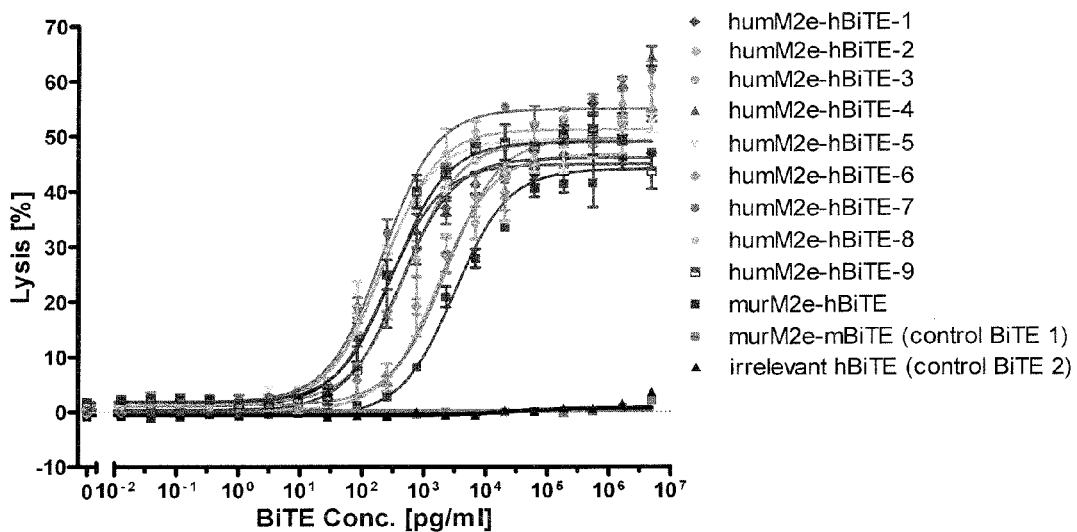
FIG. 3.

The results for the kill of M2 expressing target cells are shown in FIG. 3. All humM2e-hBiTEs show lower $EC_{50}$ values and thus a higher cytotoxic activity compared to the murM2e-hBiTE.

9. In Vivo Validation

For the in vivo validation in an Influenza A mouse model, a murine and a human-like M2e-mBiTE (murM2e-mBiTE and humM2e-mBiTE) were used, in which the human CD3 binding moiety was replaced by a murine CD3 binding moiety (SEQ ID NO: 88) as described in Example 1. The human CD3 binding bispecific antibodies (murM2e-hBiTE and humM2e-hBiTE) served as negative controls, the parental monoclonal murine anti-M2e antibody the served as positive control.

To induce a pool of memory T cells, which are important for effective M2e/CD3 bispecific antibody-induced killing of target cells, SPF-housed female BALB/c mice of 7-8 weeks of age were first infected with a sublethal dose (0.2 $LD_{50}$) of Influenza B virus (B/Memphis/10/97) prior to the Influenza A virus challenge. Influenza B infection does not induce any cross-protection against Influenza A virus infection. After five weeks, when the mice had completely recovered from the influenza B infection, they were intranasally infected with 2 $LD_{50}$ of mouse-adapted Influenza A/X47 (H3N2) virus. Treatment with the M2e/CD3 bispecific antibody or the parental murine monoclonal antibody (M2emAb) was performed by intravenous injection of 10 μg M2e/CD3 bispecific antibody or 15 μg M2emAb (equimolar) per dose per mouse diluted in PBS, from days 1 through 6 after virus challenge. Five groups, each comprising six mice, were used, and received the treatment listed in Table 2.

Figure 4:
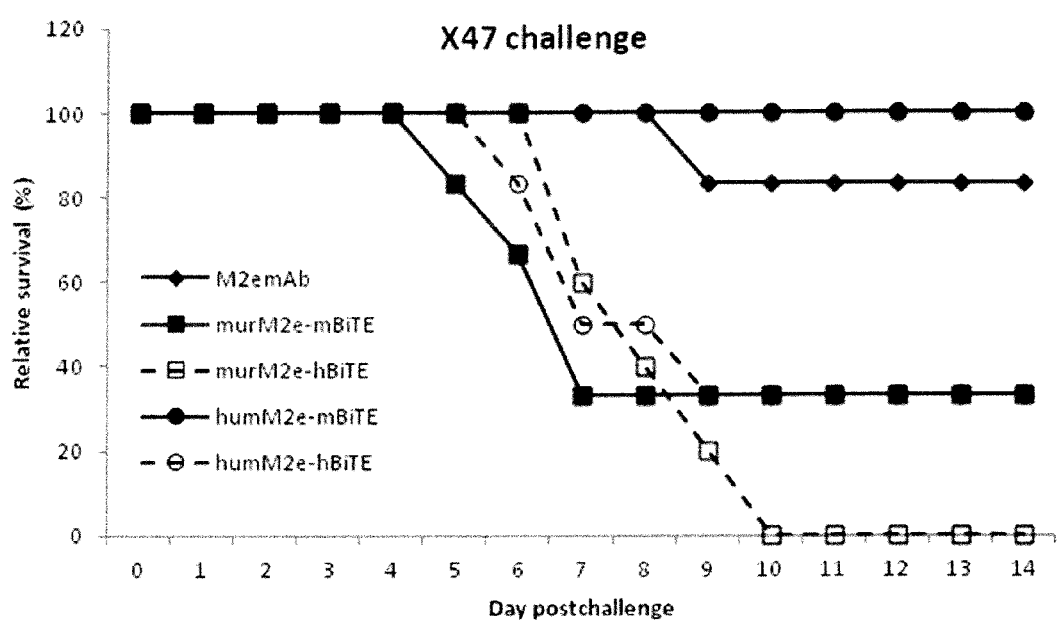

The results of the experiment are shown in FIG. 4. All mice that received humM2e-mBiTE survived the experiment whereas only 30% of the mice receiving murM2e-mBiTE (possessing identical CDR sequences) survived.

TABLE 2

Groups of mice used for the in vivo validation

| Group | Treatment |
|---|---|
| 1 | M2emAb |
| 2 | murM2e-mBiTE |
| 3 | murM2e-hBiTE |
| 4 | humM2e-mBiTE |
| 5 | humM2e-hBiTE |

10. In Vivo Validation of hM2e-mBITEs Against Tamiflu-Sensitive or Resistant Influenza Strains Oseltamivir (commercial name Tamiflu) has been widely used to treat or to prevent influenza infection. Tamiflu is a neuraminidase-inhibitor which has a wide spectrum of activity, inhibiting all or nearly all influenza A and B-strains of influenza. In the last few years, however, Tamiflu-resistant influenza strains have emerged in several locations, even in countries where Tamiflu had never been used.

To demonstrate the potential of hM2e-mBiTEs against Tamiflu resistant strains the following mouse model was used:

Experimental Setup:

To induce a pool of memory T-cells, SPF-housed female BALB/c mice, aged 7-8 weeks, (n=12 per group) were pre-exposed to a sublethal dose (0.1 $LD_{50}$) of the influenza B virus B/Memphis/10/97. After this pretreatment (8 weeks for recovery from influenza B infection), mice were challenged with a potentially lethal dose (2 $LD_{50}$) of a mouse-adapted H5N1 strain that carries the H274Y mutation in the neuraminidase gene, rendering this virus strain resistant to Tamiflu-treatment. Subsequently, the mice were treated with hM2e-mBiTEs or hM2e-hBiTEs. As a control in this experiment 2 additional groups were included that received either hM2e-mBiTEs or hM2e-hBiTEs after an X47 challenge. All treatments were performed in a therapeutic setting with daily treatments starting 1 day after challenge until day 6 after challenge. hM2e-mBiTE and hM2e-hBiTE were administered intravenously at a dose of 10 μg per mouse per day (in a total volume of 100 μL). The body weight and survival of the mice was monitored daily for 14 days after challenge.

An overview of viruses used for challenge and of accompanying treatments is provided in the table below:

| No | n = | Challenge virus | Treatment |
|---|---|---|---|
| 1 | 12 | H5N1 H274Y | hM2e-mBiTE |
| 2 | 12 | H5N1 H274Y | hM2e-mBiTE |
| 3 | 6 | X47 | hM2e-mBiTE |
| 4 | 6 | X47 | hM2e-mBiTE |

Virus Strains Used for Challenge:

Mice were challenged intranasally with 2 $LD_{50}$ of the following virus strains: (all strains were mouse-adapted)

1. H5N1 H274Y: Tamiflu-resistant. This is a 6:1:1 reassortant virus in the A/PR8 background carrying the HA (lacking the poly-basic cleavage site) and NA of A/crested eagle/Belgium/01/2004 (H5N1, clade 1). To render the virus resistant to Tamiflu, the H274Y mutation was introduced in the NA gene sequence (this is the mutation most often observed in virus strains which have become Tamiflu-resistant in the field).
2. Mouse adapted X47: This is a 6:2 recombinant virus in the A/Puerto Rico/8/34 (H1N1) background carrying the HA and NA of A/Victoria/3/75 (H3N2).

The results of the experiment are shown in FIG. 5. Mice treated with hM2e-mBiTEs after infection survived a potentially lethal X47 challenge although morbidity was only partially repressed. However, there was clearly a faster recovery of body weight in the hM2e-mBiTE treated mice relative to the control (hM2e-hBiTE treated) group, especially on day 8 and 9 after challenge.

All mice challenged with H5N1 H274Y (tamiflu resistant) influenza strain followed by hM2e-mBiTEs treatment survived.

LITERATURE

De Filette, M., W. Martens, K. Roose, T. Deroo, F. Vervalle, M. Bentahir, J. Vandekerckhove, W. Fiers and X. Saelens (2008). "An influenza A vaccine based on tetrameric ectodomain of matrix protein 2." *J Biol Chem* 283(17): 11382-11387.

Groves, M. A. and J. K. Osbourn (2005). "Applications of ribosome display to antibody drug discovery." *Expert Opin Biol Ther* 5(1): 125-135.

Lipovsek, D. and A. Pluckthun (2004). "In-vitro protein evolution by ribosome display and mRNA display." *J Immunol Methods* 290(1-2): 51-67.

Mack, M., G. Riethmuller and P. Kufer (1995). "A small bispecific antibody construct expressed as a functional single-chain molecule with high tumor cell cytotoxicity." *Proc Natl Acad Sci USA* 92(15): 7021-7025.

Schotsaert, M., M. De Filette, W. Fiers and X. Saelens (2009). "Universal M2 ectodomain-based influenza A vaccines: preclinical and clinical developments." *Expert Rev Vaccines* 8(4): 499-508.

| SEQ ID NO: | Designation | Type | Sequence |
|---|---|---|---|
| 1 | CDR-H1 of Anti-M2e | AA | TYAMS |
| 2 | CDR-H2 of Anti-M2e | AA | SMSSGGSLYYPDTVKG |
| 3 | CDR-H3 of Anti-M2e | AA | GGYGTSY |
| 4 | CDR-L1 of Anti-M2e | AA | RSSQSIVHSIGDTYLE |
| 5 | CDR-L2 of Anti-M2e | AA | KVSNRFS |
| 6 | CDR-L3 of Anti-M2e | AA | FQGSHFPYT |
| 7 | VH of humM2e-hBiTE-1 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATGAGTAGTGGTGGTAGTCTTTATTATCCAGACACTGTGAAGGGCCGA TTCACCATCTCCAGAGATAATTCCAAGAACACTGTGTACCTGCAAATGAACAGTCTGAGGGCTGAGGACACGGCCATGTATTACTGTGTAAGAGGAGGC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCCTGTCTGTCACTCCTGGAGAACCGGCCTCCATCTCTTGCAGATCTAGTCAGAGCATTGTTCATAGTATTGGAGAC ACCTATTTAGAATGGTACCTGCAGAAACCAGGCCAGTCTCCACAGCTCCTGATCTACAAAGTTTCCAACCGATTTTCTGGGGTCCCAGACAGGTTCAGT GGCAGTGGATCAGGGACAGATTTCACACTCAAGATCAGCAGAGTGGAGGCTGAGGATGTGGGAATTTATTACTGCTTTCAAGGTTCACATTTCCCGTAC ACGTTCGGACAGGGGACCAAGCTGGAAATAAAA |
| 8 | VH of humM2e-hBiTE-1 | AA | EVQLVESGGGLVQPGGSLRLSCAASGFTVSTYAMSWVRQTPEKRLEWVASMSSGGSLYYPDTVKGRFTISRDNSKNTVYLQMNSLRAEDTAMYYCVRGG YGTSYWGQGTLVTVSS |
| 9 | VL of humM2e-hBiTE-1 | NT | GACATCGTGATGACCCAAACTCCACTCTCCCTGTCTGTCACTCCTGGAGAACCGGCCTCCATCTCTTGCAGATCTAGTCAGAGCATTGTTCATAGTATT GGAGACACCTATTTAGAATGGTACCTGCAGAAACCAGGCCAGTCTCCACAGCTCCTGATCTACAAAGTTTCCAACCGATTTTCTGGGGTCCCAGACAGG TTCAGTGGCAGTGGATCAGGGACAGATTTCACACTCAAGATCAGCAGAGTGGAGGCTGAGGATGTGGGAATTTATTACTGCTTTCAAGGTTCACATTTC CCGTACACGTTCGGACAGGGGACCAAGCTGGAAATAAAA |
| 10 | VL of humM2e-hBiTE-1 | AA | DIVMTQTPLSLSVTPGEPASISCRSSQSIVHSIGDTYLEWYLQKPGQSPQLLIYKVSNRFSGVPDRFSGSGSGTDFTLKISRVEAEDVGIYYCFQGSHF PYTFGQGTKLEIK |

| SEQ ID NO: | Designation | Type | Sequence |
|---|---|---|---|
| 11 | VH-VL of humM2e-hBiTE-1 | NT | GAGGTGCAGCTGGTCGAGTCTGGGGGAGGCTTAGTGCAGCCTGGAGGGTCCCTGAGACTCTCCTGTGCAGCCTCTGAGATTCACTGTGAGTACTTATGCC ATGTCTTGGGTTCGCCAGACTCCAGAGAAGAGGCTGGAATGGGTCGCATCCATGAGTAGTGGTGGTAGTGATATTCCAGACACTGTGAAGGGCCGA TTCACCATCTCCAGAGATAATTCCAAGAACACCGTGTACCTGCAAATGAACAGTCTGAGGGCTGAGGACACGGCCATGTATTACTGTGTAAGAGGAGGC TACGGAACTTCGTACTGGGGCCAAGGGACCCTGGTCACCGTCTCCAGTGGTGGTGGTGGTTCTGGCGGCGGTGGCTCGGGTGGTGGTGGTTCTGACATC GTGATGACCCAAACTCCACTCTCCCTGCCTGTCACACTGGAGGACCCGGCTCTCCTGCAGTCTCCACAGGTCTCCTGATCTACAAAGTTTCCAACCGATTCTCTGGGGTCCAGACAGTTCAGT GGCAGTGGATCAGGGACACAGATTTCACACTCAAGATCAGCAGAGTGGAGGCTGAGGATGTGGGAGTTTATTACTGCTTTCAAGGTTCACATTTCCCGTAC ACGTTCGGACAGGGGACCAAGCTGGAAATAAAA |
| 12 | VH-VL of humM2e-hBiTE-1 | AA | EVQLVESGGGLVQPGGSLRLSCAASGFTVSTYAMSWVRQTPEKRLEWVASMSSGGSDIVMTQTPLSLSVTPGEPASISCRSSQSIVHSIGDTYLEWYLQKPGQSPQLLIYKVSNRFSGVPDRFS GYGTSYWGQGTLVTVSSGGGGSGGGGSGGGGSDIVMTQTPLSLPVTLGEPASISCRSSQSIVHSIGDTYLEWYLQKPGQSPQLLIYKVSNRFSGVPDRFS GSGSGTDFTLKISRVEAEDVGIYYCFQGSHFPYTFGQGTKLEIK |
| 13 | VH-VL of humM2e-hBiTE-1 × anti-CD3 | NT | GAGGTGCAGCTGGTCGAGTCTGGGGGAGGCTTAGTGCAGCCTGGAGGGTCCCTGAGACTCTCCTGTGCAGCCTCTGAGATTCACTGTGAGTACTTATGCC ATGTCTTGGGTTCGCCAGACTCCAGAGAAGAGGCTGGAATGGGTCGCATCCATGAGTAGTGGTGGTAGTGATATTCCAGACACTGTGAAGGGCCGA TTCACCATCTCCAGAGATAATTCCAAGAACACCGTGTACCTGCAAATGAACAGTCTGAGGGCTGAGGACACGGCCATGTATTACTGTGTAAGAGGAGGC TACGGAACTTCGTACTGGGGCCAAGGGACCCTGGTCACCGTCTCCAGTGGTGGTGGTGGTTCTGGCGGCGGTGGCTCGGGTGGTGGTGGTTCTGACATC GTGATGACCCAAACTCCACTCTCCCTGCCTGTCACACTGGAGGACCCGGCTCTCCTGCAGTCTCCACAGGTCTCCTGATCTACAAAGTTTCCAACCGATTCTCTGGGGTCCAGACAGTTCAGT GGCAGTGGATCAGGGACACAGATTTCACACTCAAGATCAGCAGAGTGGAGGCTGAGGATGTGGGAGTTTATTACTGCTTTCAAGGTTCACATTTCCCGTAC ACGTTCGGACAGGGGACCAAGCTGGAAATAAAATCCGAGGTGCAGCTGGTGCAGTCTGGGGGAGGCTTGGTACAGCCTGGGGGGTCCCTGAGACTCTCC TCATTGAAACTCTATGTGCAGCCTGGATTCACCTTCAGTGGAAGCTACACCATGAGCTGGGTCCGCCAGGCTCCAGGGAAAGGTTTGGAATGGGTTGCT CGCATAAGAAGTAAATATAATAATTATGCCACATACTATGCCGATTCAGTGAAAGGCAGGTTCACCATCTCCAGAGATAATTCCAAGAACACTGGGGCTTACCTG CAAATGAACTCTCTGAGAGCTGAGGACACGGCGGTGTATTACTGTGTAAGACATGGAAACTTCGGTAATAGCTACATATCCTACTGGGCTTACTGG GGCCAAGGGACTCTGGTCACCGTCTCACCTCAGATCCAGTTGGTCCCGGCGCTCCAGCGCTCCCAGCCCAAGTTTTCTGCCCCGTGATCTTCACCTGGCCACACACCTCTGTCTCCACACACCTCAGGTCGTGTTACGCTATCGGGCCTTGTACCTGCAACCCTGGGTGTTCCGTGACGAGGAACCAACTCTGACT CCAGGTCAGGCACCTCAGGGCTGCTATACGCCAGAGGATGAGGCAGAATATTACTGTGTTCTATGGTACAGCAACAGATGGGTATCTCAGCGCTGCC GTCCTACATCATCACCATCAT |
| 14 | VH-VL of humM2e-hBiTE-1 × anti-CD3 | AA | EVQLVESGGGLVQPGGSLRLSCAASGFTVSTYAMSWVRQTPEKRLEWVASMSSGGSDIVMTQTPLSLSVTPGEPASISCRSSQSIVHSIGDTYLEWYLQKPGQSPQLLIYKVSNRFSGVPDRFS GYGTSYWGQGTLVTVSSGGGGSGGGGSGGGGSDIVMTQTPLSLPVTLGEPASISCRSSQSIVHSIGDTYLEWYLQKPGQSPQLLIYKVSNRFSGVPDRFS GSGSGTDFTLKISRVEAEDVGIYYCFQGSHFPYTFGQGTKLEIKSSGGGGSEVQLVESGGGLVQPGGSLKLSCAASGFTFNKYAMNWVRQAPGKGLEWVA RIRSKYNNYATYYADSVKDRFTISRDDSKNTAYLQMNNLKTEDTAVYYCVRHGNFGNSYISYWAYWGQGTLVTVSSGGGGSGGGGSQTVVTQEP SLTVSPGGTVTLTCCSSTGAVTSGNYPNWVQQKPGQAPRGLIGGTKFLAPGTPARFSGSLLGKAALTLSGVQPEDEAEYYCVLWYSNRWVFGGGTKLT VLHHHHHH |
| 15 | VH of humM2e-hBiTE-2 | NT | GAGGTGCAGCTGGTCGAGTCTGGGGGAGGCTTAGTGCAGCCTGGAGGGTCCCTGAGACTCTCCTGTGCAGCCTCTGAGATTCACTGTGAGTACTTATGCC ATGTCTTGGGTTCGCCAGACTCCAGAGAAGAGGCTGGAATGGGTCGCATCCATGAGTAGTGGTGGTAGTGATATTCCAGACACTGTGAAGGGCCGA TTCACCATCTCCAGAGATAATTCCAAGAACACCGTGTACCTGCAAATGAACAGTCTGAGGGCTGAGGACACGGCCATGTATTACTGTGTAAGAGGAGGC TACGGAACTTCGTACTGGGGCCAAGGGACCCTGGTCACCGTCTCA |
| 16 | VH of humM2e-hBiTE-2 | AA | EVQLVESGGGLVQPGGSLRLSCAASGFTVSTYAMSWVRQTPEKRLEWVASMSSGGSDIVMTQTPLSLSVTPGEPASISCRSSQSIVHSIGDTYLEWYLQKPGQSPQLLIYKVSNRFSGVPDRFS YGTSYWGQGTLVTVSS |
| 17 | VL of humM2e-hBiTE-2 | NT | GACATCGTGATGACCCAAACTCCACTCTCCCTGTCTGTCACTCCTGGAGAACCGGCCTCCATCTCTTGCAGATCTAGTCAGAGCATTGTTCATAGTATT GGAGACACCTATTTAGAATGGTACCTGCAGAAACCAGGCCAGTCTCCACAGCTCCTGATCTACAAAGTTTCCAACCGATTTTCTGGGGTCCCAGACAGG TTCAGTGGCAGTGGATCAGGGACAGATTTCACACTCAAGATCAGCAGAGTGGAGGCTGAGGATGTGGGAGTTTATTACTGCTTTCAAGGTTCACATTTC CCGTACACGTTCGGACAGGGGACCAAGCTGGAAATAAAA |

-continued

| SEQ ID NO: | Designation | Type | Sequence |
|---|---|---|---|
| 18 | VL of humM2e-hBiTE-2 | AA | DIVMTQTPLSLSVTPGEPASISCRSSQSIVHSIGDTYLEWYLQKPGQSPQLLIYKVSNRFSGVPDRFSGSGSGTDFTLKISRVEAEDVGVYYCFQGSHFPYTFGQGTKLEIK |
| 19 | VH-VL of humM2e-hBiTE-2 | NT | GAGGTGCAGCTGGTCGAGTCTGGGGGAGGCTTAGTGCAGCCTGGAGGGTCCCTGAGACTCTCCTGTGCAGCCTCTGGATTCACTGAGTACTTATGCCATGTCTTGGGTTCGCCAGACTCCAGAGATAATTCCAGAGGGTCTGAGTGGTCAGTAGTAGTGGTGGTAGTAGTACTTATTATGCAGACACTGTGAAGGGCCGATTCACCATCTCCAGAGACAATGTCAAGAACACCCTGTACCTGCAAATGAACAGTCTGAGGGCTGAGGACACGGCCATGTATTACTGTGTAAGAGAGGCATACGGAAACTTCGATCTGGGGCCAAGGGACCCTGGTCACCGTCTCCTCAGGTGGTGGTGGTTCTGGTGGTGGTGGTTCTGACATCGTGATGACCCAAACTCCACTCTCCCTGCCTGTCACCCCTGGAGAACCGGCCTCCATCTCTTGCAGATCTAGTCAGAGTATTGTTCATAGTATTGGAGACACCTATTTAGAATGGTACCTTCAGAAACCAGGCCAGTCTCCACAGCTCCTGATCTACAAAGTTTCCAACCGATTTTCTGGGGTCCCAGACCAGTTCAGTGGCAGTGGATCAGGGACAGATTTCACACTCAAGATCAGCAGAGTGGAGGCTGAGGATCTGGGAGTTTATTACTGCTTTCAAGGTTCACATTTCCCGTACACGTTCGGACAGGGGACCAAGCTGGAAATAAAA |
| 20 | VH-VL of humM2e-hBiTE-2 | AA | EVQLVESGGGLVQPGGSLRLSCAASGFTVSTYAMSWVRQTPEKKRLEWVASMSSGGSLYYPDTVKGRFTISRDNSKNTVVLQMNSLRAEDTAMYCVRGGYGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFSGSGSGTDFTLKISRVEAEDVGVYYCFQGSHFPYTFGQGTKLEIK |
| 21 | VH-VL of humM2e-hBiTE-2 x anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGAGTACTTATGCCATGTCTTGGGTTCGCCAGACTCCAGAGATAATTCCAGAGGGTCTGAGTGGTCAGTAGTAGTGGTGGTAGTAGTACTTATTATGCAGACACTGTGAAGGGCCGATTCACCATCTCCAGAGACAATGTCAAGAACACCCTGTACCTGCAAATGAACAGTCTGAGGGCTGAGGACACGGCCATGTATTACTGTGTAAGAGAGGCATACGGAAACTTCGATCTGGGGCCAAGGGACCCTGGTCACCGTCTCCTCAGGTGGTGGTGGTTCTGGTGGTGGTGGTTCTGACATCGTGATGACCCAAACTCCACTCTCCCTGCCTGTCACCCCTGGAGAACCGGCCTCCATCTCTTGCAGATCTAGTCAGAGTATTGTTCATAGTATTGGAGACACCTATTTAGAATGGTACCTTCAGAAACCAGGCCAGTCTCCACAGCTCCTGATCTACAAAGTTTCCAACCGATTTTCTGGGGTCCCAGACCAGTTCAGTGGCAGTGGATCAGGGACAGATTTCACACTCAAGATCAGCAGAGTGGAGGCTGAGGATCTGGGAGTTTATTACTGCTTTCAAGGTTCACATTTCCCGTACACGTTCGGACAGGGGACCAAGCTGGAAATCAAAGGTGGTGGTGGTTCAGGCGGAGGTGGCTCTGGCGGTGGCGGATCGGAGGTTCAGCTGGTGGAGTCTGGCGGTGGCCTGGTGCAGCCAGGGGGCTCACTCCGTTTGTCCTGTGCAGCTTCTGGCTTCAACATTAAAGACACCTATATACACTGGGTACGTCAGGCCCCGGGTAAGGGCCTGGAATGGGTTGCACGTATTTATCCAACAAATGGGTATACTAGATATGCCGATAGCGTCAAGGGCCGTTTCACTATAAGCGCAGACACATCCAAAAACACAGCCTACCTGCAAATGAACAGCCTGCGTGCTGAGGACACTGCCGTCTATTATTGTGCTAGATGGGGTTACTATGGTAGTCCCTTGGACTACTGGGGTCAAGGAACCCTGGTCACCGTCTCGAGTGGTGGTGGTGGTTCGGGCGGCGGTGGCTCCGGCGGTGGCGGATCGGACATCCAGCTGACCCAGTCCCCCGCCATCATGAGTGCCAGTCCTGGGGAGAAGGTCACCATGACCTGCAGTGCCAGCTCAAGTGTAAGTTACATGAACTGGTACCAGCAGAAGTCAGGCACCTCCCCCAAAAGATGGATTTATGACACATCCAAACTGGCTTCTGGAGTCCCTGCTCACTTCAGGGGCAGTGGGTCTGGGACCTCTTACTCTCTCACAATCAGCGGCATGGAGGCTGAAGATGCTGCCACTTATTACTGCCAGCAGTGGAGTAGTAACCCCCTCACGTTCGGTGCTGGGACCAAGCTGGAGCTGAAACGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTCATCATCACCATCATCAT |
| 22 | VH-VL of humM2e-hBiTE-2 x anti-CD3 | AA | EVQLVESGGGLVQPGGSLRLSCAASGFTVSTYAMSWVRQTPEKKRLEWVASMSSGGSLYYPDTVKGRFTISRDNSKNTVVLQMNSLRAEDTAMYCVRGGYGTSYWGQGTLVTVSSGGGGSGGGGSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLHHHHHH |
| 23 | VH of humM2e-hBiTE-3 | NT | GAGGTGCAGCTGGTCGAGTCTGGGGGAGGCTTAGTGCAGCCTGGAGGGTCCCTGAGACTCTCCTGTGCAGCCTCTGGATTCACTGAGTACTTATGCCATGTCTTGGGTTCGCCAGACTCCAGAGATAATTCCAGAGGGTCTGAGTGGTCAGTAGTAGTGGTGGTAGTAGTACTTATTATGCAGACACTGTGAAGGGCCGATTCTTTATTATCCAGAGGTCTGAGTAGTACTGGGCAGACACCCTGGTCACCGTCTCCTCA |
| 24 | VH of humM2e-hBiTE-3 | AA | EVQLVESGGGLVQPGGSLRLSCAASGFTVSTYAMSWVRQTPEKKRLEWVASMSSGGSLYYPDTVKGRFTISRDNSKNTVVLQMNSLRAEDTAMYCVRGGYGTSYWGQGTLVTVSS |

-continued

| SEQ ID NO: | Designation | Type | Sequence |
|---|---|---|---|
| 25 | VL of humM2e-hBiTE-3 | NT | GACATCGTGATGACCCAAACTCCACTCTCCCTGTCTGTCACTCCTGGAGACCGGCCTCCATCTGTGAGATCTAGTCAGAGCATTGTTCATAGTATT GGAGACACCTATTTAGAATGGTACCTGCAGAAACCAGGCCAGTCTCCAAAGCTCCTGATCTACAAAGTTTCACCGATTTCTGGGGTCCCAGACAGG TTCAGTGGCAGTGGATCAGGGACAGATTTCACACTCAAGATCAGCAGAGTGGAGGCTGAGGATCTGGGAGTTTATTACTGCTTTCAAGGTTCACATTC CCGTACACGTTCGGAGGGGGGACCAAGCTGGAAATAAAA |
| 26 | VL of humM2e-hBiTE-3 | AA | DIVMTQTPLSLSVTPGEPASISCRSSQSIVHSIGDTYLEWYLQKPGQSPKLLIYKVSNRFSGVPDRFSGSGSGTDFTLKISRVEAEDVGVYYCFQGSHF PYTFGQGTKLEIK |
| 27 | VH-VL of humM2e-hBiTE-3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATTAGTAGTGGTGGTAGTGGTAGTACCTACTATCCAGACAGTGTAAAGGGCCGA TTCACCATCTCCAGAGATAATTCCAAGAACACCCTGTACCTGCAAATGAACAGTCTGAGGGCTGAGGATATCTGAGGATATCTGTGTGTTCTGACATCAT TACGGAACTTCGTACTGGGGCCAAGGGACCACGGTCACCGTCTCCTCAGGTGGTGGTGGTTCTGGTGGTGGTGGTTCTGGCGGCGGCGGCTCAGGTGGTG GTGATGACCCAAACTCCACTCTCCCTGTCTGCAAACCAGGCCCTCGATCTACAAAGTTTCAACCCGATTTCTGGGGTCCCAGACAGGTTCAGT GGCAGTGGATCAGGGACAGATTTCACACTCAAGATCAGCAGAGTGGAGGCTGAGGATGTGGGAGTTTATTACTGCTTTCAAGGTTCACATTCCCGTAC ACGTTCGGACAGGGGGACCAAGCTGGAAATAAAA |
| 28 | VH-VL of humM2e-hBiTE-3 | AA | EVQLVESGGGLVQPGGSLRLSCAASGFTVSTYAMSWVRQTPEKRLEWVASISSGGSGSTYYPDSVKGRFTISRDNSKNTVYLQMNSLRAEDTAMYYCVRGG YGTSYWGQGTLVTVSSGGGGSGGGGSGGGGSDIVMTQTPLSLSVTPGEPASISCRSSQSIVHSIGDTYLEWYLQKPGQSPKLLIYKVSNRFSGVPDRFS GSGSGTDFTLKISRVEAEDVGVYYCFQGSHFPYTFGQGTKLEIK |
| 29 | VH-VL of humM2e-hBiTE-3 x anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATTAGTAGTGGTGGTAGTAGTACCTACTATCCAGACAGTGTAAAGGGCCGA TTCACCATCTCCAGAGATAATTCCAAGAACACCCTGTACCTGCAAATGAACAGTCTGAGGGCTGAGGATACAGTCTGTGTGTTCTGACATCAT TACGGAACTTCGTACTGGGGCCAAGGGACCACGGTCACCGTCTCCTCAGGTGGTGGTGGTTCTGGTGGTGGTGGTTCTGGCGGCGGCGGCTCAGGTGGTG GTGATGACCCAAACTCCACTCTCCCTGTCTGCAAACCAGGCCCTCGATCTACAAAGTTTCAACCCGATTTCTGGGGTCCCAGACAGGTTCAGT GGCAGTGGATCAGGGACAGATTTCACACTCAAGATCAGCAGAGTGGAGGCTGAGGATGTGGGAGTTTATTACTGCTTTCAAGGTTCACATTCCCGTAC ACGTTCGGACAGGGGGACCAAGCTGGAAATCCGGAGGTGGTGGATCGGCAGCTGGTTCCGGTTCCGGCTCCAGGTCTCACAGACTCCAGGAGGTTGCT TCATTGAAACTCTGCAGCCTCATGTGAAATATAATAATTATGCCGATTCAGTGAAAGACAGGTTCACAATCTCGGTAATAGCTCATATCCTACTGGGCTTACTGG CGCATAAAGAAGTAAATATAATTATGCCGATTCAGTGAAAGACAGGTTCACAATCTCGGTAATAGCTCATATCCTACTGGGCTTACTGG CTACAAATGAACAACTTGAAGACTGAGGCTGTGTACTACTGTGCTAAGCACGGGGTCCGTTATCATTGGGCTTTCAGGATCTGGCTTACTGG CCCCAAGGACTCTGTCTGTCACCGTGAACAGTCCACACTCACCTCACAAGTTCTCTGCCTCCTTCTGCCAGATTCTCAGGGTCCAACAAAA CCAGGTCAGGACGCCTGTGTCTACACCAGGGTGTCTAATAGGTGGACATGAGGCAGAATTATTACTGTGCTCATGGTACAACCGCTGGGTGTTCGGTGGAGGAACCAAGCTGCC GTCCTACATCATCACCATCATCAT |
| 30 | VH-VL of humM2e-hBiTE-3 x anti-CD3 | AA | EVQLVESGGGLVQPGGSLRLSCAASGFTVSTYAMSWVRQTPEKRLEWVASISSGGSGSTYYPDSVKGRFTISRDNSKNTVYLQMNSLRAEDTAMYYCVRGG YGTSYWGQGTLVTVSSGGGGSGGGGSGGGGSDIVMTQTPLSLSVTPGEPASISCRSSQSIVHSIGDTYLEWYLQKPGQSPKLLIYKVSNRFSGVPDRFS GSGSGTDFTLKISRVEAEDVGVYYCFQGSHFPYTFGQGTKLEIKSGGGGSEVQLVESGGGLVQPGGSLKLSCAASGFTFNKYAMNWVRQAPGKGLEWVA RIRSKYNNYATYYADSVKDRFTISRDDSKNTAYLQMNNLKTEDTAVYYCVRHGNFGNSYISYWAYWGQGTLVTVSSGGGGSGGGGSQTVVTQEP SLTVSPGGTVTLTCGSSTGAVTSGNYPNWVQQKPGQAPRGLIGGTKFLAPGTPARFSGSLLGGKAALTLSGVPEDEAEYYCVLWYSNRWVFGGGTKLT VLHHHHHH |
| 31 | VH of humM2e-hBiTE-4 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATTAGTAGTGGTGGTAGTACCTACTATCCAGACAGTGTAAAGGGCCGA TTCACCATCTCCAGAGATAATTCCAAGAACACCCTGTACCTGCAAATGAACAGTCTGAGGGCTGAGGATACAGTGTATTACTGTGTTAGAGGAGGC TACGGAACTTCGTACTGGGGCCAAGGGACCCTGGTCACCGTCTCCTCA |

| SEQ ID NO: | Designation | Type | Sequence |
|---|---|---|---|
| 32 | VH of humM2e-hBiTE-4 | AA | EVQLVESGGGLVQPGGSLRLSCAASGFTVSTYAMSWVRQTPGKRLEWVASMSSGGSLYYPDTVKGRFTISRDTSKNTVLQMNSLRAEDTAVYYCVRGGYGTSYWGQGTLVTVSS |
| 33 | VL of humM2e-hBiTE-4 | NT | GACATCGTGATGACCCAAACTCCACTCTCCCTGTCTGTCACTCCTGGAGACCCGGCCTCCATCTCTTGCAGATCTAGTCAGAGCATTGTTCATAGTATTGGAGACACCTATTTAGAATGGTACCTGCAGAAACCAGGCCAGTCTCCACAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAATTTATTACTGCTTTCAAGGTTCACATTTCCGTACACGTTCGGACAGGGGACCAAGCTGGAAATAAAA |
| 34 | VL of humM2e-hBiTE-4 | AA | DIVMTQTPLSLSVTPGEPASISCRSSQSIVHSIGDTYLEWYLQKPGQSPQLLIYKVSNRFSGVPDRFSGSGSTDFTLKISRVEAEDVGIYYCFQGSHFPYTFGQGTKLEIK |
| 35 | VH-VL of humM2e-hBiTE-4 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCCATGTCTTGGGTTCGCCAGATACTTCCAGGAGAGGGTCGAATGGGTCGCAATGAACAGTGTGAAGGTGGAGGCTTAACCTGTGTATTACTGTGTAAGAGAGGCTTCACCATCTCCAGAGATACTTCCAAGAACACCGTGTATTACTGTGTAAGAGAGGCTACGGAACTTCGTACTGGGGCCAAGGACACCCTGGTCACCGTCTCCAGTGGTGGTGGTTCTGGCGGCGGCGGCTCCGGTGGTGGTTCTGACATCGTGATGACCCAAACTCCACTCTCCCTGTCTGTCACTCCTGGAGACCCGGCCTCCATCTCTTGCAGATCTAGTCAGAGCATTGTTCATAGTATTGGAGACACCTATTTAGAATGGTACCTGCAGAAACCAGGCCAGTCTCCACAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAATTTATTACTGCTTTCAAGGTTCACATTTCCGTACACGTTCGGACAGGGGACCAAGCTGGAAATAAAA |
| 36 | VH-VL of humM2e-hBiTE-4 | AA | EVQLVESGGGLVQPGGSLRLSCAASGFTVSTYAMSWVRQTPGKRLEWVASMSSGGSLYYPDTVKGRFTISRDTSKNTVLQMNSLRAEDTAVYYCVRGGYGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFSGSGSTDFTLKISRVEAEDVGIYYCFQGSHFPYTFGQGTKLEIK |
| 37 | VH-VL of humM2e-hBiTE-4 x anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCCATGTCTTGGGTTCGCCAGATACTTCCAGGAGAGGGTCGAATGGGTCGCAATGAACAGTGTGAAGGTGGAGGCTTAACCTGTGTATTACTGTGTAAGAGAGGCTTCACCATCTCCAGAGATACTTCCAAGAACACCGTGTATTACTGTGTAAGAGAGGCTACGGAACTTCGTACTGGGGCCAAGGACACCCTGGTCACCGTCTCCAGTGGTGGTGGTTCTGGCGGCGGCGGCTCCGGTGGTGGTTCTGACATCGTGATGACCCAAACTCCACTCTCCCTGTCTGTCACTCCTGGAGACCCGGCCTCCATCTCTTGCAGATCTAGTCAGAGCATTGTTCATAGTATTGGAGACACCTATTTAGAATGGTACCTGCAGAAACCAGGCCAGTCTCCACAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATGTTGGAGTCTATTACTGCTTTCAAGGTTCACATTTCCCGTACACGTTCGGAGGAGGCACCAAGCTGGAGCTGAAAGGAGGTGGTGGATCTGGAGGCGGTGGAAGCGGAGGGGGAGGAAGTGAGGTGCAGCTGGTGGAGTCTGGGGGAGGCTTGGTCCAGCCTGGGGGGTCCCTGCGTCTCTCCTGTGCAGCCTCCGGATTCACCTTCAATAAATATGCCATGAACTGGGTCCGCCAGGCTCCAGGGAAGGGTCTGGAATGGGTCGCCCGTATTCGTAGTAAATATAATAATTATGCGACATACTATGCGGATTCAGTGAAAGGCAGATTCACCATCTCAGGTGATACATCACCCAAACACCCTCGGCTTACTGGCTCAAAGAAACATCCTACTGGGTCCAACACCTCCAAATAGCTACATATCCTATTGTTGCGAGAGCAGGTGGATTGCGGCCTCCAGTTCCTTTCCAGGTACATCCTCTCCCAGGTCAGGCCAGGCTGGATCCAACATCCGTGATTGAAGATATGCGGATGAACAGTCTCGAGAGTGAGGACACAGGCCGTCTATTACTGTGCGAGAAGGGGCGAGGAATGCGCGTCTTCGGCGCAAAGAAGGTCACCGGCATCATCTCTGGCCCCCCGGCGCACTCCTCCCCGATTCTCAGGTCCTCTGGGCGCTCGGGGCCGCCCACCTGGGCACTGTGAAGGGAACAATATCGACTGGAAGAAATAAGAGATTCAGCCAGCCTCCCCACCCCCCACAGTCTGCGGGAATGATGAGCGGATCAGACAGTGTCCGGCCACTTCAGGGACCCCTGCTGCCAGGGTGTTCTGACTTGTGTGCCCAGGAACCTCCACTGAACTTAATTCCCCGCCGTACATCAGTCCAACTACCATACCCTCATGGGTCAGGTTGTTCATCCAACATAACCAATACTGGTTCAGCCAAATGGTTGGAGGAAACCAAACTGGCTACTGACCCGTCCCTTGTCAGGGTAATGGGGGTGGTTGACCTGAGTCGAAAGGTCAGACGTCTAGAGAAGCAGCACCCCATACCCAGAAGCACCCTCTCCTTATGATATATCCCTTCGTAACCACTTCGCACATCAGCTTCCACCCCATCCTCCTCAAGCTCGCGCACCTTTTCCGGCTCTCAGGGTTACCACGTCTAAGCATCACACCCACCCTCCACTGGCTGCTACCTGAGGAACCAAAACTGACTGTCCTACATCATCACCATCACATCATCATTATCACATAGAATGCTCTACTCCGGACCAATCTGGAATAT |
| 38 | VH-VL of humM2e-hBiTE-4 x anti-CD3 | AA | EVQLVESGGGLVQPGGSLRLSCAASGFTVSTYAMSWVRQTPGKRLEWVASMSSGGSLYYPDTVKGRFTISRDTSKNTVLQMNSLRAEDTAVYYCVRGGYGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFSGSGSTDFTLKISRVEAEDVGIYYCFQGSHFPYTFGGGTKLEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLHHHHHH |

| SEQ ID NO: | Designation | Type | Sequence |
|---|---|---|---|
| 39 | VH of humM2e-hBiTE-5 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATGAGTAGTGGTGGTAGTGGTAGTACTTATTATCCAGACACTGTGAAGGGCCGA TTCACCATCTCCAGAGATACTTCCAAGAACACCCTGTACCTGCAAATGAACAGTCTGAGGGCTGAGGACACGGCCGTATTACTGTGTAAGAGGAGGC TACGGAACTTCGTACTGGGGCCAAGGGACCCTGGTCACCGTCTCCTCA |
| 40 | VH of humM2e-hBiTE-5 | AA | EVQLVESGGGLVQPGGSLRLSCAASGFTVSTYAMSWVRQTPGKRLEWVASMSSGGSGSTYYPDTVKGRFTISRDTSKNTVVLQMNSLRAEDTAVYYCVRGG YGTSYWGQGTLVTVSS |
| 41 | VL of humM2e-hBiTE-5 | NT | GACATCGTGATGACCCAAACTCCACTCTCCCTGTCTGTCACTCCTGGAGAACCGGCTGTCCTCTGATCTCAGAGAAACCAGGCCAGTTCCACAGTCCCAGATCTCTTCACTGTCAGGACACACTATTTAGAATGCACCTATCAGGATCAGATTTCACACTCAAGATCAGCAGAGTTGGAGGATGTGGAGCTGAGGATGTGGCAGATCAGCAGGAGTTGTAAGTGCTTTCAAGGTCCCAGACAGG CCGTACACGTTCGGACAGGGGACCAAGCTGGAAATAAAA |
| 42 | VL of humM2e-hBiTE-5 | AA | DIVMTQTPLSLSVTPGEPASISCRSSQSIVHSIGDTYLEWYLQKPGQSPQLLIYKVSNRFSGVPDRFSGSGSGTDFTLKISRVEAEDVGVYYCFQGSHF PYTFGQGTKLEIK |
| 43 | VH-VL of humM2e-hBiTE-5 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATGAGTAGTGGTGGTAGTGGTAGTACTTATTATCCAGACACTGTGAAGGGCCGA TTCACCATCTCCAGAGATACTTCCAAGAACACCCTGTACCTGCAAATGAACAGTCTGAGGGCTGAGGACACGGCCGTGTATTACTGTGTAAGAGGAGGC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCCTGTCTGTCACTCCTGGAGAACCGGCTGTCCTCTGATCTCAGAGATCCAGAGAACAGCATTAGTAGTGGAGAC ACCTATTTAGAATGGTACCTGCAGAAACCAGGACAGATTTCACACTCAAGATCTATAAAGTTTCAAACCGATTTTCTGGGGTCCCAGACAGTTCAGT GGCAGTGGATCAGGGACACAGATTTCACACTCAAGATCAGCAGAGTTGGAGGATGTGGAGATTGTTACTGCTTTCAAGGTTCACATTTCCCGTAC ACGTTCGGACAGGGGACCAAGCTGGAAATAAAA |
| 44 | VH-VL of humM2e-hBiTE-5 | AA | EVQLVESGGGLVQPGGSLRLSCAASGFTVSTYAMSWVRQTPGKRLEWVASMSSGGSGSTYYPDTVKGRFTISRDTSKNTVVLQMNSLRAEDTAVYYCVRGG YGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFS GSGSGTDFTLKISRVEAEDVGVYYCFQGSHFPYTFGQGTKLEIK |
| 45 | VH-VL of humM2e-hBiTE-5 x anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCCATGAGTAGTGGTGGTAGTGGTAGTACTTATTATCCAGACACTGTGAAGGGCCGA TTCACCATCTCCAGAGATACTTCCAAGAACACCCTGTACCTGCAAATGAACAGTCTGAGGGCTGAGGACACGGCCGTGTATTACTGTGTAAGAGGAGGC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCCTGTCTGTCACTCCTGGAGAACCGGCTGTCCTCTGATCTCAGAGATCCAGAGAACAGCATTAGTAGTGGAGAC ACCTATTTAGAATGGTACCTGCAGAAACCAGGACAGAGTCCACAGCTCCTCATCTATAAAGTTTCTAACCGATTTTCTGGGGTCCCAGACAGTTCAGT GGCAGTGGATCAGGGACAGATTTCACACTCAAGATCAGCAGAGTGGAGGATGTGGAGATTGTTACTGCTTTCAAGGTTCACATTTCCCGTACACGTTCGGCCAAGG GGACCAAGCTGGAAATCAAAGGTGGTGGTGGTTCTGGCGGCGGCGGCTCCGGTGGTGGTGGATCGGACATCAAGCTGCAGCAGTCTGGGGCTGAGCTGGCT AGACCTGGGGCCTCAGTGAAGATGTCCTGCAAGACTTCTGGCTACACCTTTACTAGGTACACGATGCACTGGGTAAAACAGAGGCCTGGACAGGGTCTGGAATGGATTGGATACATTAATCCTAGCCGTGGTTATACTAATTACAATCAGAAGTTCAAGGACAAGGCCACATTGACTGCAGACAAATCCTCCAGCACAGCCTACATGCAACTGAGCAGCCTGACATCTGAGGACTCTGCAGTCTATTACTGTGCAAGATATTATGATGATCATTACTGCCTTGACTACTGGGGCCAAGGCACCACTCTCACAGTCTCCTCAGGTGGAGGTGGATCAGGTGGAGGTGGATCTGGCGGAGGTGGCTCTGACATCCAGATGACACAGACTACATCCTCCCTGTCTGCCTCTCTGGGAGACAGAGTCACCATCAGTTGCAGGGCAAGTCAGGACATTAGTAAATATTTAAATTGGTATCAGCAGAAACCAGATGGAACTGTTAAACTCCTGATCTACCATACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTGGACGTTCGGTGGAGGCACCAAGCTGGAAATCAAACGCGGAGGCGGAGGTTCTGGAGGCGGCGGCAGCGGAGGCGGGGGCAGCCACCATCACCATCACCATCAT |

| SEQ ID NO: | Designation | Type | Sequence |
|---|---|---|---|
| 46 | VH-VL of humM2e-hBiTE-5 × anti-CD3 | AA | EVQLVESGGGLVQPGGSLRLSCAASGFTVSTYAMSWVRQTPGKRLEWVASMSSGGSLYYPDTVKGRFTISRDTSKNTVVLQMNSLRAEDTAVYYCVRGGYGTSYWGQGTLVTVSSGGGGSGGGGSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLMYSNRWVFGGGTKLTVLHHHHHH |
| 47 | VH of humM2e-hBiTE-6 | NT | GAGGTGCAGCTGGTCGAGTCTGGGGGAGGCTTAGTGCAGCCTGGAGGGTCCCTGAGACTCTCCTGTGCAGCCTCTGGATTCACTGTGACTTATATGCCATGTCTTGGGTTCGCCAGACTCCAGAGAAGGAGGCTGGAATGGTCGCATCATGAATGAACACTGTACCTGTAAATATCAGAACACTGTAAGGGCCGATTCACCATCTCCAGAGACAATTCCAACACAGTCTACCTGCAAATGAACAGTCTGAGGGCTGAGGACACTGCCGTGTATTACTGTGTAAGAGGAGGCTACGGAACTTCGTACTGGGGCCAAGGGACCACCCTGGTCACCGTCTCCTCA |
| 48 | VH of humM2e-hBiTE-6 | AA | EVQLVESGGGLVQPGGSLRLSCAASGFTVSTYAMSWVRQTPGKRLEWVASMSSGGSLYYPDTVKGRFTISRDTSKNTVVLQMNSLRAEDTAVYYCVRGGYGTSYWGQGTLVTVSS |
| 49 | VL of humM2e-hBiTE-6 | NT | GACATCGTGATGACCCAAACTCCACTCTCCCTGTCTGTCAGATCTCTTGGAGAACCGGCTCCATCTTCTGCAGATCAGTGCAGACCATTGTTCATAGTATTGGAGACACCTATTTAGAATGTATCAGGCAGAAACCAGGCCAGTCTCCAAAGTTTCTCATCTACAAAGTTTCGGGAGTTTATTACTGCTTTCAAGGTTCAACATTTCCCGTACACGTTCGGACAGGGGACCAAGCTGGAAATAAAA |
| 50 | VL of humM2e-hBiTE-6 | AA | DIVMTQTPLSLSVTPGEPASISCRSSQSIVHSIGDTYLEWYLQKPGQSPKLLIYKVSNRFSGVPDRFSGSGSGTDFTLKISRVEAEDVGVYYCFQGSHFPYTFGQGTKLEIK |
| 51 | VL of humM2e-hBiTE-6 | NT | GAGGTGCAGCTGGTCGAGTCTGGGGGAGGCTTAGTGCAGCCTGGAGGGTCCCTGAGACTCTCCTGTGCAGCCTCTGGATTCACTGTGACTTATATGCCATGTCTTGGGTTCGCCAGACTCCAGAGAAGGAGGCTGGAATGGTCGCATCATGAATGAACACTGTACCTGTAAATATCAGAACACTGTAAGGGCCGATTCACCATCTCCAGAGACAATTCCAACACAGTCTACCTGCAAATGAACAGTCTGAGGGCTGAGGACACTGCCGTGTATTACTGTGTAAGAGGAGGCTACGGAACTTCGTACTGGGGCCAAGGGACCACCCTGGTCACCGTCTCCTCAGGTGGTGGTGGTTCTGGCGGCGGCGGCTCCGGTGGTGGTGGTTCTGACATCGTGATGACCCAAACTCCACTCTCCCTGTCTGTCAGATCTCTTGGAGAACCGGCTCCATCTTCTGCAGATCAGTGCAGACCATTGTTCATAGTATTGGGGATCAGGACACAGATTTCACACTCTACAAAGTTTCACCTTCAAGGTGTGGAGTTTATTACTGCTTTCAAGGTTCAACATTTCCCGTAC ACGTTCGGACAGGGGACCAAGCTGGAAATAAAA |
| 52 | VH-VL of humM2e-hBiTE-6 | AA | EVQLVESGGGLVQPGGSLRLSCAASGFTVSTYAMSWVRQTPGKRLEWVASMSSGGSLYYPDTVKGRFTISRDTSKNTVVLQMNSLRAEDTAVYYCVRGGYGTSYWGQGTLVTVSSGGGGSGGGGSGGGGSDIVMTQTPLSLSVTPGEPASISCRSSQSIVHSIGDTYLEWYLQKPGQSPKLLIYKVSNRFSGVPDRFSGSGSGTDFTLKISRVEAEDVGVYYCFQGSHFPYTFGQGTKLEIK |
| 53 | VH-VL of humM2e-hBiTE-6 × anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGACTTATATGCCATGTCTTGGGTTCGCCAGACTCCAGAGAAGGAGGCTGGAATGGTCGCATCATGAATGAACACTGTACCTGTAAATATCAGAACACTGTAAGGGCCGATTCACCATCTCCAGAGACAATTCCAACACAGTCTACCTGCAAATGAACAGTCTGAGGGCTGAGGACACTGCCGTGTATTACTGTGTAAGAGGAGGCTACGGAACTTCGTACTGGGGCCAAGGGACCACCCTGGTCACCGTCTCCTCAGGTGATGACCCAAACTCCACTCTCCCTGTCTGTCAGATCTCTTGGAGAACCGGCTCCATCTTCTGCAGATCAGTGCAGACCATTGTTCATAGTATTGGAGACACCTATTTAGAATGGTACCTGCAGAAACCAGGCCAGTCTCCAAAGTTCACACTCTACAAAGTTGGGAGTTGTGGAGATTGTGCAGCCTGGAGGCAGTGGATCAGGGACAGATTTCACACTCTACAAAGTTTCACCTTCAAGGTTGGAGTTTATTACTGCTTTCAAGGTTCACATTTCCCGTACACGTTCGGACAGGGGACCAAGCTGGAAATAAAATCATTGAAACTCATGTGCAGCCTCGATTCAGCCTTCACCATATTGCAACATATATTGCCATCCAGAGAAAATGATTGTCAGCCTGGAGGTTTGAATAAAACACTGCCTATCTGTAAGAAGAACAACTTGAAGACTTGTGAGAACTGTGTAGAAAGCTCGGTGTACTGGGCTTCTAAAGGGATTCAGAACTCGGCATCAGCCAAGGGACCTCGTGTCACCGTCTCCTCAGGTGGTGGTGGTTCTGGCGGCGGCGGCTCCGGTGGTGGTGGTTCTCAGACTGTTGTGACTCAGGAACCT |

| SEQ ID NO: | Designation | Type | Sequence |
|---|---|---|---|
| | | | TCACTCACCGTATCACCTGGTGAACAGTCACACTCACTTGTGCTCCTCCGACTTGTTACATCTGGACAACTACCCAAACTGGTCAACAAAAA CCAGTCAGGCACCCGTGTCTAATAGTGGACTAAGTTCTCGCCCCGACTCCTCCAGATTCTCAGGTCTGTTGAGGCAAGCTGCC CTCACCCTCTCAGGGTACAGCCAGAGGATGAGCAGAATATTACTGTTCTATGGTACAGCAACCGCTGGGTTCGTGAGGAACCAAACTGACT GTCCTACATCATCACCATCAT |
| 54 | VH-VL of humM2e-hBiTE-6 × anti-CD3 | AA | EVQLVESGGGLVQPGGSLRLSCAASGFTVSTYAMSWVRQTPGKRLEWVASMSSGGGSDIVMTQTPLSLSVTPGEPASISCRSSQSIVHSIGDTYLEWYLQKPGQSPKLLIYKVSNRFSGVPDRFS GSGSGTDFTLKISRVEAEDVGVYYCFQGSHFPYTFGQGTKLEIKSGGGSGGGGSEVQLVESGGGLVQPGGSLKLSCAASGFTFNKYAMNWVRQAPGKGLEWVA RIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEP SLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLT VLHHHHHH |
| 55 | VH of humM2e-hBiTE-7 | NT | GAGGTGCAGCTGGTCGAGTCTGGGGGAGGCTTAGTGCAGCCTGGAGGGTCCGATCGAGACTCTCCTGTGCAGCCTCTGGATTCACTGTGAGTACTTATGCC ATGTCTTGGGTTCGCCAGGATAATTCCAGAGAACACTGGAATGGGTCGCAATGAACAGTCTGAGGCTGAGGACACTGTGTAAGGGCGA TTCACCATCTCCAGAGATAATTCCAAGAACATTGTACCTGCAAATGAACAGTCTGAGGCGTGAGGACACGGCCGTGTATTACTGTGTAAGAGGAGGC TACGGAACTTCGTACTGGGGCCAAGGGACCCTGGTCACCGTCTCCTCA |
| 56 | VH of humM2e-hBiTE-7 | AA | EVQLVESGGGLVQPGGSLRLSCAASGFTVSTYAMSWVRQTPEKRLEWVASMSSGGGSDFTLKISRDNSKNIVVLQMNSLRAEDTAVYYCVRGG YGTSYWGQGTLVTVSS |
| 57 | VL of humM2e-hBiTE-7 | NT | GACATCGTGATGACCCAAACTCCACTCTCCTGTCTCTGCAGCTCCCTGGAGACCTCAGTGCATTGTCATAGTATT GGAGACACCTATTTAGAATGTACCTGCAGAAACCAGGCCAGTCTCCACAGCCCTCCTGATCTACAAAGTTTCACAACGATGTGGGGTCCCAGACAGG TTCAGTGGCAGTGGATCAGGGACAGATTTCACACTCAAGATCAGCAGAGTGGAGGCTGAGGATGTGGAATTTATTACTGCTTTCAAGGTTCACATTTC CCGTACACGTTCGGACAGGGGACCAAGCTGGAAATAAAA |
| 58 | VL of humM2e-hBiTE-7 | AA | DIVMTQTPLSLSVTPGEPASISCRSSQSIVHSIGDTYLEWYLQKPGQSPQLLIYKVSNRFSGVPDRFSGSGSGTDFTLKISRVEAEDVGIYYCFQGSHF PYTFGQGTKLEIK |
| 59 | VH-VL of humM2e-hBiTE-7 | NT | GAGGTGCAGCTGGTCGAGTCTGGGGGAGGCTTAGTGCAGCCTGGAGGGTCCGATCGAGACTCTCCTGTGCAGCCTCTGGATTCACTGTGAGTACTTATGCC ATGTCTTGGGTTCGCCAGACTCCAGAGAAGAGGCTGGAATGGGTCGCAATGAACAGTCTGAGGCTGAGGACACTGTGTAAGGGCGA TTCACCATCTCCAGAGATAATTCCAAGAACATTGTACCTGCAAATGAACAGTCTGAGGCCGTGAGGACACGGCCGTGTATTACTGTGTAAGGAGGC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCTGTCTCTGCAGCTCCCTGGAGATCTCAGTCACCACCAGTTCCAACAAGTTTCACAACGATCAAAGTTTCACACTCAAGATCAGCAGAGTTGAGCAAGGCCTGCAGTTCAGT GGCAGTGGATCAGGGACAGATTTCACACTCAAGATCAGCAGAGTGGAGGCTGAGGATGTGGAATTTATTACTGCTTTCAAGGTTCACATTTCCCGTAC ACGTTCGGACAGGGGACCAAGCTGGAAATAAAA |
| 60 | VH-VL of humM2e-hBiTE-7 | AA | EVQLVESGGGLVQPGGSLRLSCAASGFTVSTYAMSWVRQTPEKRLEWVASMSSGGGSDIVMTQTPLSLSVTPGEPASISCRSSQSIVHSIGDTYLEWYLQKPGQSPQLLIYKVSNRFSGVPDRFS GSGSGTDFTLKISRVEAEDVGIYYCFQGSHFPYTFGQGTKLEIK |
| 61 | VH-VL of humM2e-hBiTE-7 × anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCAATGAGTAGTGGTGGTAGTACACTGTGAGTACTGTGTAAGGGCCGA TTCACCATCTCCAGAGATAATTCCAAGAACATTGTACCTGCAAATGAACAGTCTGAGGACACGGCCGTGTATTACTGTGTAAGAGGAGGC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCTGTCTCTGCAGCTCCCTGGAGATCTCAGTCACCACCAGTTCCAACAAGTTTCACAACGATCAAAGTTTCACAAGATCAGCAGAGTTCAGT GGCAGTGGATCAGGGACAGATTTCACACTCAAGATCAGCAGAGTGGAGGCTGAGGATGTGGAATTTATTACTGCTTTCAAGGTTCACATTTCCCGTAC |

| SEQ ID NO: | Designation | Type | Sequence |
|---|---|---|---|
| | | | ACGTTCGACAGGGACCAAGCTGGAATCTGGTGGAATCCGAGGTGGTGCAGCTGGTCGAGTCTGGAGGAGGATTGTGCAGCCTGAGGG<br>TCATTGAAACTCTGTGCAGCCTGCGATTCACCTTCAATAGTACGGCCATGAACTGGGTCCGCCAGGCTCCAGAGATGCTTTGCT<br>CGCATAAGAAGTAAATATAATATTATGCAACATATATTATGCCGATTCAGTGAAAGACACAGTTCGGTGAACTTCGGTAATATCCTAT<br>CTACAAATGAACAGCTCGAGAGCTGCTGAGGAGATGGCGCTCGGGCTGTTGGGCTACTACTGCGCTCGTAATAGCTACTATCCTACTGGCTTACTGG<br>GGCCAAGGGACTCTGGTCACCGTCTCCTCAGGTGGTGGTGGTTCTGGCGGCGGCGGCCAGCTGTGTACTTGTGACTCAGGAACCT<br>TCACTCACCGTATCCACCTGGTGCAGTCACACTGCACTTCTGCCTCCCCCGGTACTCTGTCACATCTGAGACCCCTCCAACAAAA<br>CCAGTTCAGGCACCCTGCGATCAATAGGTGGACTAAGTTCTGCCCCAGATTCACTGGCAGCTTCTGGGCTCTGGAGGCAAGCTGCC<br>CTCACCCTTCCAGGGATCTACGACCAGGAGGATGAGGCCAGAATATTACTGTGTTCTATGGTACCAGCAACCGCTGGGTTCGGTGAGGAACCAAACTGACT<br>GTCCTACATCATCATCATCAT |
| 62 | VH-VL of humM2e-hBiTE-7 × anti-CD3 | AA | EVQLVESGGGLVQPGGSLRLSCAASGFTVSTYAMSWVRQTPEKRLEWVASMSSGGSLYYPDTVKGRFTISRDNSKNIVVLQMNSLRAEDTAVYYCVRGG<br>YGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFS<br>GSGSGTDFTLKISRVEAEDVGVYYCFQGSHFPYTFGQGTKLEIKSGGGSEVQLVESGGGLVQPGGSLKLSCAASGFTFNKYAMNWVRQAPGKGLEWVA<br>RIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEP<br>SLTVSPGGTVTLTCGSSTGAVTSGNYPNWVQQKPGQAPRGLIGGTKFLAPGTPARFSGSLLGGKAALTLSGVQPEDEAEYYCVLMYSNRWVFGGGTKLT<br>VLHHHHHH |
| 63 | VH of humM2e-hBiTE-8 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC<br>ATGTCTTGGGTTCGCCAGACTCCAGAGAAGAGGCTGGAATGGGTCGCATCCATGAGTAGTGGTGGTAGTAGTTATTATCCAGACACTGTGAAGGGCCGA<br>TTCACCATCTCCAGAGATAATTCCAAGAACATTGTACCTGCAAATGAACAGTCTGAGGGCTGAGGACACAGCCGTGTATTACTGTGTAAGAGGAGGC<br>TACGGAACTTCGTACTGGGGCCAAGGGACCCCTGGTCACCGTCTCCTCA |
| 64 | VH of humM2e-hBiTE-8 | AA | EVQLVESGGGLVQPGGSLRLSCAASGFTVSTYAMSWVRQTPEKRLEWVASMSSGGSSYYPDTVKGRFTISRDNSKNIVVLQMNSLRAEDTAVYYCVRGG<br>YGTSYWGQGTLVTVSS |
| 65 | VL of humM2e-hBiTE-8 | NT | GACATCGTGATGACCCAAACTCCACTCTCCCTGTCTGTCAGAAACCGGCTCTGATCTACAAAGTTTCCAACCGATTTTCTGGGGTCCCAGACAGG<br>GGAGACACTATTTAGAATGACCAGCACCAATTGTACTGCAGTCTCCAGACATCAGCAGTCCAGTGAGGCTGAGGATGTGGAGTTATTACTGCTTTCAAGGTTCACATTTC<br>TCAGTGGCAGTCAGGGACAGATTTCACACTCAAGATCAGCAGACTGGAAGCTGAGGATGTGGAGTTATTACTGCTTTCAAGGTTCACATTTC<br>CCGTACACGTTCGGACAGGGGACCAAGCTGGAAATAAAA |
| 66 | VL of humM2e-hBiTE-8 | AA | DIVMTQTPLSLSVTPGEPASISCRSSQSIVHSIGDTYLEWYLQKPGQSPQLLIYKVSNRFSGVPDRFSGSGSGTDFTLKISRVEAEDVGVYYCFQGSHF<br>PYTFGQGTKLEIK |
| 67 | VH-VL of humM2e-hBiTE-8 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC<br>ATGTCTTGGGTTCGCCAGACTCCAGAGAAGAGGCTGGAATGGGTCGCATCCATGAGTAGTGGTGGTAGTAGTTATTATCCAGACACTGTGAAGGGCCGA<br>TTCACCATCTCCAGAGATAATTCCAAGAACATTGTACTGCAAATGAACAGTCTGAGGGCTGAGGACACAGCCGTGTATTACTGTGTAAGAGGAGGC<br>TACGGAACTTCGTACTGGGGCCAAGGGACCCTGGTCACCGTCTCCTCAGGTGGTGGTGGTTCTGGCGGCGGCGGCCAGCTGTGGTGGTTCTGGCGGCGGCGGATC<br>GGATGACCCAAACTCCACTCTCCCTGTCTGTCACCGAGATCTGGAGAATCCAGCCTGATCTACAAAGTTTCCAACCGATTTTCTGGGGTCCCAGACAGG<br>ACCTATTTAGAATGACCAGCACCAATTGTACTGCAGTCTCCAGACATCAGCAGTCCAGTGAGGCTGAGGATGTGGAGTTATTACTGCTTTCAAGGTTCACATTTCCCGTAC<br>GGCAGTGGCAGTCAGGGACAGATTTCACACTCAAGATCAGCAGACTGGAGGCTGAGGATGTGGAGTTATTACTGCTTTCAAGGTTCACATTTCCCGTAC<br>ACGTTCGGACAGGGGACCAAGCTGGAAATAAAA |
| 68 | VH-VL of humM2e-hBiTE-8 | AA | EVQLVESGGGLVQPGGSLRLSCAASGFTVSTYAMSWVRQTPEKRLEWVASMSSGGSSYYPDTVKGRFTISRDNSKNIVVLQMNSLRAEDTAVYYCVRGG<br>YGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFS<br>GSGSGTDFTLKISRVEAEDVGVYYCFQGSHFPYTFGQGTKLEIK |

| SEQ ID NO: | Designation | Type | Sequence |
|---|---|---|---|
| 69 | VH-VL of humM2e-hBiTE-8 × anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCAATGAACAGTGACAGTGAGGAAGTAGTCTTATTATCCAGACACTGTAAGGGCCGA TTCACCATCTCACGAGATAATTCCAAGGGCCAAGCCACCTTGTACCTGCAAATGAACAGTCTGAGGGCTGAGGACACGGCCGTGTATTACTGTGTCAGATC TACGGAACTTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCCTGCCTGTCACTCCTGGAGACCCGGCCTCCATCTCTTGCAGATCTAGTCAGAGCATTGTTCATAGTATTGGAGAC GGCAGTGGATCAGGGACACAGATTTCACACTCAAGATCAGCAGAGTGGAGGCTGAAGATCTGGGAGTTTATTACTGCTTTCAAGGTTCACATTTCCCGTAC ACGTTCGGACAGGGGACCAAGCTGGAAATAAAAATCGGGGATTCGGAGGTGGCAGTGGCAGTGGATCTGGAGGATAACACACTAAAAAACACTGGCT TCATTGAAACTTCATGTGCAGCCTGGATTCAGCTTCAATAATTATGCCAACACTGGCCGTGTACTACCGCCGATTCAGCTCCGAGACTGGTCCAAGGT TAAAAAGGAAGAATAACACTTGAGAAGAGACATCACATATATCCGATTCAGTCGGAGAACTGGGTGTTCGCAGCTTTGAGAAGCTCTGACTCAGGAAC GGCCAAGGGACTTCGTCACCGTCTCCTCAGGTGAACAGTCACCTGTTCTACACCCCGTTGCAAGATACCCTGGTGTTCTACATCTCAGGCCTCAACAAGAA TCACTCACCCTATCCCGTGTGAACACAGGCAACACCTACCTGTGCCTCTCGCCCAGATTCTCCGTGACCCCTGAGCAACCGTCTGTCGTGCAGAGGCAAAGGCTGCC CCAGGTCAGGGACGCCACCCGTGGTCTAATAGTGGACATGAGGCGATGAGCAGATATATTACTGCTTGTATTACCGACCAACAACCCGGCTGGTTCGGCCAGTGAGGAACCAATTGACT GTCCTACATCATCACCATCATCAT |
| 70 | VH-VL of humM2e-hBiTE-8 × anti-CD3 | AA | EVQLVESGGGLVQPGGSLRLSCAASGFTVSTYAMSWVRQTPEKRLEWVASMSSGGSLYYPDTVKGRFTISRDNSKNIVVLQMNSLRAEDTAVYYCVRGG YGTSYWGQGTLVTVSSGGGGSGGGGSGGGGSDIVMTQTPLSLSVTPGEPASISCRSSQSIVHSIGDTYLEWYLQKPGQSPQLLIYKVSNRFSGVPDRFS GSGSGTDFTLKISRVEAEDVGVYYCFQGSHFPYTFGQGTKLEIKSGGGSEVQLVESGGGLVQPGGSLKLSCAASGFTFNKYAMNWVRQAPGKGLEWVA RIRSKYNNYATYYADSVKDRFTISRDDSKNTAYLQMNNLKTEDTAVYYCVRHGNFGNSYISYNAYWGQGTLVTVSSGGGGSGGGGSGGGGSQTVVTQEP SLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLT VLHHHHHH |
| 71 | VH of humM2e-hBiTE-9 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCAATGAGCAGTGACAGTGAGGAAGTAGTCTTATTATCCAGACACTGTAAGGGCCGA TTCACCATCTCACGAGATAATTCCAAGGGACCCTGGTCACCGTCTCCTCA TACGGAACTTCGTACTGGGGCCAAGGGACCCTGGTCACCGTCTCCTCA |
| 72 | VH of humM2e-hBiTE-9 | AA | EVQLVESGGGLVQPGGSLRLSCAASGFTVSTYAMSWVRQTPEKRLEWVASMSSGGSLYYPDTVKGRFTISRDNSKNIVVLQMNSLRAEDTAVYYCVRGG YGTSYWGQGTLVTVSS |
| 73 | VL of humM2e-hBiTE-9 | NT | GACATCGTGATGACCCAAACTCCACTCTCCCTGTCTGTCACTCCTGGAGACCCGGCCTCCATCTCTTGCAGATCTAGTCAGAGCATTGTTCATAGTATT GGAGACACCTATTTAGAATGTACCTGCAGAAACCAGGCCAGTCTCCAAAGCTCCTGATCTACAAAGTTTCCAACCGATTTTCTGGGGTCCCAGACAGG TTCAGTGGCAGTGGATCAGGGACAGATTTCACACTCAAGATCAGCAGAGTGGAGGCTGAGGATGTGGGAGTTTATTACTGCTTTCAAGGTTCACATTTC CCGTACACGTTCGGACAGGGGACCAAGCTGGAAATAAAA |
| 74 | VL of humM2e-hBiTE-9 | AA | DIVMTQTPLSLSVTPGEPASISCRSSQSIVHSIGDTYLEWYLQKPGQSPKLLIYKVSNRFSGVPDRFSGSGSGTDFTLKISRVEAEDVGVYYCFQGSHF PYTFGQGTKLEIK |
| 75 | VH-VL of humM2e-hBiTE-9 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTTCGCCAGACTCCAGAGAAGAGGCTGGAATGGGTCGCATCAATGAACAGTGACAGTGTAGTCTTATTATCCAGACACTGTAAGGGCCGA TTCACCATCTCGTACTGGGGCCAAGGGACCCTGGTCACCGTCTCCTCAGGTGGTGGTGGTTCTGGCGGCGGCGGCTCCGGTGGTGGTGGTTCTGACATC GTGATGACCCAAACTCCACTCTCCCTGTCTGTCACTCCTGGAGACCCGGCCTCCATCTCTTGCAGATCTAGTCAGAGCATTGTTCATAGTATTGGAGAC ACCTATTTAGAATGTACCTGCAGAAACCAGGCCAGTCTCCAAAGCTCCTGATCTACAAAGTTTCCAACCGATTTTCTGGGGTCCCAGACAGGTTCAGT GGCAGTGGATCAGGGACAGATTTCACACTCAAGATCAGCAGAGTGGAGGCTGAGGATGTGGGAGTTTATTACTGCTTTCAAGGTTCACATTTCCCGTAC ACGTTCGGACAGGGGACCAAGCTGGAAATAAAA |

-continued

| SEQ ID NO: | Designation | Type | Sequence |
|---|---|---|---|
| 76 | VH-VL of humM2e-hBiTE-9 | AA | EVQLVESGGGLVQPGGSLRLSCAASGFTVSTYAMSWVRQTPEKRLEWVASMSSGGSLYYPDTVKGRFTISRDNSKNIVVLQMNSLRAEDTAVYYCVRGG YGTSYWGQGTLVTVSSGGGGSGGGGSGGGGSDIVMTQTPLSLSVTPGEPASISCRSSQSIVHSIGDTYLEWYLQKPGQSPKLLIYKVSNRFSGVPDRFS GSGSGTDFTLKISRVEAEDVGVYYCFQGSHFPYTFGQGTKLEIK |
| 77 | VH-VL of humM2e-hBiTE-9 × anti-CD3 | NT | GAGGTGCAGCTGGTCGAGTCTGGGGGAGGCTTAGTGCAGCCTGGAGGGTCCCTGAGACTCTCCTGTGCAGCCTCTGGATTCACTGTGAGTACTTATGCC ATGTCTTGGGTCCGCCAGACTCCAGAGAAGAGGCTGGAATGGGTCGCATCCATGAGTAGTGGTGGTAGTAGCACTTACTATGCAGACTGTGTAAGGGCCGA TTCCACCATCTCCAGAGACAATTCCAAGAACATTGTACCTGCAAATGAACAGTCTGAGGGCTGAGGACACGGCCGTGTATTACTGTGTAAGAGGAGGC TACGGAACTTCGTACTGGGGCCAAGGGACCCTGGTCACCGTCTCCTCAGGTGGTGGCGGTTCAGGCGGAGGTGGCTCTGGCGGTGGCGGATCGGACATC GTGATGACCCAAACTCCACTCTCCCTGCCTGTCACTCCTGGAGAACCGGCTCCATCTCCTGCAGATCGAGCCAGTCAGAGCATTGTTCATGATATTGAGAC ACCTATTTAGAATGGTACCTGCAGAAACCAGGCCAGTCTCCAAAGCTCCTGATCTACAAAGTTTCAACCAGATTTCTGGGGTCCCAGACAGGTTCAGT GGCAGTGGATCAGGGACAGATTTCACACTGAAGATCAGCAGAGTGGAGGCTGAGGATGTTGGAGTTTATTACTGCTTTCAAGGTTCAATTTCCGTAC ACGTTCGGACAGGGGACCAAGCTGGAATCAAAATAAAAT |
| 78 | VH-VL of humM2e-hBiTE-9 × anti-CD3 | AA | EVQLVESGGGLVQPGGSLRLSCAASGFTVSTYAMSWVRQTPEKRLEWVASMSSGGSLYYPDTVKGRFTISRDNSKNIVVLQMNSLRAEDTAVYYCVRGG YGTSYWGQGTLVTVSSGGGGSGGGGSGGGGSDIVMTQTPLSLSVTPGEPASISCRSSQSIVHSIGDTYLEWYLQKPGQSPKLLIYKVSNRFSGVPDRFS GSGSGTDFTLKISRVEAEDVGVYYCFQGSHFPYTFGQGTKLEIKSGGGGSEVQLVESGGGLVQPGGSLKLSCAASGFTFNKYAMNWVRQAPGKGLEWVA RIRSKYNNYATYYADSVKDRFTISRDDSKNTAYLQMNNLKTEDTAVYYCVRHGNFGNSYISYNAYWGQGTLVTVSSGGGGSGGGGSGGGGSQTVVTQEP SLTVSPGGTVTLTCSSSTGAVTSGNYPNWVQQKPGQAPRGLIGGTKFLAPGTPARFSGSLLGGKAALTLSGVQPEDEAEYYCVLMYSNRWVFGGGTKLT VLHHHHHH |
| 79 | VH of murM2e-hBiTE | NT | GAGGTGCAGCTGCTCGAGTCTGGGGGAGGCTCAGTGAAGCCTGGAGGGTCCCTGAAACTCTCCTGTTCAGCCTCTGGATTCTCTTTGAGTACTTATGCC ATGTCTTGGGTTCGCCAGACTCCAGAAGAAGAGGCTGGAATGGGTCGCATCCATGAGTGTCAAATGAACAGTCTGAGGGCTGAGGACACTGTGAAGGCCGA TTCACCATCTCCAGAGACAATCTCAAGAACATTGTACCTGCAAATGAGCAGTCTGAGGTCTGAGGACACTGTGAAGACCATGTATTACTGTGTAAGAGGAGGC TACGGAACTTCGTACTGGGGCCAAGGGACCACGGTCACCGTCTCCTCA |
| 80 | VH of murM2e-hBiTE | AA | EVQLLESGGGSVKPGGSLKLSCSASGFSLSTYAMSWVRQTPEKRLEWVASMSSGGSLYYPDTVKGRFTISRDTVKNIVVLQMSSLRSEDTAMYYCVRGG YGTSYWGQGTTVTVSS |
| 81 | VL of murM2e-hBiTE | NT | GAGCTCTTGTTGACCCAATCTCCACTCTCCCTGCCTGTCAGTCTTGGAGATCAGCCTCCATCTCTTGCAGATCTAGTCAGAGCATTGTTCATAGTATT GGAGACACCTATTTAGAATGGTACCTGCAGAAACCAGGCCAGTCTCCAAAGCTCCTGATCTACAAAGTTTCCAACCGATTTTCTGGGGTCCCAGACAGG TTCAGTGGCAGTGGATCAGGGACAGATTTCACACTCAAGATCAGCAGAGTGGAGGCTGAGGATCTGGGAATTTATTACTGCTTTCAAGGTTCACATTTT CCGTACACGTTCGGAGGGGGGACCAAGCTGGAAATAAAA |

-continued

| SEQ ID NO: | Designation | Type | Sequence |
|---|---|---|---|
| 82 | VL of murM2e-hBiTE | AA | ELLLTQTPLSLPVSLGDQASISCRSSQSIVHSIGDTYLEWYLQKPGQSPKLLIYKVSNRFSGVPDRFSGSGSGTDFTLKISRVEAEDLGIYYCFQGSHF PYTFPGGGTKLEIK |
| 83 | VH-VL of murM2e-hBiTE | NT | GAGGTGCAGCTGCTCGAGTCTGGGGGAGGCTCAGTGAAGCCTGGAGGGTCCCTGAAACTCTCCTGTTCAGCCTCTGGATTCTCTTTGAGTACTTATGCC ATGTCTTGGGTTCGCCAGACTCCAGAGAAGAGGCTGGAATGGGTCGCATCCATGAGAGTCTGTAGTCTTATTATCCAGACACTGTGAAGGGCCGA TTCACCATCTCCAGAGATACTGGGGACCAAGGGACCACGGTCACCGTCTCCTCAGGTGGTGGTGGTTCTGGCGGCGGCGGCTCCGGTGGTGGTGGTTCTGAGCTC GTTGTGACCCAAACTCCACTCTCCCTGCCTGTCAGTCTTGGAGATCAGGCCTCAGATCTAGTGACAGTAGTCAGAGACATTGTTCATAGTATTGGAGAC ACCTATTTAGAATGGTACCTGCAGAAACCAGGCCAGTCTCCAAAGCTCCTGATCTACAAAGTTTCAAGCTGGAATTTATTACTGCTTTCAAGGTCAGT GGCAGTGGATCAGGGACAGATTTCACACTCAAGATCAGCAGAGTGGAGGCTGAGGATCTGGGAATTTATTACTGCTTTCAAGGTCAGTCAGGTTCAGT ACGTTCGGAGGGGGGACCAAGCTGAAATAAAA |
| 84 | VH-VL of murM2e-hBiTE | AA | EVQLLESGGGSVKPGGSLKLSCSASGFSLSTYAMSWVRQTPEKRLEWVASMSSGGSLYYPDTVKGRFTISRDTVKNIVVLQMSSLRSEDTAMYCVRGG YGTSYWGQGTTVTVSSGGGGSGGGGSGGGGSELLLTQTPLSLPVSLGDQASISCRSSQSIVHSIGDTYLEWYLQKPGQSPKLLIYKVSNRFSGVPDRFS GSGSGTDFTLKISRVEAEDLGIYYCFQGSHFPYTFGGGTKLEIK |
| 85 | VH-VL of murM2e-hBiTE x anti-CD3 | NT | GAGGTGCAGCTGCTCGAGTCTGGGGGAGGCTCAGTGAAGCCTGGAGGGTCCCTGAAACTCTCCTGTTCAGCCTCTGGATTCTCTTTGAGTACTTATGCC ATGTCTTGGGTTCGCCAGACTCCAGAGAAGAGGCTGGAATGGGTCGCATCCATGAGAGTCTGTAGTCTTATTATCCAGACACTGTGAAGGGCCGA TTCACCATCTCCAGAGATACTGGGGACCAAGGGACCACGGTCACCGTCTCCTCAGGTGGTGGTGGTTCTGGCGGCGGCGGCTCCGGTGGTGGTGGTTCTGAGCTC TTGTTGACCCAAACTCCACTCTCCCTGCCTGTCAGTCTTGGAGATCAGGCCTCAGATCTAGTGACAGTAGTCAGAGACATTGTTCATAGTATTGGAGAC ACCTATTTAGAATGGTACCTGCAGAAACCAGGCCAGTCTCCAAAGCTCCTGATCTACAAAGTTTCAAGCTGGAATTTATTACTGCTTTCAAGGTCAGT GGCAGTGGATCAGGGACAGATTTCACACTCAAGATCAGCAGAGTGGAGGCTGAGGATCTGGGAATTTATTACTGCTTTCAAGGTCAGTCAGGTTCAGT ACGTTCGGAGGGGGGACCAAGCTGGAGATCAAAGGTTCTGGGAGGATTGGTGCAGCCTGGAGGG TCATTGAAACTCTCATGTGCAGCCTCTGGATTCACCTTCAATAAGTACGCCATGAACTGGGTCCGCCAGGCTCCAGGAAAGGGTTTGGAATGGGTTGCT CGCATAAGAAGTAAATAATATGCAACATATTATGCCGATTCAGTGAAAGACAGGTTCACCATCTCCAGAGATGATTCAAAAACACTGCCTAT CTACAATGAACAACTTGGTCACCGTCTCCTCAGGTGGTGGTTCTGGCGGCGGCGGCTCCGGTGGTGGTTCTGGCGGCGGCGGCTCAGATATCCAGCTGACTCAGTCTCCAGCTTCC GGCCAAGGACTCTGGTCACCGTCTCCTCAGGTGGTGGTTCTGGCTTCTCAGGTGGTTCTGAACTTGTGACTACATATCCTCAGACTGTTGACTCAGGAACCT TCACTCACCGTATCACCTGGTGAACAGTCACACTACTTGTGGCTCTCGCCGTGATAGGTTCCTGCCCCCGTACTCTCTGCCGATTCTCAGGCTCCTCAGGCTCCCCCCTAAAACACAAAA CCAGGTCAGGCACCCCGGTCAGCGGCTCTAATAGGTGGCAGAAGTAGCAACCTCCGCTCGCCCCCGGCTCCCTCGCCGGGCTGACAAGGATGAACAAGGACAAAGGCAACACTCTCCC CTCACCCTTCAGGGATGACAGGCAGAGGATGAGGATGAGGCAGAATATTACTGTTCTATGGTACAGCAACCGCTGGGTGTTCGGGTTCGGTGAGGAACAAACTGAC T GTCCTACATCATCATCATCAT |

| SEQ ID NO: | Designation | Type | Sequence |
|---|---|---|---|
| 86 | VH-VL of murM2e-hBiTE × anti-CD3 | AA | EVQLLESGGGSVKPGGSLKLSCSASGFSLSTYAMSWVRQTPEKRLEWVASMSSGGSLYYPDTVKGRFTISRDTVKNIVYLQMSSLRSEDTAMYCVRGG YGTSYWGQGTTVTVSSGGGGSGGGGSGGGGSELLLTQTPLSLPVSLGDQASISCRSSQSIVHSIGDTYLEWYLQKPGQSPKLLIYKVSNRFSGVPDRFS GSGSGTDFTLKISRVEAEDLGIYYCFQGSHFPYTEGGGTKLEIKSGGGGSEVQLVESGGGLVQPGGSLKLSCAASGFTFNKYAMNWVRQAPGKLEWVA RIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEP SLT

The invention claimed is:

1. An antibody construct comprising:
   (a) a first human binding domain comprising a CDR-H1 comprising the amino acid sequence of SEQ ID NO: 1, a CDR-H2 as comprising the amino acid sequence of SEQ ID NO: 2, a CDR-H3 as comprising the amino acid sequence of SEQ ID NO: 3, a CDR-L1 as comprising the amino acid sequence of SEQ ID NO: 4, a CDR-L2 as comprising the amino acid sequence of SEQ ID NO: 5, and a CDR-L3 as comprising the amino acid sequence of SEQ ID NO: 6; and (b) a second binding domain specific for CD3.

2. The antibody construct according to claim 1, wherein the first binding domain comprises a VH region comprising the amino acid sequence of SEQ ID NO: 8, 16, 24, 32, 40, 48, 56, 64, or 72.

3. The antibody construct according to claim 1, wherein the first binding domain comprises a VL region comprising the amino acid sequence of SEQ ID NO: 10, 18, 26, 34, 42, 50, 58, 66, and or 74.

4. The antibody construct according to claim 1, wherein the first binding domain comprises a VH region and a VL region comprising the amino acid sequences selected from the group consisting of: SEQ ID NO:s 8 and 10, SEQ ID NO:s 16 and 18, SEQ ID NO:s 24 and 26, SEQ ID NO:s 32 and 34, SEQ ID NO:s 40 and 42, SEQ ID NO:s 48 and 50, SEQ ID NO:s 56 and 58, SEQ ID NO:s 64 and 66, and SEQ ID NO:s 72 and 74, respectively.

5. The antibody construct according to claim 1, wherein the antibody construct is in a format selected from the group consisting of (scFv)$_2$, scFv-single domain mAb, diabodies and oligomers thereof.

6. The antibody construct according to claim 1, wherein the first binding domain comprises the amino acid sequence of SEQ ID NO: 12, 20, 28, 36, 44, 52, 60, 68, or 76.

7. The antibody construct according to claim 1, wherein the second binding domain binds to human CD3, *Callithrix jacchus* CD3, *Saguinus Oedipus* CD3 or *Samiri sciureus* CD3 epsilon.

8. The antibody construct according to claim 7, comprising the amino acid sequence of SEQ ID NO: 14, 22, 30, 38, 46, 54, 62, 70, or 78.

9. A nucleic acid molecule comprising a nucleotide sequence encoding the antibody construct of claim 1.

10. A vector comprising the nucleic acid molecule of claim 9.

11. An isolated host cell transformed or transfected with the nucleic acid molecule of claim 9.

12. A process for producing an antibody construct, said process comprising culturing the host cell of claim 11 under conditions allowing the expression of the antibody construct encoded by the nucleic acid molecule and isolating the antibody construct.

13. A pharmaceutical composition comprising the antibody construct according to claim 1.

14. A method for treating or ameliorating an infection with an H5N1 or an H3N2 influenza A virus, comprising administering to a subject in need thereof an effective amount of the antibody construct according to claim 1.

15. The method according to claim 14, further comprising administering a reactive oxygen scavenger.

16. A pharmaceutical composition comprising the antibody construct according to claim 1 and a reactive oxygen scavenger.

17. A kit comprising the antibody construct according to claim 1.

18. An isolated host cell transformed or transfected with the vector of claim 10.

19. The method of claim 14, wherein the virus is an H5N1 influenza A virus.

20. The method of claim 14, wherein the virus is an H3N2 influenza A virus.

* * * * *

SEQUENCE LISTING

<160> NUMBER OF SEQ ID NOS: 91

<210> SEQ ID NO 1
<211> LENGTH: 5
<212> TYPE: PRT
<213> ORGANISM: artificial
<220> FEATURE:
<223> OTHER INFORMATION: CDR-H1 of Anti-M2e

<400> SEQUENCE: 1

Thr Tyr Ala Met Ser
1               5

<210> SEQ ID NO 2
<211> LENGTH: 16
<212> TYPE: PRT
<213> ORGANISM: artificial
<220> FEATURE:
<223> OTHER INFORMATION: CDR-H2 of Anti-M2e

<400> SEQUENCE: 2

Ser Met Ser Ser Gly Gly Ser Leu Tyr Tyr Pro Asp Thr Val Lys Gly
1               5                   10                  15

<210> SEQ ID NO 3
<211> LENGTH: 7
<212> TYPE: PRT
<213> ORGANISM: artificial
<220> FEATURE:
<223> OTHER INFORMATION: CDR-H3 of Anti-M2e

<400> SEQUENCE: 3

Gly Gly Tyr Gly Thr Ser Tyr
1               5

<210> SEQ ID NO 4
<211> LENGTH: 16
<212> TYPE: PRT
<213> ORGANISM: artificial
<220> FEATURE:
<223> OTHER INFORMATION: CDR-L1 of Anti-M2e

<400> SEQUENCE: 4

Arg Ser Ser Gln Ser Ile Val His Ser Ile Gly Asp Thr Tyr Leu Glu
1               5                   10                  15

<210> SEQ ID NO 5
<211> LENGTH: 7
<212> TYPE: PRT
<213> ORGANISM: artificial
<220> FEATURE:
<223> OTHER INFORMATION: CDR-L2 of Anti-M2e

<400> SEQUENCE: 5

Lys Val Ser Asn Arg Phe Ser
1               5

<210> SEQ ID NO 6
<211> LENGTH: 9
<212> TYPE: PRT
<213> ORGANISM: artificial
<220> FEATURE:
<223> OTHER INFORMATION: CDR-L3 of Anti-M2e

<400> SEQUENCE: 6

Phe Gln Gly Ser His Phe Pro Tyr Thr
1               5

<210> SEQ ID NO 7
<211> LENGTH: 726
<212> TYPE: DNA
<213> ORGANISM: artificial
<220> FEATURE:
<223> OTHER INFORMATION: VH of humM2e-hBiTE-1

<400> SEQUENCE: 7

```
gaggtgcagc tggtcgagtc tgggggaggc ttagtgcagc ctggagggtc cctgagactc    60
tcctgtgcag cctctggatt cactgtgagt acttatgcca tgtcttgggt tcgccagact   120
ccagagaaga ggctggaatg ggtcgcatcc atgagtagtg gtggtagtct ttattatcca   180
gacactgtga aggccgatt caccatctcc agagataatt ccaagaacac tgtgtacctg   240
caaatgaaca gtctgagggc tgaggacacg gccatgtatt actgtgtaag aggaggctac   300
ggaacttcgt actggggcca agggaccctg gtcaccgtct cctcaggtgg tggtggttct   360
ggcggcggcg gctccggtgg tggtggttct gacatcgtga tgacccaaac tccactctcc   420
ctgtctgtca ctcctggaga accggcctcc atctcttgca gatctagtca gagcattgtt   480
catagtattg gagacaccta tttagaatgg tacctgcaga aaccaggcca gtctccacag   540
ctcctgatct acaaagtttc caaccgattt tctggggtcc cagacaggtt cagtggcagt   600
ggatcaggga cagatttcac actcaagatc agcagagtgg aggctgagga tgtgggaatt   660
tattactgct ttcaaggttc acatttcccg tacacgttcg gacaggggac caagctggaa   720
ataaaa                                                              726
```

<210> SEQ ID NO 8
<211> LENGTH: 115
<212> TYPE: PRT
<213> ORGANISM: artificial
<220> FEATURE:
<223> OTHER INFORMATION: VH of humM2e-hBiTE-1

<400> SEQUENCE: 8

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Thr Tyr
             20                  25                  30

Ala Met Ser Trp Val Arg Gln Thr Pro Glu Lys Arg Leu Glu Trp Val
         35                  40                  45

Ala Ser Met Ser Ser Gly Gly Ser Leu Tyr Tyr Pro Asp Thr Val Lys
     50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Met Tyr Tyr Cys Val
                 85                  90                  95

Arg Gly Gly Tyr Gly Thr Ser Tyr Trp Gly Gln Gly Thr Leu Val Thr
            100                 105                 110

Val Ser Ser
        115
```

<210> SEQ ID NO 9
<211> LENGTH: 336
<212> TYPE: DNA
<213> ORGANISM: artificial
<220> FEATURE:
<223> OTHER INFORMATION: VL of humM2e-hBiTE-1

-continued

```
<400> SEQUENCE: 9
gacatcgtga tgacccaaac tccactctcc ctgtctgtca ctcctggaga accggcctcc      60
atctcttgca gatctagtca gagcattgtt catagtattg agacaccta tttagaatgg     120 tacctgcaga aaccaggcca gtctccacag ctcctgatct acaaagtttc caaccgattt     180
tctggggtcc cagacaggtt cagtggcagt ggatcaggga cagatttcac actcaagatc     240
agcagagtgg aggctgagga tgtgggaatt tattactgct ttcaaggttc acatttcccg     300
tacacgttcg gacaggggac caagctggaa ataaaa                              336

<210> SEQ ID NO 10
<211> LENGTH: 112
<212> TYPE: PRT
<213> ORGANISM: artificial
<220> FEATURE:
<223> OTHER INFORMATION: VL of humM2e-hBiTE-1

<400> SEQUENCE: 10

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Phe Gln Gly
                85                  90                  95

Ser His Phe Pro Tyr Thr Phe Gly Gln Gly Thr Lys Leu Glu Ile Lys
            100                 105                 110

<210> SEQ ID NO 11
<211> LENGTH: 726
<212> TYPE: DNA
<213> ORGANISM: artificial
<220> FEATURE:
<223> OTHER INFORMATION: VH-VL of humM2e-hBiTE-1

<400> SEQUENCE: 11
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga aggccgatt caccatctcc agagataatt ccaagaacac tgtgtacctg     240
caaatgaaca gtctgagggc tgaggacacg gccatgtatt actgtgtaag aggaggctac     300
ggaacttcgt actggggcca aggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg agacaccta tttagaatgg tacctgcaga aaccaggcca gtctccacag     540
ctcctgatct acaaagtttc caaccgattt tctggggtcc cagacaggtt cagtggcagt     600
ggatcaggga cagatttcac actcaagatc agcagagtgg aggctgagga tgtgggaatt     660
```

```
tattactgct tcaaggttc acatttcccg tacacgttcg acaggggac caagctggaa      720 ataaaa                                                               726
```

<210> SEQ ID NO 12
<211> LENGTH: 242
<212> TYPE: PRT
<213> ORGANISM: artificial
<220> FEATURE:
<223> OTHER INFORMATION: VH-VL of humM2e-hBiTE-1

<400> SEQUENCE: 12

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Ile Tyr Tyr Cys Phe
    210                 215                 220

Gln Gly Ser His Phe Pro Tyr Thr Phe Gly Gln Gly Thr Lys Leu Glu
225                 230                 235                 240

Ile Lys
```

<210> SEQ ID NO 13
<211> LENGTH: 1509
<212> TYPE: DNA
<213> ORGANISM: artificial
<220> FEATURE:
<223> OTHER INFORMATION: VH-VL of humM2e-hBiTE-1 x anti-CD3

<400> SEQUENCE: 13

```
gaggtgcagc tggtcgagtc tggggggaggc ttagtgcagc tggagggtc cctgagactc      60 tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacac tgtgtacctg     240
```

```
caaatgaaca gtctgagggc tgaggacacg gccatgtatt actgtgtaag aggaggctac      300
ggaacttcgt actggggcca agggaccctg gtcaccgtct cctcaggtgg tggtggttct      360
ggcggcggcg gctccggtgg tggtggttct gacatcgtga tgacccaaac tccactctcc      420
ctgtctgtca ctcctggaga accggcctcc atctcttgca gatctagtca gagcattgtt      480
catagtattg gagacaccta tttagaatgg tacctgcaga accaggcca gtctccacag       540 ctcctgatct acaaagtttc caaccgattt tctggggtcc agacaggtt cagtggcagt       600 ggatcaggga cagatttcac actcaagatc agcagagtgg aggctgagga tgtgggaatt      660
tattactgct ttcaaggttc acatttcccg tacacgttcg gacaggggac caagctggaa      720
ataaaatccg gaggtggtgg atccgaggtg cagctggtcg agtctggagg aggattggtg      780
cagcctggag ggtcattgaa actctcatgt gcagcctctg gattcacctt caataagtac      840
gccatgaact gggtccgcca ggctccagga aagggtttgg aatgggttgc tcgcataaga      900
agtaaatata ataattatgc aacatattat gccgattcag tgaaagacag gttcaccatc      960
tccagagatg attcaaaaaa cactgcctat ctacaaatga caacttgaa gactgaggac      1020 actgccgtgt actactgtgt gagacatggg aacttcggta atagctacat atcctactgg      1080
gcttactggg gccaagggac tctggtcacc gtctcctcag gtggtggtgg ttctggcggc      1140
ggcggctccg gtggtggtgg ttctcagact gttgtgactc aggaaccttc actcaccgta      1200
tcacctggtg aacagtcac actcacttgt ggctcctcga ctggggctgt acatctggc      1260 aactacccaa actgggtcca acaaaaacca ggtcaggcac cccgtggtct aataggtggg      1320
actaagttcc tcgcccccgg tactcctgcc agattctcag gctccctgct ggaggcaag      1380 gctgccctca ccctctcagg ggtacagcca gaggatgagg cagaatatta ctgtgttcta      1440
tggtacagca accgctgggt gttcggtgga ggaaccaaac tgactgtcct acatcatcac      1500
catcatcat                                                             1509
```

<210> SEQ ID NO 14
<211> LENGTH: 503
<212> TYPE: PRT
<213> ORGANISM: artificial
<220> FEATURE:
<223> OTHER INFORMATION: VH-VL of humM2e-hBiTE-1 x anti-CD3

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
```

```
                130             135             140
Pro Gly Glu Pro Ala Ser Ile Ser Cys Arg Ser Ser Gln Ser Ile Val
145             150             155             160

His Ser Ile Gly Asp Thr Tyr Leu Glu Trp Tyr Leu Gln Lys Pro Gly
                165             170             175

Gln Ser Pro Gln Leu Leu Ile Tyr Lys Val Ser Asn Arg Phe Ser Gly
            180             185             190

Val Pro Asp Arg Phe Ser Gly Ser Gly Ser Gly Thr Asp Phe Thr Leu
        195             200             205

Lys Ile Ser Arg Val Glu Ala Glu Asp Val Gly Ile Tyr Tyr Cys Phe
    210             215             220

Gln Gly Ser His Phe Pro Tyr Thr Phe Gly Gln Gly Thr Lys Leu Glu
225             230             235             240

Ile Lys Ser Gly Gly Gly Gly Ser Glu Val Gln Leu Val Glu Ser Gly
                245             250             255

Gly Gly Leu Val Gln Pro Gly Gly Ser Leu Lys Leu Ser Cys Ala Ala
                260             265             270

Ser Gly Phe Thr Phe Asn Lys Tyr Ala Met Asn Trp Val Arg Gln Ala
            275             280             285

Pro Gly Lys Gly Leu Glu Trp Val Ala Arg Ile Arg Ser Lys Tyr Asn
290             295             300

Asn Tyr Ala Thr Tyr Tyr Ala Asp Ser Val Lys Asp Arg Phe Thr Ile
305             310             315             320

Ser Arg Asp Asp Ser Lys Asn Thr Ala Tyr Leu Gln Met Asn Asn Leu
                325             330             335

Lys Thr Glu Asp Thr Ala Val Tyr Tyr Cys Val Arg His Gly Asn Phe
            340             345             350

Gly Asn Ser Tyr Ile Ser Tyr Trp Ala Tyr Trp Gly Gln Gly Thr Leu
        355             360             365

Val Thr Val Ser Ser Gly Gly Gly Gly Ser Gly Gly Gly Gly Ser Gly
    370             375             380

Gly Gly Ser Gln Thr Val Val Thr Gln Glu Pro Ser Leu Thr Val
385             390             395             400

Ser Pro Gly Gly Thr Val Thr Leu Thr Cys Gly Ser Ser Thr Gly Ala
                405             410             415

Val Thr Ser Gly Asn Tyr Pro Asn Trp Val Gln Gln Lys Pro Gly Gln
            420             425             430

Ala Pro Arg Gly Leu Ile Gly Gly Thr Lys Phe Leu Ala Pro Gly Thr
        435             440             445

Pro Ala Arg Phe Ser Gly Ser Leu Leu Gly Gly Lys Ala Ala Leu Thr
    450             455             460

Leu Ser Gly Val Gln Pro Glu Asp Glu Ala Glu Tyr Tyr Cys Val Leu
465             470             475             480

Trp Tyr Ser Asn Arg Trp Val Phe Gly Gly Gly Thr Lys Leu Thr Val
                485             490             495

Leu His His His His His His
            500

<210> SEQ ID NO 15
<211> LENGTH: 345
<212> TYPE: DNA
<213> ORGANISM: artificial
<220> FEATURE:
<223> OTHER INFORMATION: VH of humM2e-hBiTE-2
```

<400> SEQUENCE: 15

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacac tgtgtacctg     240
caaatgaaca gtctgagggc tgaggacacg gccatgtatt actgtgtaag aggaggctac     300
ggaacttcgt actggggcca agggaccctg gtcaccgtct cctca                    345
```

<210> SEQ ID NO 16
<211> LENGTH: 115
<212> TYPE: PRT
<213> ORGANISM: artificial
<220> FEATURE:
<223> OTHER INFORMATION: VH of humM2e-hBiTE-2

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser
        115
```

<210> SEQ ID NO 17
<211> LENGTH: 336
<212> TYPE: DNA
<213> ORGANISM: artificial
<220> FEATURE:
<223> OTHER INFORMATION: VL of humM2e-hBiTE-2

<400> SEQUENCE: 17

```
gacatcgtga tgacccaaac tccactctcc ctgtctgtca ctcctggaga accggcctcc      60
atctcttgca gatctagtca gagcattgtt catagtattg agacacccta tttagaatgg     120
tacctgcaga aaccaggcca gtctccacag ctcctgatct acaaagtttc caaccgattt     180
tctggggtcc cagacaggtt cagtggcagt ggatcaggga cagatttcac actcaagatc     240
agcagagtgg aggctgagga tgtgggagtt tattactgct ttcaaggttc acatttcccg     300
tacacgttcg gacaggggac caagctggaa ataaaa                              336
```

<210> SEQ ID NO 18
<211> LENGTH: 112
<212> TYPE: PRT
<213> ORGANISM: artificial
<220> FEATURE:
<223> OTHER INFORMATION: VL of humM2e-hBiTE-2

<400> SEQUENCE: 18

```
Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Gly
                85                  90                  95

Ser His Phe Pro Tyr Thr Phe Gly Gln Gly Thr Lys Leu Glu Ile Lys
            100                 105                 110
```

<210> SEQ ID NO 19
<211> LENGTH: 726
<212> TYPE: DNA
<213> ORGANISM: artificial
<220> FEATURE:
<223> OTHER INFORMATION: VH-VL of humM2e-hBiTE-2

<400> SEQUENCE: 19

```
gaggtgcagc tggtcgagtc tgggggaggc ttagtgcagc ctggagggtc cctgagactc    60
tcctgtgcag cctctggatt cactgtgagt acttatgcca tgtcttgggt tcgccagact   120
ccagagaaga ggctggaatg ggtcgcatcc atgagtagtg gtggtagtct ttattatcca   180
gacactgtga agggccgatt caccatctcc agagataatt ccaagaacac tgtgtacctg   240
caaatgaaca gtctgagggc tgaggacacg gccatgtatt actgtgtaag gaggctac    300
ggaacttcgt actggggcca aggaccctg gtcaccgtct cctcaggtgg tggtggttct   360
ggcggcggcg gctccggtgg tggtggttct gacatcgtga tgacccaaac tccactctcc   420
ctgtctgtca ctcctggaga accggcctcc atctcttgca gatctagtca gagcattgtt   480
catagtattg gagacaccta tttagaatgg tacctgcaga aaccaggcca gtctccacag   540
ctcctgatct acaaagtttc caaccgattt tctggggtcc cagacaggtt cagtggcagt   600
ggatcaggga cagatttcac actcaagatc agcagagtgg aggctgagga tgtgggagtt   660
tattactgct ttcaaggttc acatttcccg tacacgttcg gacaggggac caagctggaa   720
ataaaa                                                              726
```

<210> SEQ ID NO 20
<211> LENGTH: 242
<212> TYPE: PRT
<213> ORGANISM: artificial
<220> FEATURE:
<223> OTHER INFORMATION: VH-VL of humM2e-hBiTE-2

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60
```

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Met Tyr Tyr Cys Val
                 85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
130                 135                 140

Pro Gly Glu Pro Ala Ser Ile Ser Cys Arg Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
210                 215                 220

Gln Gly Ser His Phe Pro Tyr Thr Phe Gly Gln Gly Thr Lys Leu Glu
225                 230                 235                 240

Ile Lys

<210> SEQ ID NO 21
<211> LENGTH: 1509
<212> TYPE: DNA
<213> ORGANISM: artificial
<220> FEATURE:
<223> OTHER INFORMATION: VH-VL of humM2e-hBiTE-2 x anti-CD3

<400> SEQUENCE: 21
gaggtgcagc tggtcgagtc tgggggaggc ttagtgcagc tggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacac tgtgtacctg     240
caaatgaaca gtctgagggc tgaggacacg gccatgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga accaggcca gtctccacag     540
ctcctgatct acaaagtttc aaccgatt tctggggtcc agacaggtt cagtggcagt     600
ggatcaggga cagatttcac actcaagatc agcagagtgg aggctgagga tgtgggagtt     660
tattactgct ttcaaggttc acatttccg tacacgttcg gacaggggac caagctggaa     720
ataaaatccg gaggtggtgg atccgaggtg cagctggtcg agtctggagg aggattggtg     780
cagcctggag ggtcattgaa actctcatgt gcagcctctg gattcacctt caataagtac     840
gccatgaact gggtccgcca ggctccagga aagggtttgg aatgggttgc tcgcataaga     900
agtaaatata ataattatgc aacatattat gccgattcag tgaaagacag gttcaccatc     960
tccagagatg attcaaaaaa cactgcctat ctacaaatga caacttgaa gactgaggac    1020

-continued

```
actgccgtgt actactgtgt gagacatggg aacttcggta atagctacat atcctactgg    1080
gcttactggg gccaagggac tctggtcacc gtctcctcag gtggtggtgg ttctggcggc    1140
ggcggctccg gtggtggtgg ttctcagact gttgtgactc aggaaccttc actcaccgta    1200
tcacctggtg aacagtcac actcacttgt ggctcctcga ctggggctgt acatctggc     1260 aactacccaa actgggtcca acaaaaacca ggtcaggcac cccgtggtct aataggtggg    1320
actaagttcc tcgcccccgg tactcctgcc agattctcag gctccctgct tggaggcaag    1380
gctgccctca ccctctcagg ggtacagcca gaggatgagg cagaatatta ctgtgttcta    1440
tggtacagca accgctgggt gttcggtgga ggaaccaaac tgactgtcct acatcatcac    1500
catcatcat                                                              1509
```

<210> SEQ ID NO 22
<211> LENGTH: 503
<212> TYPE: PRT
<213> ORGANISM: artificial
<220> FEATURE:
<223> OTHER INFORMATION: VH-VL of humM2e-hBiTE-2 x anti-CD3

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270
```

Ser Gly Phe Thr Phe Asn Lys Tyr Ala Met Asn Trp Val Arg Gln Ala
    275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
            355                 360                 365

Val Thr Val Ser Ser Gly Gly Gly Ser Gly Gly Gly Ser Gly
    370                 375                 380

Gly Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
            435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500

<210> SEQ ID NO 23
<211> LENGTH: 345
<212> TYPE: DNA
<213> ORGANISM: artificial
<220> FEATURE:
<223> OTHER INFORMATION: VH of humM2e-hBiTE-3

<400> SEQUENCE: 23
gaggtgcagc tggtcgagtc tgggggaggc ttagtgcagc ctggagggtc cctgagactc    60
tcctgtgcag cctctggatt cactgtgagt acttatgcca tgtcttgggt tcgccagact   120
ccagagaaga ggctggaatg ggtcgcatcc atgagtagtg gtggtagtct ttattatcca   180
gacactgtga agggccgatt caccatctcc agagataatt ccaagaacac tgtgtacctg   240
caaatgaaca gtctgagggc tgaggacacg gccatgtatt actgtgtaag aggaggctac   300
ggaacttcgt actggggcca aggaccctg gtcaccgtct cctca                    345

<210> SEQ ID NO 24
<211> LENGTH: 115
<212> TYPE: PRT
<213> ORGANISM: artificial
<220> FEATURE:
<223> OTHER INFORMATION: VH of humM2e-hBiTE-3

<400> SEQUENCE: 24

Glu Val Gln Leu Val Glu Ser Gly Gly Gly Leu Val Gln Pro Gly Gly

```
             1               5              10              15

Ser Leu Arg Leu Ser Cys Ala Ala Ser Gly Phe Thr Val Ser Thr Tyr
                            20                  25                  30

Ala Met Ser Trp Val Arg Gln Thr Pro Glu Lys Arg Leu Glu Trp Val
                        35                  40                  45

Ala Ser Met Ser Ser Gly Gly Ser Leu Tyr Tyr Pro Asp Thr Val Lys
                    50                  55                  60

Gly Arg Phe Thr Ile Ser Arg Asp Asn Ser Lys Asn Thr Val Tyr Leu
            65                  70                  75                  80

Gln Met Asn Ser Leu Arg Ala Glu Asp Thr Ala Met Tyr Tyr Cys Val
                            85                  90                  95

Arg Gly Gly Tyr Gly Thr Ser Tyr Trp Gly Gln Gly Thr Leu Val Thr
                        100                 105                 110

Val Ser Ser
                    115

<210> SEQ ID NO 25
<211> LENGTH: 336
<212> TYPE: DNA
<213> ORGANISM: artificial
<220> FEATURE:
<223> OTHER INFORMATION: VL of humM2e-hBiTE-3

<400> SEQUENCE: 25
gacatcgtga tgacccaaac tccactctcc ctgtctgtca ctcctggaga accggcctcc       60
atctcttgca gatctagtca gagcattgtt catagtattg agacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tgtgggagtt tattactgct ttcaaggttc acatttcccg     300
tacacgttcg gacaggggac caagctggaa ataaaa                               336

<210> SEQ ID NO 26
<211> LENGTH: 112
<212> TYPE: PRT
<213> ORGANISM: artificial
<220> FEATURE:
<223> OTHER INFORMATION: VL of humM2e-hBiTE-3

<400> SEQUENCE: 26

Asp Ile Val Met Thr Gln Thr Pro Leu Ser Leu Ser Val Thr Pro Gly
1               5                  10                  15

Glu Pro Ala Ser Ile Ser Cys Arg Ser Ser Gln Ser Ile Val His Ser
                20                  25                  30

Ile Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Tyr Thr Phe Gly Gln Gly Thr Lys Leu Glu Ile Lys
                100                 105                 110

<210> SEQ ID NO 27
<211> LENGTH: 726
```

```
<212> TYPE: DNA
<213> ORGANISM: artificial
<220> FEATURE:
<223> OTHER INFORMATION: VH-VL of humM2e-hBiTE-3

<400> SEQUENCE: 27
gaggtgcagc tggtcgagtc tgggggaggc ttagtgcagc tggagggtc cctgagactc      60 tcctgtgcag cctctggatt cactgtgagt acttatgcca tgtcttgggt tcgccagact    120
ccagagaaga ggctggaatg ggtcgcatcc atgagtagtg gtggtagtct ttattatcca    180
gacactgtga agggccgatt caccatctcc agagataatt ccaagaacac tgtgtacctg    240
caaatgaaca gtctgagggc tgaggacacg gccatgtatt actgtgtaag gaggctac      300 ggaacttcgt actggggcca agggaccctg gtcaccgtct cctcaggtgg tggtggttct    360
ggcggcggcg gctccagtgg tggtggttct gacatcgtga tgacccaaac tccactctcc    420
ctgtctgtca ctcctggaga accggcctcc atctcttgca gatctagtca gagcattgtt    480
catagtattg gagacaccta tttagaatgg tacctgcaga accaggcca gtctccaaag     540 ctcctgatct acaaagtttc caaccgattt tctggggtcc agacaggtt cagtggcagt    600 ggatcaggga cagatttcac actcaagatc agcagagtgg aggctgagga tgtgggagtt    660
tattactgct ttcaaggttc acatttcccg tacacgttcg gacagggac caagctggaa    720 ataaaa                                                               726

<210> SEQ ID NO 28
<211> LENGTH: 242
<212> TYPE: PRT
<213> ORGANISM: artificial
<220> FEATURE:
<223> OTHER INFORMATION: VH-VL of humM2e-hBiTE-3

<400> SEQUENCE: 28
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Lys Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys

<210> SEQ ID NO 29
<211> LENGTH: 1509
<212> TYPE: DNA
<213> ORGANISM: artificial
<220> FEATURE:
<223> OTHER INFORMATION: VH-VL of humM2e-hBiTE-3 x anti-CD3

<400> SEQUENCE: 29

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacac tgtgtacctg     240
caaatgaaca gtctgagggc tgaggacacg gccatgtatt actgtgtaag aggaggctac     300
ggaacttcgt actggggcca agggaccctg gtcaccgtct cctcaggtgg tggtggttct     360
ggcggcggcg gctccagtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga aaccaggcca gtctccaaag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacaggggac caagctggaa     720
ataaaatccg gaggtggtgg atccgagtgc agctggtcg agtctggagg aggattggtg     780
cagcctggag ggtcattgaa actctcatgt gcagcctctg gattcacctt caataagtac     840
gccatgaact gggtccgcca ggctccagga aagggtttgg aatgggttgc tcgcataaga     900
agtaaaatat ataattatgc aacatattat gccgattcag tgaaagacag gttcaccatc     960
tccagagatg attcaaaaaa cactgcctat ctacaaatga acaacttgaa gactgaggac    1020
actgccgtgt actactgtgt gagacatggg aacttcggta atagctacat atcctactgg    1080
gcttactggg gccaagggac tctggtcacc gtctcctcag gtggtggtgg ttctggcggc    1140
ggcggctccg gtggtggtgg ttctcagact gttgtgactc aggaaccttc actcaccgta    1200
tcacctggtg aacagtcac actcacttgt ggctcctcga ctgggggctgt acatctggc    1260
aactacccaa actgggtcca acaaaaacca ggtcaggcac cccgtggtct aataggtggg    1320
actaagttcc tcgcccccgg tactcctgcc agattctcag gctccctgct tggaggcaag    1380
gctgccctca ccctctcagg ggtacagcca gaggatgagg cagaatatta ctgtgttcta    1440
tggtacagca accgctgggt gttcggtgga ggaaccaaac tgactgtcct acatcatcac    1500
catcatcat                                                           1509
```

<210> SEQ ID NO 30
<211> LENGTH: 503
<212> TYPE: PRT
<213> ORGANISM: artificial
<220> FEATURE:

<223> OTHER INFORMATION: VH-VL of humM2e-hBiTE-3 x anti-CD3

<400> SEQUENCE: 30

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Thr Tyr
            20                  25                  30
Ala Met Ser Trp Val Arg Gln Thr Pro Glu Lys Arg Leu Glu Trp Val
        35                  40                  45
Ala Ser Met Ser Ser Gly Gly Ser Leu Tyr Tyr Pro Asp Thr Val Lys
    50                  55                  60
Gly Arg Phe Thr Ile Ser Arg Asp Asn Ser Lys Asn Thr Val Tyr Leu
65                  70                  75                  80
Gln Met Asn Ser Leu Arg Ala Glu Asp Thr Ala Met Tyr Tyr Cys Val
                85                  90                  95
Arg Gly Gly Tyr Gly Thr Ser Tyr Trp Gly Gln Gly Thr Leu Val Thr
            100                 105                 110
Val Ser Ser Gly Gly Gly Gly Ser Gly Gly Gly Gly Ser Gly Gly
        115                 120                 125
Gly Ser Asp Ile Val Met Thr Gln Thr Pro Leu Ser Leu Ser Val Thr
    130                 135                 140
Pro Gly Glu Pro Ala Ser Ile Ser Cys Arg Ser Ser Gln Ser Ile Val
145                 150                 155                 160
His Ser Ile Gly Asp Thr Tyr Leu Glu Trp Tyr Leu Gln Lys Pro Gly
                165                 170                 175
Gln Ser Pro Lys Leu Leu Ile Tyr Lys Val Ser Asn Arg Phe Ser Gly
            180                 185                 190
Val Pro Asp Arg Phe Ser Gly Ser Gly Ser Gly Thr Asp Phe Thr Leu
        195                 200                 205
Lys Ile Ser Arg Val Glu Ala Glu Asp Val Gly Val Tyr Tyr Cys Phe
    210                 215                 220
Gln Gly Ser His Phe Pro Tyr Thr Phe Gly Gln Gly Thr Lys Leu Glu
225                 230                 235                 240
Ile Lys Ser Gly Gly Gly Gly Ser Glu Val Gln Leu Val Glu Ser Gly
                245                 250                 255
Gly Gly Leu Val Gln Pro Gly Gly Ser Leu Lys Leu Ser Cys Ala Ala
            260                 265                 270
Ser Gly Phe Thr Phe Asn Lys Tyr Ala Met Asn Trp Val Arg Gln Ala
        275                 280                 285
Pro Gly Lys Gly Leu Glu Trp Val Ala Arg Ile Arg Ser Lys Tyr Asn
    290                 295                 300
Asn Tyr Ala Thr Tyr Tyr Ala Asp Ser Val Lys Asp Arg Phe Thr Ile
305                 310                 315                 320
Ser Arg Asp Asp Ser Lys Asn Thr Ala Tyr Leu Gln Met Asn Asn Leu
                325                 330                 335
Lys Thr Glu Asp Thr Ala Val Tyr Tyr Cys Val Arg His Gly Asn Phe
            340                 345                 350
Gly Asn Ser Tyr Ile Ser Tyr Trp Ala Tyr Trp Gly Gln Gly Thr Leu
        355                 360                 365
Val Thr Val Ser Ser Gly Gly Gly Gly Ser Gly Gly Gly Gly Ser Gly
    370                 375                 380
Gly Gly Gly Ser Gln Thr Val Val Thr Gln Glu Pro Ser Leu Thr Val
385                 390                 395                 400
```

```
Ser Pro Gly Gly Thr Val Thr Leu Thr Cys Gly Ser Thr Gly Ala
            405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
            435                 440                 445

Pro Ala Arg Phe Ser Gly Ser Leu Leu Gly Gly Lys Ala Ala Leu Thr
450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500
```

<210> SEQ ID NO 31
<211> LENGTH: 345
<212> TYPE: DNA
<213> ORGANISM: artificial
<220> FEATURE:
<223> OTHER INFORMATION: VH of humM2e-hBiTE-4

<400> SEQUENCE: 31

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctggaatg ggtcgcatcc atgagtagtg gtggtagtct ttattatcca     180
gacactgtga agggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca agggaccctg gtcaccgtct cctca                    345
```

<210> SEQ ID NO 32
<211> LENGTH: 115
<212> TYPE: PRT
<213> ORGANISM: artificial
<220> FEATURE:
<223> OTHER INFORMATION: VH of humM2e-hBiTE-4

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser
        115
```

<210> SEQ ID NO 33

<211> LENGTH: 336
<212> TYPE: DNA
<213> ORGANISM: artificial
<220> FEATURE:
<223> OTHER INFORMATION: VL of humM2e-hBiTE-4

<400> SEQUENCE: 33

```
gacatcgtga tgacccaaac tccactctcc ctgtctgtca ctcctggaga accggcctcc        60
atctcttgca gatctagtca gagcattgtt catagtattg agacaccta tttagaatgg       120
tacctgcaga aaccaggcca gtctccacag ctcctgatct acaaagtttc caaccgattt       180
tctggggtcc cagacaggtt cagtggcagt ggatcaggga cagatttcac actcaagatc       240
agcagagtgg aggctgagga tgtgggaatt tattactgct ttcaaggttc acatttcccg       300
tacacgttcg gacaggggac caagctggaa ataaaa                                 336
```

<210> SEQ ID NO 34
<211> LENGTH: 112
<212> TYPE: PRT
<213> ORGANISM: artificial
<220> FEATURE:
<223> OTHER INFORMATION: VL of humM2e-hBiTE-4

<400> SEQUENCE: 34

```
Asp Ile Val Met Thr Gln Thr Pro Leu Ser Leu Ser Val Thr Pro Gly
1               5                   10                  15
Glu Pro Ala Ser Ile Ser Cys Arg Ser Ser Gln Ser Ile Val His Ser
            20                  25                  30
Ile Gly Asp Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Ile Tyr Tyr Cys Phe Gln Gly
                85                  90                  95
Ser His Phe Pro Tyr Thr Phe Gly Gln Gly Thr Lys Leu Glu Ile Lys
            100                 105                 110
```

<210> SEQ ID NO 35
<211> LENGTH: 726
<212> TYPE: DNA
<213> ORGANISM: artificial
<220> FEATURE:
<223> OTHER INFORMATION: VH-VL of humM2e-hBiTE-4

<400> SEQUENCE: 35

```
gaggtgcagc tggtcgagtc tgggggaggc ttagtgcagc ctggagggtc cctgagactc        60
tcctgtgcag cctctggatt cactgtgagt acttatgcca tgtcttgggt tcgccagact       120
ccagggaaga ggctggaatg ggtcgcatcc atgagtagtg gtggtagtct ttattatcca       180
gacactgtga agggccgatt caccatctcc agagatactt ccaagaacac tgtgtacctg       240
caaatgaaca gtctgagggc tgaggacacg gccgtgtatt actgtgtaag aggaggctac       300
ggaacttcgt actgggccca aggaccctg gtcaccgtct cctcaggtgg tggtggttct       360
ggcggcggcg gctccggtgg tggtggttct gacatcgtga tgacccaaac tccactctcc       420
ctgtctgtca ctcctggaga accggcctcc atctcttgca gatctagtca gagcattgtt       480
catagtattg agacaccta tttagaatgg tacctgcaga aaccaggcca gtctccacag       540
```

```
ctcctgatct acaaagtttc caaccgattt tctggggtcc cagacaggtt cagtggcagt    600
ggatcaggga cagatttcac actcaagatc agcagagtgg aggctgagga tgtgggaatt    660
tattactgct ttcaaggttc acatttcccg tacacgttcg gacagggga caagctggaa     720 ataaaa                                                                726
```

```
<210> SEQ ID NO 36
<211> LENGTH: 242
<212> TYPE: PRT
<213> ORGANISM: artificial
<220> FEATURE:
<223> OTHER INFORMATION: VH-VL of humM2e-hBiTE-4

<400> SEQUENCE: 36
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Val | Ser | Thr | Tyr |
| | | | 20 | | | | | 25 | | | | | 30 | | |
| Ala | Met | Ser | Trp | Val | Arg | Gln | Thr | Pro | Gly | Lys | Arg | Leu | Glu | Trp | Val |
| | | | 35 | | | | | 40 | | | | | 45 | | |
| Ala | Ser | Met | Ser | Ser | Gly | Gly | Ser | Leu | Tyr | Tyr | Pro | Asp | Thr | Val | Lys |
| | 50 | | | | | 55 | | | | | 60 | | | | |
| Gly | Arg | Phe | Thr | Ile | Ser | Arg | Asp | Thr | Ser | Lys | Asn | Thr | Val | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Val |
| | | | | 85 | | | | | 90 | | | | | 95 | |
| Arg | Gly | Gly | Tyr | Gly | Thr | Ser | Tyr | Trp | Gly | Gln | Gly | Thr | Leu | Val | Thr |
| | | | 100 | | | | | 105 | | | | | 110 | | |
| Val | Ser | Ser | Gly | Gly | Gly | Gly | Ser | Gly | Gly | Gly | Gly | Ser | Gly | Gly | Gly |
| | | 115 | | | | | 120 | | | | | 125 | | | |
| Gly | Ser | Asp | Ile | Val | Met | Thr | Gln | Thr | Pro | Leu | Ser | Leu | Ser | Val | Thr |
| 130 | | | | | 135 | | | | | 140 | | | | | |
| Pro | Gly | Glu | Pro | Ala | Ser | Ile | Ser | Cys | Arg | Ser | Ser | Gln | Ser | Ile | Val |
| 145 | | | | | 150 | | | | | 155 | | | | | 160 |
| His | Ser | Ile | Gly | Asp | Thr | Tyr | Leu | Glu | Trp | Tyr | Leu | Gln | Lys | Pro | Gly |
| | | | 165 | | | | | 170 | | | | | 175 | | |
| Gln | Ser | Pro | Gln | Leu | Leu | Ile | Tyr | Lys | Val | Ser | Asn | Arg | Phe | Ser | Gly |
| | | | 180 | | | | | 185 | | | | | 190 | | |
| Val | Pro | Asp | Arg | Phe | Ser | Gly | Ser | Gly | Ser | Gly | Thr | Asp | Phe | Thr | Leu |
| | | 195 | | | | | 200 | | | | | 205 | | | |
| Lys | Ile | Ser | Arg | Val | Glu | Ala | Glu | Asp | Val | Gly | Ile | Tyr | Tyr | Cys | Phe |
| 210 | | | | | 215 | | | | | 220 | | | | | |
| Gln | Gly | Ser | His | Phe | Pro | Tyr | Thr | Phe | Gly | Gln | Gly | Thr | Lys | Leu | Glu |
| 225 | | | | | 230 | | | | | 235 | | | | | 240 |
| Ile | Lys | | | | | | | | | | | | | | |

```
<210> SEQ ID NO 37
<211> LENGTH: 1509
<212> TYPE: DNA
<213> ORGANISM: artificial
<220> FEATURE:
<223> OTHER INFORMATION: VH-VL of humM2e-hBiTE-4 x anti-CD3

<400> SEQUENCE: 37
gaggtgcagc tggtcgagtc tgggggaggc ttagtgcagc ctggagggtc cctgagactc    60
tcctgtgcag cctctggatt cactgtgagt acttatgcca tgtcttgggt tcgccagact   120
```

| | |
|---|---|
| ccagggaaga ggctggaatg ggtcgcatcc atgagtagtg gtggtagtct ttattatcca | 180 |
| gacactgtga agggccgatt caccatctcc agagatactt ccaagaacac tgtgtacctg | 240 |
| caaatgaaca gtctgagggc tgaggacacg gccgtgtatt actgtgtaag aggaggctac | 300 |
| ggaacttcgt actggggcca agggaccctg gtcaccgtct cctcaggtgg tggtggttct | 360 |
| ggcggcggcg gctccggtgg tggtggttct gacatcgtga tgacccaaac tccactctcc | 420 |
| ctgtctgtca ctcctggaga accggcctcc atctcttgca gatctagtca gagcattgtt | 480 |
| catagtattg gagacaccta tttagaatgg tacctgcaga aaccaggcca gtctccacag | 540 |
| ctcctgatct acaaagtttc caaccgattt tctggggtcc cagacaggtt cagtggcagt | 600 |
| ggatcaggga cagatttcac actcaagatc agcagagtgg aggctgagga tgtgggaatt | 660 |
| tattactgct ttcaaggttc acatttcccg tacacgttcg gacagggac caagctggaa | 720 |
| ataaaatccg gaggtggtgg atccgagtgc agctggtcg agtctggagg aggattggtg | 780 |
| cagcctggag ggtcattgaa actctcatgt gcagcctctg gattcacctt caataagtac | 840 |
| gccatgaact gggtccgcca ggctccagga aagggtttgg aatgggttgc tcgcataaga | 900 |
| agtaaatata ataattatgc aacatattat gccgattcag tgaaagacag gttcaccatc | 960 |
| tccagagatg attcaaaaaa cactgcctat ctacaaatga caacttgaa gactgaggac | 1020 |
| actgccgtgt actactgtgt gagacatggg aacttcggta atagctacat atcctactgg | 1080 |
| gcttactggg gccaagggac tctggtcacc gtctcctcag gtggtggtgg ttctggcggc | 1140 |
| ggcggctccg gtggtggtgg ttctcagact gttgtgactc aggaaccttc actcaccgta | 1200 |
| tcacctggtg aacagtcac actcacttgt ggctcctcga ctggggctgt acatctggc | 1260 |
| aactacccaa actgggtcca acaaaaacca ggtcaggcac cccgtggtct aataggtggg | 1320 |
| actaagttcc tcgcccccgg tactcctgcc agattctcag gctccctgct ggaggcaag | 1380 |
| gctgccctca ccctctcagg ggtacagcca aggatgagg cagaatatta ctgtgttcta | 1440 |
| tggtacagca accgctgggt gttcggtgga ggaaccaaac tgactgtcct acatcatcac | 1500 |
| catcatcat | 1509 |

<210> SEQ ID NO 38
<211> LENGTH: 503
<212> TYPE: PRT
<213> ORGANISM: artificial
<220> FEATURE:
<223> OTHER INFORMATION: VH-VL of humM2e-hBiTE-4 x anti-CD3

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Ser Gly Gly Gly Ser Gly Gly
        115                 120                 125

Gly Ser Asp Ile Val Met Thr Gln Thr Pro Leu Ser Leu Ser Val Thr
130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Ile Tyr Tyr Cys Phe
210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Met Asn Trp Val Arg Gln Ala
        275                 280                 285

Pro Gly Lys Gly Leu Glu Trp Val Ala Arg Ile Arg Ser Lys Tyr Asn
290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Gly Ser Gly
370                 375                 380

Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
        435                 440                 445

Pro Ala Arg Phe Ser Gly Ser Leu Leu Gly Gly Lys Ala Ala Leu Thr
450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500

<210> SEQ ID NO 39
<211> LENGTH: 345
<212> TYPE: DNA

<213> ORGANISM: artificial
<220> FEATURE:
<223> OTHER INFORMATION: VH of humM2e-hBiTE-5

<400> SEQUENCE: 39

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctggaatg ggtcgcatcc atgagtagtg gtggtagtct ttattatcca     180
gacactgtga agggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca aggaccctg gtcaccgtct cctca                     345
```

<210> SEQ ID NO 40
<211> LENGTH: 115
<212> TYPE: PRT
<213> ORGANISM: artificial
<220> FEATURE:
<223> OTHER INFORMATION: VH of humM2e-hBiTE-5

<400> SEQUENCE: 40

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Thr Tyr
            20                  25                  30
Ala Met Ser Trp Val Arg Gln Thr Pro Gly Lys Arg Leu Glu Trp Val
        35                  40                  45
Ala Ser Met Ser Ser Gly Gly Ser Leu Tyr Tyr Pro Asp Thr Val Lys
    50                  55                  60
Gly Arg Phe Thr Ile Ser Arg Asp Thr Ser Lys Asn Thr Val Tyr Leu
65                  70                  75                  80
Gln Met Asn Ser Leu Arg Ala Glu Asp Thr Ala Val Tyr Tyr Cys Val
                85                  90                  95
Arg Gly Gly Tyr Gly Thr Ser Tyr Trp Gly Gln Gly Thr Leu Val Thr
            100                 105                 110
Val Ser Ser
        115

<210> SEQ ID NO 41
<211> LENGTH: 336
<212> TYPE: DNA
<213> ORGANISM: artificial
<220> FEATURE:
<223> OTHER INFORMATION: VL of humM2e-hBiTE-5

<400> SEQUENCE: 41

```
gacatcgtga tgacccaaac tccactctcc ctgtctgtca ctcctggaga accggcctcc      60
atctcttgca gatctagtca gagcattgtt catagtattg gagacaccta tttagaatgg     120
tacctgcaga accaggcca gtctccacag ctcctgatct caaagtttc caaccgattt      180
tctggggtcc cagacaggtt cagtggcagt ggatcaggga cagatttcac actcaagatc     240
agcagagtgg aggctgagga tgtgggagtt tattactgct ttcaaggttc acatttcccg     300
tacacgttcg gacaggggac caagctggaa ataaaa                              336
```

<210> SEQ ID NO 42
<211> LENGTH: 112
<212> TYPE: PRT
<213> ORGANISM: artificial

```
<220> FEATURE:
<223> OTHER INFORMATION: VL of humM2e-hBiTE-5

<400> SEQUENCE: 42

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Tyr Thr Phe Gly Gln Gly Thr Lys Leu Glu Ile Lys
            100                 105                 110

<210> SEQ ID NO 43
<211> LENGTH: 726
<212> TYPE: DNA
<213> ORGANISM: artificial
<220> FEATURE:
<223> OTHER INFORMATION: VH-VL of humM2e-hBiTE-5

<400> SEQUENCE: 43
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctggaatg ggtcgcatcc atgagtagtg gtggtagtct ttattatcca     180
gacactgtga agggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga aaccaggcca gtctccacag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacagggac caagctggaa     720 ataaaa                                                                726

<210> SEQ ID NO 44
<211> LENGTH: 242
<212> TYPE: PRT
<213> ORGANISM: artificial
<220> FEATURE:
<223> OTHER INFORMATION: VH-VL of humM2e-hBiTE-5

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
```

|  | 35 |  |  | 40 |  |  |  | 45 |  |  |
|---|---|---|---|---|---|---|---|---|---|---|

Ala Ser Met Ser Ser Gly Gly Ser Leu Tyr Tyr Pro Asp Thr Val Lys
 50                     55                      60

Gly Arg Phe Thr Ile Ser Arg Asp Thr Ser Lys Asn Thr Val Tyr Leu
 65                     70                      75                      80

Gln Met Asn Ser Leu Arg Ala Glu Asp Thr Ala Val Tyr Tyr Cys Val
                         85                      90                      95

Arg Gly Gly Tyr Gly Thr Ser Tyr Trp Gly Gln Gly Thr Leu Val Thr
                100                     105                     110

Val Ser Ser Gly Gly Gly Gly Ser Gly Gly Gly Gly Ser Gly Gly Gly
        115                     120                     125

Gly Ser Asp Ile Val Met Thr Gln Thr Pro Leu Ser Leu Ser Val Thr
130                     135                     140

Pro Gly Glu Pro Ala Ser Ile Ser Cys Arg Ser Ser Gln Ser Ile Val
145                     150                     155                     160

His Ser Ile Gly Asp Thr Tyr Leu Glu Trp Tyr Leu Gln Lys Pro Gly
                165                     170                     175

Gln Ser Pro Gln Leu Leu Ile Tyr Lys Val Ser Asn Arg Phe Ser Gly
                180                     185                     190

Val Pro Asp Arg Phe Ser Gly Ser Gly Ser Gly Thr Asp Phe Thr Leu
                195                     200                     205

Lys Ile Ser Arg Val Glu Ala Glu Asp Val Gly Val Tyr Tyr Cys Phe
210                     215                     220

Gln Gly Ser His Phe Pro Tyr Thr Phe Gly Gln Gly Thr Lys Leu Glu
225                     230                     235                     240

Ile Lys

<210> SEQ ID NO 45
<211> LENGTH: 1509
<212> TYPE: DNA
<213> ORGANISM: artificial
<220> FEATURE:
<223> OTHER INFORMATION: VH-VL of humM2e-hBiTE-5 x anti-CD3

<400> SEQUENCE: 45

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctggaatg ggtcgcatcc atgagtagtg gtggtagtct ttattatcca     180
gacactgtga aggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga aaccaggcca gtctccacag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacagggac caagctggaa     720
ataaaatccg gaggtggtgg atccgaggtg cagctggtcg agtctggagg aggattggtg     780
cagcctggag ggtcattgaa actctcatgt gcagcctctg gattcacctt caataagtac     840
gccatgaact gggtccgcca ggctccagga aagggtttgg aatgggttgc tcgcataaga     900
```

```
agtaaatata ataattatgc aacatattat gccgattcag tgaaagacag gttcaccatc    960
tccagagatg attcaaaaaa cactgcctat ctacaaatga caacttgaa gactgaggac   1020 actgccgtgt actactgtgt gagacatggg aacttcggta atagctacat atcctactgg   1080
gcttactggg gccaagggac tctggtcacc gtctcctcag gtggtggtgg ttctggcggc   1140
ggcggctccg gtggtggtgg ttctcagact gttgtgactc aggaaccttc actcaccgta   1200
tcacctggtg aacagtcac actcacttgt ggctcctcga ctggggctgt acatctggc   1260 aactacccaa actgggtcca acaaaaacca ggtcaggcac cccgtggtct aataggtggg   1320
actaagttcc tcgcccccgg tactcctgcc agattctcag gctccctgct tggaggcaag   1380
gctgccctca ccctctcagg ggtacagcca gaggatgagg cagaatatta ctgtgttcta   1440
tggtacagca accgctgggt gttcggtgga ggaaccaaac tgactgtcct acatcatcac   1500
catcatcat                                                          1509

<210> SEQ ID NO 46
<211> LENGTH: 503
<212> TYPE: PRT
<213> ORGANISM: artificial
<220> FEATURE:
<223> OTHER INFORMATION: VH-VL of humM2e-hBiTE-5 x anti-CD3

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
```

```
                245                 250                 255
Gly Gly Leu Val Gln Pro Gly Gly Ser Leu Lys Leu Ser Cys Ala Ala
            260                 265                 270

Ser Gly Phe Thr Phe Asn Lys Tyr Ala Met Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
        435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500

<210> SEQ ID NO 47
<211> LENGTH: 345
<212> TYPE: DNA
<213> ORGANISM: artificial
<220> FEATURE:
<223> OTHER INFORMATION: VH of humM2e-hBiTE-6

<400> SEQUENCE: 47
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctgaatg gtcgcatcc atgagtagtg gtggtagtct ttattatcca       180
gacactgtga agggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca agggaccctg gtcaccgtct cctca                     345

<210> SEQ ID NO 48
<211> LENGTH: 115
<212> TYPE: PRT
<213> ORGANISM: artificial
<220> FEATURE:
<223> OTHER INFORMATION: VH of humM2e-hBiTE-6
```

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser
        115

<210> SEQ ID NO 49
<211> LENGTH: 336
<212> TYPE: DNA
<213> ORGANISM: artificial
<220> FEATURE:
<223> OTHER INFORMATION: VL of humM2e-hBiTE-6

<400> SEQUENCE: 49
gacatcgtga tgacccaaac tccactctcc ctgtctgtca ctcctggaga accggcctcc      60
atctcttgca gatctagtca gagcattgtt catagtattg agacacccta tttagaatgg     120
tacctgcaga accaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tgtgggagtt tattactgct ttcaaggttc acatttcccg     300
tacacgttcg gacaggggac caagctggaa ataaaa                                336

<210> SEQ ID NO 50
<211> LENGTH: 112
<212> TYPE: PRT
<213> ORGANISM: artificial
<220> FEATURE:
<223> OTHER INFORMATION: VL of humM2e-hBiTE-6

<400> SEQUENCE: 50

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Tyr Thr Phe Gly Gln Gly Thr Lys Leu Glu Ile Lys
            100                 105                 110

<210> SEQ ID NO 51
<211> LENGTH: 726
<212> TYPE: DNA
<213> ORGANISM: artificial
<220> FEATURE:
<223> OTHER INFORMATION: VH-VL of humM2e-hBiTE-6

<400> SEQUENCE: 51

```
gaggtgcagc tggtcgagtc tgggggaggc ttagtgcagc tggagggtc cctgagactc      60
tcctgtgcag cctctggatt cactgtgagt acttatgcca tgtcttgggt tcgccagact    120
ccagggaaga ggctgaatg ggtcgcatcc atgagtagtg gtggtagtct ttattatcca    180
gacactgtga agggccgatt caccatctcc agagatactt ccaagaacac tgtgtacctg   240
caaatgaaca gtctgagggc tgaggacacg gccgtgtatt actgtgtaag aggaggctac   300
ggaacttcgt actggggcca agggaccctg gtcaccgtct cctcaggtgg tggtggttct   360
ggcggcggcg gctccggtgg tggtggttct gacatcgtga tgacccaaac tccactctcc   420
ctgtctgtca ctcctggaga accggcctcc atctcttgca gatctagtca gagcattgtt   480
catagtattg gagacaccta tttagaatgg tacctgcaga accaggcca gtctccaaag   540
ctcctgatct acaaagtttc caaccgattt tctggggtcc cagacaggtt cagtggcagt   600
ggatcaggga cagatttcac actcaagatc agcagagtgg aggctgagga tgtgggagtt   660
tattactgct ttcaaggttc acatttcccg tacacgttcg gacaggggac caagctggaa   720
ataaaa                                                               726
```

<210> SEQ ID NO 52
<211> LENGTH: 242
<212> TYPE: PRT
<213> ORGANISM: artificial
<220> FEATURE:
<223> OTHER INFORMATION: VH-VL of humM2e-hBiTE-6

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175
```

```
Gln Ser Pro Lys Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys

<210> SEQ ID NO 53
<211> LENGTH: 1509
<212> TYPE: DNA
<213> ORGANISM: artificial
<220> FEATURE:
<223> OTHER INFORMATION: VH-VL of humM2e-hBiTE-6 x anti-CD3

<400> SEQUENCE: 53
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagggaaga ggctggaatg ggtcgcatcc atgagtagtg gtggtagtct ttattatcca     180
gacactgtga aggccgatt caccatctcc agagatactt ccaagaacac tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga accaggcca gtctccaaag     540 ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacagggac caagctggaa     720 ataaaatccg gaggtggtgg atccgagtg cagctggtcg agtctggagg aggattggtg     780
cagcctggag ggtcattgaa actctcatgt gcagcctctg gattcaccTT caataagtac     840
gccatgaact gggtccgcca ggctccagga aagggtttgg aatgggttgc tcgcataaga     900
agtaaatata taattatgc aacatattat gccgattcag tgaaagacag gttcaccatc     960
tccagagatg attcaaaaaa cactgcctat ctacaaatga caacttgaa gactgaggac    1020 actgccgtgt actactgtgt gagacatggg aacttcggta atagctacat atcctactgg    1080
gcttactggg gccaagggac tctggtcacc gtctcctcag gtggtggtgg ttctggcggc    1140
ggcggctccg gtggtggtgg ttctcagact gttgtgactc aggaaccttc actcaccgta    1200
tcacctggtg aacagtcac actcacttgt ggctcctcga ctgggctgt acatctggc     1260 aactacccaa actgggtcca acaaaaacca ggtcaggcac cccgtggtct aataggtggg    1320
actaagttcc tcgccccgg tactcctgcc agattctcag ctccctgct tggaggcaag    1380 gctgccctca ccctctcagg ggtacagcca gaggatgagg cagaatatta ctgtgttcta    1440
tggtacagca accgctgggt gttcggtgga ggaaccaaac tgactgtcct acatcatcac    1500
catcatcat                                                          1509

<210> SEQ ID NO 54
```

```
<211> LENGTH: 503
<212> TYPE: PRT
<213> ORGANISM: artificial
<220> FEATURE:
<223> OTHER INFORMATION: VH-VL of humM2e-hBiTE-6 x anti-CD3

<400> SEQUENCE: 54
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Gly Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Val
            85                  90                  95

Arg Gly Gly Tyr Gly Thr Ser Tyr Trp Gly Gln Gly Thr Leu Val Thr
        100                 105                 110

Val Ser Ser Gly Gly Gly Gly Ser Gly Gly Gly Gly Ser Gly Gly Gly
    115                 120                 125

Gly Ser Asp Ile Val Met Thr Gln Thr Pro Leu Ser Leu Ser Val Thr
130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
            165                 170                 175

Gln Ser Pro Lys Leu Leu Ile Tyr Lys Val Ser Asn Arg Phe Ser Gly
        180                 185                 190

Val Pro Asp Arg Phe Ser Gly Ser Gly Ser Gly Thr Asp Phe Thr Leu
    195                 200                 205

Lys Ile Ser Arg Val Glu Ala Glu Asp Val Gly Val Tyr Tyr Cys Phe
210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
            245                 250                 255

Gly Gly Leu Val Gln Pro Gly Gly Ser Leu Lys Leu Ser Cys Ala Ala
        260                 265                 270

Ser Gly Phe Thr Phe Asn Lys Tyr Ala Met Asn Trp Val Arg Gln Ala
    275                 280                 285

Pro Gly Lys Gly Leu Glu Trp Val Ala Arg Ile Arg Ser Lys Tyr Asn
290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
            325                 330                 335

Lys Thr Glu Asp Thr Ala Val Tyr Tyr Cys Val Arg His Gly Asn Phe
        340                 345                 350

Gly Asn Ser Tyr Ile Ser Tyr Trp Ala Tyr Trp Gly Gln Gly Thr Leu
    355                 360                 365

Val Thr Val Ser Ser Gly Gly Gly Gly Ser Gly Gly Gly Gly Ser Gly
370                 375                 380

Gly Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
            405                 410                 415

Val Thr Ser Gly Asn Tyr Pro Asn Trp Val Gln Gln Lys Pro Gly Gln
        420                 425                 430

Ala Pro Arg Gly Leu Ile Gly Gly Thr Lys Phe Leu Ala Pro Gly Thr
    435                 440                 445

Pro Ala Arg Phe Ser Gly Ser Leu Leu Gly Gly Lys Ala Ala Leu Thr
450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
        500

<210> SEQ ID NO 55
<211> LENGTH: 345
<212> TYPE: DNA
<213> ORGANISM: artificial
<220> FEATURE:
<223> OTHER INFORMATION: VH of humM2e-hBiTE-7

<400> SEQUENCE: 55
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacat tgtgtacctg     240
caaatgaaca gtctgagggc tgaggacacg gccgtgtatt actgtgtaag aggaggctac     300
ggaacttcgt actggggcca agggaccctg gtcaccgtct cctca                    345

<210> SEQ ID NO 56
<211> LENGTH: 115
<212> TYPE: PRT
<213> ORGANISM: artificial
<220> FEATURE:
<223> OTHER INFORMATION: VH of humM2e-hBiTE-7

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser

<210> SEQ ID NO 57
<211> LENGTH: 336
<212> TYPE: DNA
<213> ORGANISM: artificial
<220> FEATURE:
<223> OTHER INFORMATION: VL of humM2e-hBiTE-7

<400> SEQUENCE: 57

```
gacatcgtga tgacccaaac tccactctcc ctgtctgtca ctcctggaga accggcctcc      60
atctcttgca gatctagtca gagcattgtt catagtattg agacaccta tttagaatgg     120
tacctgcaga aaccaggcca gtctccacag ctcctgatct acaaagtttc caaccgattt     180
tctggggtcc cagacaggtt cagtggcagt ggatcaggga cagatttcac actcaagatc     240
agcagagtgg aggctgagga tgtgggaatt tattactgct ttcaaggttc acatttcccg     300
tacacgttcg gacaggggac caagctggaa ataaaa                               336
```

<210> SEQ ID NO 58
<211> LENGTH: 112
<212> TYPE: PRT
<213> ORGANISM: artificial
<220> FEATURE:
<223> OTHER INFORMATION: VL of humM2e-hBiTE-7

<400> SEQUENCE: 58

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Phe Gln Gly
                85                  90                  95

Ser His Phe Pro Tyr Thr Phe Gly Gln Gly Thr Lys Leu Glu Ile Lys
            100                 105                 110

<210> SEQ ID NO 59
<211> LENGTH: 726
<212> TYPE: DNA
<213> ORGANISM: artificial
<220> FEATURE:
<223> OTHER INFORMATION: VH-VL of humM2e-hBiTE-7

<400> SEQUENCE: 59

```
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacat tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
```

```
ctgtctgtca ctcctggaga accggcctcc atctcttgca gatctagtca gagcattgtt    480
catagtattg agacaccta tttagaatgg tacctgcaga aaccaggcca gtctccacag    540
ctcctgatct acaaagtttc caaccgattt tctggggtcc cagacaggtt cagtggcagt    600
ggatcaggga cagatttcac actcaagatc agcagagtgg aggctgagga tgtgggaatt    660
tattactgct ttcaaggttc acatttcccg tacacgttcg gacagggggac caagctggaa    720 ataaaa                                                                726
```

```
<210> SEQ ID NO 60
<211> LENGTH: 242
<212> TYPE: PRT
<213> ORGANISM: artificial
<220> FEATURE:
<223> OTHER INFORMATION: VH-VL of humM2e-hBiTE-7

<400> SEQUENCE: 60
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Ile Tyr Tyr Cys Phe
    210                 215                 220

Gln Gly Ser His Phe Pro Tyr Thr Phe Gly Gln Gly Thr Lys Leu Glu
225                 230                 235                 240

Ile Lys

```
<210> SEQ ID NO 61
<211> LENGTH: 1509
<212> TYPE: DNA
<213> ORGANISM: artificial
<220> FEATURE:
<223> OTHER INFORMATION: VH-VL of humM2e-hBiTE-7 x anti-CD3

<400> SEQUENCE: 61
```

```
gaggtgcagc tggtcgagtc tgggggaggc ttagtgcagc tggagggtc cctgagactc      60 tcctgtgcag cctctggatt cactgtgagt acttatgcca tgtcttgggt tcgccagact    120
ccagagaaga ggctggaatg ggtcgcatcc atgagtagtg gtggtagtct ttattatcca    180
gacactgtga agggccgatt caccatctcc agagataatt ccaagaacat tgtgtacctg    240
caaatgaaca gtctgagggc tgaggacacg gccgtgtatt actgtgtaag aggaggctac    300
ggaacttcgt actggggcca agggaccctg gtcaccgtct cctcaggtgg tggtggttct    360
ggcggcggcg gctccggtgg tggtggttct gacatcgtga tgacccaaac tccactctcc    420
ctgtctgtca ctcctggaga accggcctcc atctcttgca gatctagtca gagcattgtt    480
catagtattg gagacaccta tttagaatgg tacctgcaga accaggcca gtctccacag    540 ctcctgatct acaaagtttc caaccgattt tctggggtcc cagacaggtt cagtggcagt    600
ggatcaggga cagatttcac actcaagatc agcagagtgg aggctgagga tgtgggaatt    660
tattactgct ttcaaggttc acatttcccg tacacgttcg gcaggggac caagctggaa    720 ataaaatccg gaggtggtgg atccgagtgc agctggtcg agtctggagg aggattggtg    780
cagcctggag ggtcattgaa actctcatgt gcagcctctg gattcacctt caataagtac    840
gccatgaact gggtccgcca ggctccagga aagggtttgg aatgggttgc tcgcataaga    900
agtaaatata ataattatgc aacatattat gccgattcag tgaaagacag gttcaccatc    960
tccagagatg attcaaaaaa cactgcctat ctacaaatga acaacttgaa gactgaggac   1020
actgccgtgt actactgtgt gagacatggg aacttcggta atagctacat atcctactgg   1080
gcttactggg gccaagggac tctggtcacc gtctcctcag gtggtggtgg ttctggcggc   1140
ggcggctccg gtggtggtgg ttctcagact gttgtgactc aggaaccttc actcaccgta   1200
tcacctggtg aacagtcac actcacttgt ggctcctcga ctggggctgt tacatctggc   1260
aactacccaa actgggtcca caaaaaacca ggtcaggcac cccgtggtct aataggtggg   1320
actaagttcc tcgccccgg tactcctgcc agattctcag gctccctgct ggaggcaag   1380 gctgccctca ccctctcagg ggtacagcca gaggatgagg cagaatatta ctgtgttcta   1440
tggtacagca accgctgggt gttcggtgga ggaaccaaac tgactgtcct acatcatcac   1500
catcatcat                                                           1509
```

<210> SEQ ID NO 62
<211> LENGTH: 503
<212> TYPE: PRT
<213> ORGANISM: artificial
<220> FEATURE:
<223> OTHER INFORMATION: VH-VL of humM2e-hBiTE-7 x anti-CD3

<400> SEQUENCE: 62

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95
```

```
Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Ile Tyr Tyr Cys Phe
    210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Met Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
        435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500
```

<210> SEQ ID NO 63
<211> LENGTH: 345
<212> TYPE: DNA
<213> ORGANISM: artificial
<220> FEATURE:
<223> OTHER INFORMATION: VH of humM2e-hBiTE-8

<400> SEQUENCE: 63

```
gaggtgcagc tggtcgagtc tggggggaggc ttagtgcagc ctggagggtc cctgagactc    60
tcctgtgcag cctctggatt cactgtgagt acttatgcca tgtcttgggt tcgccagact   120
ccagagaaga ggctggaatg ggtcgcatcc atgagtagtg gtggtagtct ttattatcca   180
gacactgtga agggccgatt caccatctcc agagataatt ccaagaacat tgtgtacctg   240
caaatgaaca gtctgagggc tgaggacacg gccgtgtatt actgtgtaag aggaggctac   300
ggaacttcgt actggggcca aggaccctg gtcaccgtct cctca                    345
```

<210> SEQ ID NO 64
<211> LENGTH: 115
<212> TYPE: PRT
<213> ORGANISM: artificial
<220> FEATURE:
<223> OTHER INFORMATION: VH of humM2e-hBiTE-8

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser
        115
```

<210> SEQ ID NO 65
<211> LENGTH: 336
<212> TYPE: DNA
<213> ORGANISM: artificial
<220> FEATURE:
<223> OTHER INFORMATION: VL of humM2e-hBiTE-8

<400> SEQUENCE: 65

```
gacatcgtga tgacccaaac tccactctcc ctgtctgtca ctcctggaga accggcctcc    60
atctcttgca gatctagtca gagcattgtt catagtattg gagacaccta tttagaatgg   120
tacctgcaga aaccaggcca gtctccacag ctcctgatct acaaagtttc caaccgattt   180
tctggggtcc cagacaggtt cagtggcagt ggatcaggga cagatttcac actcaagatc   240
agcagagtgg aggctgagga tgtgggagtt tattactgct ttcaaggttc acatttcccg   300
tacacgttcg gacaggggac caagctggaa ataaaa                             336
```

```
<210> SEQ ID NO 66
<211> LENGTH: 112
<212> TYPE: PRT
<213> ORGANISM: artificial
<220> FEATURE:
<223> OTHER INFORMATION: VL of humM2e-hBiTE-8

<400> SEQUENCE: 66

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Tyr Thr Phe Gly Gln Gly Thr Lys Leu Glu Ile Lys
            100                 105                 110

<210> SEQ ID NO 67
<211> LENGTH: 726
<212> TYPE: DNA
<213> ORGANISM: artificial
<220> FEATURE:
<223> OTHER INFORMATION: VH-VL of humM2e-hBiTE-8

<400> SEQUENCE: 67
gaggtgcagc tggtcgagtc tggggggaggc ttagtgcagc ctggagggtc cctgagactc        60
tcctgtgcag cctctggatt cactgtgagt acttatgcca tgtcttgggt tcgccagact       120
ccagagaaga ggctggaatg ggtcgcatcc atgagtagtg gtggtagtct ttattatcca       180
gacactgtga agggccgatt caccatctcc agagataatt ccaagaacat tgtgtacctg       240
caaatgaaca gtctgagggc tgaggacacg gccgtgtatt actgtgtaag gaggggctac       300
ggaacttcgt actggggcca agggaccctg gtcaccgtct cctcaggtgg tggtggttct       360
ggcggcggcg gctccggtgg tggtggttct gacatcgtga tgacccaaac tccactctcc       420
ctgtctgtca ctcctggaga accggcctcc atctcttgca gatctagtca gagcattgtt       480
catagtattg gagacaccta tttagaatgg tacctgcaga aaccaggcca gtctccacag       540
ctcctgatct acaaagtttc caaccgattt tctggggtcc cagacaggtt cagtggcagt       600
ggatcaggga cagatttcac actcaagatc agcagagtgg aggctgagga tgtgggagtt       660
tattactgct ttcaaggttc acatttcccg tacacgttcg gacaggggac caagctggaa       720
ataaaa                                                                  726

<210> SEQ ID NO 68
<211> LENGTH: 242
<212> TYPE: PRT
<213> ORGANISM: artificial
<220> FEATURE:
<223> OTHER INFORMATION: VH-VL of humM2e-hBiTE-8

<400> SEQUENCE: 68

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
         35                  40                  45

Ala Ser Met Ser Ser Gly Gly Ser Leu Tyr Tyr Pro Asp Thr Val Lys
     50                  55                  60

Gly Arg Phe Thr Ile Ser Arg Asp Asn Ser Lys Asn Ile Val Tyr Leu
 65                  70                  75                  80

Gln Met Asn Ser Leu Arg Ala Glu Asp Thr Ala Val Tyr Tyr Cys Val
                 85                  90                  95

Arg Gly Gly Tyr Gly Thr Ser Tyr Trp Gly Gln Gly Thr Leu Val Thr
             100                 105                 110

Val Ser Ser Gly Gly Gly Gly Ser Gly Gly Gly Gly Ser Gly Gly Gly
         115                 120                 125

Gly Ser Asp Ile Val Met Thr Gln Thr Pro Leu Ser Leu Ser Val Thr
     130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys

<210> SEQ ID NO 69
<211> LENGTH: 1509
<212> TYPE: DNA
<213> ORGANISM: artificial
<220> FEATURE:
<223> OTHER INFORMATION: VH-VL of humM2e-hBiTE-8 x anti-CD3

<400> SEQUENCE: 69
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga aggccgatt caccatctcc agagataatt ccaagaacat tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga aaccaggcca gtctccacag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacagggcac caagctggaa     720
ataaaatccg gaggtggtgg atccgaggtg cagctggtcg agtctggagg aggattggtg     780

```
cagcctggag ggtcattgaa actctcatgt gcagcctctg gattcacctt caataagtac    840
gccatgaact gggtccgcca ggctccagga aagggtttgg aatgggttgc tcgcataaga    900
agtaaatata ataattatgc aacatattat gccgattcag tgaaagacag gttcaccatc    960
tccagagatg attcaaaaaa cactgcctat ctacaaatga caacttgaa gactgaggac    1020 actgccgtgt actactgtgt gagacatggg aacttcggta atagctacat atcctactgg   1080
gcttactggg gccaagggac tctggtcacc gtctcctcag gtggtggtgg ttctggcggc   1140
ggcggctccg gtggtggtgg ttctcagact gttgtgactc aggaaccttc actcaccgta    1200
tcacctggtg aacagtcac actcacttgt ggctcctcga ctggggctgt acatctggc    1260 aactacccaa actgggtcca acaaaaacca ggtcaggcac cccgtggtct aataggtggg   1320
actaagttcc tcgcccccgg tactcctgcc agattctcag gctccctgct tgaggcaag   1380 gctgccctca ccctctcagg ggtacagcca gaggatgagg cagaatatta ctgtgttcta   1440
tggtacagca accgctgggt gttcggtgga ggaaccaaac tgactgtcct acatcatcac   1500
catcatcat                                                           1509
```

<210> SEQ ID NO 70
<211> LENGTH: 503
<212> TYPE: PRT
<213> ORGANISM: artificial
<220> FEATURE:
<223> OTHER INFORMATION: VH-VL of humM2e-hBiTE-8 x anti-CD3

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220
```

```
Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
                260                 265                 270

Ser Gly Phe Thr Phe Asn Lys Tyr Ala Met Asn Trp Val Arg Gln Ala
            275                 280                 285

Pro Gly Lys Gly Leu Glu Trp Val Ala Arg Ile Arg Ser Lys Tyr Asn
        290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
                340                 345                 350

Gly Asn Ser Tyr Ile Ser Tyr Trp Ala Tyr Trp Gly Gln Gly Thr Leu
            355                 360                 365

Val Thr Val Ser Ser Gly Gly Gly Gly Ser Gly Gly Gly Gly Ser Gly
370                 375                 380

Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
                420                 425                 430

Ala Pro Arg Gly Leu Ile Gly Gly Thr Lys Phe Leu Ala Pro Gly Thr
            435                 440                 445

Pro Ala Arg Phe Ser Gly Ser Leu Leu Gly Gly Lys Ala Ala Leu Thr
        450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500

<210> SEQ ID NO 71
<211> LENGTH: 345
<212> TYPE: DNA
<213> ORGANISM: artificial
<220> FEATURE:
<223> OTHER INFORMATION: VH of humM2e-hBiTE-9

<400> SEQUENCE: 71
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga aggccgatt caccatctcc agagataatt ccaagaacat tgtgtacctg     240
caaatgaaca gtctgagggc tgaggacacg gccgtgtatt actgtgtaag aggaggctac    300
ggaacttcgt actggggcca aggaccctg gtcaccgtct cctca                     345

<210> SEQ ID NO 72
<211> LENGTH: 115
```

```
<212> TYPE: PRT
<213> ORGANISM: artificial
<220> FEATURE:
<223> OTHER INFORMATION: VH of humM2e-hBiTE-9

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser
        115

<210> SEQ ID NO 73
<211> LENGTH: 336
<212> TYPE: DNA
<213> ORGANISM: artificial
<220> FEATURE:
<223> OTHER INFORMATION: VL of humM2e-hBiTE-9

<400> SEQUENCE: 73
gacatcgtga tgacccaaac tccactctcc ctgtctgtca ctcctggaga accggcctcc    60
atctcttgca gatctagtca gagcattgtt catagtattg agacacccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tgtgggagtt tattactgct ttcaaggttc acatttcccg   300
tacacgttcg gacaggggac caagctggaa ataaaa                             336

<210> SEQ ID NO 74
<211> LENGTH: 112
<212> TYPE: PRT
<213> ORGANISM: artificial
<220> FEATURE:
<223> OTHER INFORMATION: VL of humM2e-hBiTE-9

<400> SEQUENCE: 74

Asp Ile Val Met Thr Gln Thr Pro Leu Ser Leu Ser Val Thr Pro Gly
1               5                   10                  15

Glu Pro Ala Ser Ile Ser Cys Arg Ser Ser Gln Ser Ile Val His Ser
            20                  25                  30

Ile Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

85                  90                  95
Ser His Phe Pro Tyr Thr Phe Gly Gln Gly Thr Lys Leu Glu Ile Lys
                  100                 105                 110

<210> SEQ ID NO 75
<211> LENGTH: 726
<212> TYPE: DNA
<213> ORGANISM: artificial
<220> FEATURE:
<223> OTHER INFORMATION: VH-VL of humM2e-hBiTE-9

<400> SEQUENCE: 75
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctgaatg gtcgcatcc atgagtagtg gtggtagtct ttattatcca     180
gacactgtga agggccgatt caccatctcc agagataatt ccaagaacat tgtgtacctg     240
caaatgaaca gtctgagggc tgaggacacg gccgtgtatt actgtgtaag gaggggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg agacaccta tttagaatgg tacctgcaga aaccaggcca gtctccaaag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacaggggac caagctggaa     720
ataaaa                                                                 726

<210> SEQ ID NO 76
<211> LENGTH: 242
<212> TYPE: PRT
<213> ORGANISM: artificial
<220> FEATURE:
<223> OTHER INFORMATION: VH-VL of humM2e-hBiTE-9

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val

```
                145                 150                 155                 160
His Ser Ile Gly Asp Thr Tyr Leu Glu Trp Tyr Leu Gln Lys Pro Gly
                    165                 170                 175

Gln Ser Pro Lys Leu Leu Ile Tyr Lys Val Ser Asn Arg Phe Ser Gly
                180                 185                 190

Val Pro Asp Arg Phe Ser Gly Ser Gly Ser Gly Thr Asp Phe Thr Leu
            195                 200                 205

Lys Ile Ser Arg Val Glu Ala Glu Asp Val Gly Val Tyr Tyr Cys Phe
        210                 215                 220

Gln Gly Ser His Phe Pro Tyr Thr Phe Gly Gln Gly Thr Lys Leu Glu
225                 230                 235                 240

Ile Lys

<210> SEQ ID NO 77
<211> LENGTH: 1509
<212> TYPE: DNA
<213> ORGANISM: artificial
<220> FEATURE:
<223> OTHER INFORMATION: VH-VL of humM2e-hBiTE-9 x anti-CD3

<400> SEQUENCE: 77
gaggtgcagc tggtcgagtc tgggggaggc ttagtgcagc ctggagggtc cctgagactc      60
tcctgtgcag cctctggatt cactgtgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagataatt ccaagaacat tgtgtacctg     240
caaatgaaca gtctgagggc tgaggacacg gccgtgtatt actgtgtaag aggaggctac     300
ggaacttcgt actggggcca agggaccctg gtcaccgtct cctcaggtgg tggtggttct     360
ggcggcggcg gctccggtgg tggtggttct gacatcgtga tgacccaaac tccactctcc     420
ctgtctgtca ctcctggaga accggcctcc atctcttgca gatctagtca gagcattgtt     480
catagtattg gagacaccta tttagaatgg tacctgcaga aaccaggcca gtctccaaag     540
ctcctgatct acaaagtttc caaccgattt tctggggtcc cagacaggtt cagtggcagt     600
ggatcaggga cagatttcac actcaagatc agcagagtgg aggctgagga tgtgggagtt     660
tattactgct ttcaaggttc acatttcccg tacacgttcg gacagggcac caagctggaa     720
ataaaatccg gaggtggtgg atccgaggtg cagctggtcg agtctggagg aggattggtg     780
cagcctggag ggtcattgaa actctcatgt gcagcctctg gattcaccct taataagtac     840
gccatgaact gggtccgcca ggctccagga aagggtttgg aatgggttgc tcgcataaga     900
agtaaatata ataattatgc aacatattat gccgattcag tgaaagacag gttcaccatc     960
tccagagatg attcaaaaaa cactgcctat ctacaaatga acaacttgaa gactgaggac    1020
actgccgtgt actactgtgt gagacatggg aacttcggta atagctacat atcctactgg    1080
gcttactggg gccaagggac tctggtcacc gtctcctcag gtggtggtgg ttctggcggc    1140
ggcggctccg gtggtggtgg ttctcagact gttgtgactc aggaaccttc actcaccgta    1200
tcacctggtg gaacagtcac actcacttgt ggctcctcga ctggggctgt tacatctggc    1260
aactacccaa actgggtcca acaaaaacca ggtcaggcac ccgtggtctg ataggtggg    1320 actaagttcc tcgccccgg tactcctgcc agattctcag gctccctgct tggaggcaag    1380
gctgccctca ccctctcagg gtacagcca gaggatgagg cagaatatta ctgtgttcta    1440
tggtacagca accgctgggt gttcggtgga ggaaccaaac tgactgtcct acatcatcac    1500
```

-continued catcatcat                                                                1509

<210> SEQ ID NO 78
<211> LENGTH: 503
<212> TYPE: PRT
<213> ORGANISM: artificial
<220> FEATURE:
<223> OTHER INFORMATION: VH-VL of humM2e-hBiTE-9 x anti-CD3

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Asn Ser Lys Asn Ile Val Tyr Leu
65                  70                  75                  80

Gln Met Asn Ser Leu Arg Ala Glu Asp Thr Ala Val Tyr Tyr Cys Val
                85                  90                  95

Arg Gly Gly Tyr Gly Thr Ser Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Thr Pro Leu Ser Leu Ser Val Thr
    130                 135                 140

Pro Gly Glu Pro Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Lys Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Phe
    210                 215                 220

Gln Gly Ser His Phe Pro Tyr Thr Phe Gly Gln Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Met Asn Trp Val Arg Gln Ala
        275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
```

```
            355                 360                 365
Val Thr Val Ser Ser Gly Gly Gly Ser Gly Gly Gly Ser Gly
    370                 375                 380

Gly Gly Gly Ser Gln Thr Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
            435                 440                 445

Pro Ala Arg Phe Ser Gly Ser Leu Leu Gly Gly Lys Ala Ala Leu Thr
        450                 455                 460

Leu Ser Gly Val Gln Pro Glu Asp Glu Ala Glu Tyr Tyr Cys Val Leu
465                 470                 475                 480

Trp Tyr Ser Asn Arg Trp Val Phe Gly Gly Gly Thr Lys Leu Thr Val
                485                 490                 495

Leu His His His His His His
            500
```

<210> SEQ ID NO 79
<211> LENGTH: 345
<212> TYPE: DNA
<213> ORGANISM: artificial
<220> FEATURE:
<223> OTHER INFORMATION: VH of murM2e-hBiTE

<400> SEQUENCE: 79

```
gaggtgcagc tgctcgagtc tggggggaggc tcagtgaagc ctggagggtc cctgaaactc      60
tcctgttcag cctctggatt ctctttgagt acttatgcca tgtcttgggt tcgccagact     120
ccagagaaga ggctggaatg ggtcgcatcc atgagtagtg gtggtagtct ttattatcca     180
gacactgtga agggccgatt caccatctcc agagatactg tcaagaacat tgtgtacctg     240
caaatgagca gtctgaggtc tgaggacacg gccatgtatt actgtgtaag aggaggctac     300
ggaacttcgt actggggcca agggaccacg gtcaccgtct cctca                     345
```

<210> SEQ ID NO 80
<211> LENGTH: 115
<212> TYPE: PRT
<213> ORGANISM: artificial
<220> FEATURE:
<223> OTHER INFORMATION: VH of murM2e-hBiTE

<400> SEQUENCE: 80

```
Glu Val Gln Leu Leu Glu Ser Gly Gly Gly Ser Val Lys Pro Gly Gly
1               5                   10                  15

Ser Leu Lys Leu Ser Cys Ser Ala Ser Gly Phe Ser Leu Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Val Lys Asn Ile Val Tyr Leu
65                  70                  75                  80

Gln Met Ser Ser Leu Arg Ser Glu Asp Thr Ala Met Tyr Tyr Cys Val
                85                  90                  95
```

```
Arg Gly Gly Tyr Gly Thr Ser Tyr Trp Gly Gln Gly Thr Thr Val Thr
                100                 105                 110

Val Ser Ser
        115
```

<210> SEQ ID NO 81
<211> LENGTH: 336
<212> TYPE: DNA
<213> ORGANISM: artificial
<220> FEATURE:
<223> OTHER INFORMATION: VL of murM2e-hBiTE

<400> SEQUENCE: 81

```
gagctcttgt tgacccaaac tccactctcc ctgcctgtca gtcttggaga tcaggcctcc    60
atctcttgca gatctagtca gagcattgtt catagtattg agacaccta tttagaatgg    120
tacctgcaga accaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggaatt tattactgct ttcaaggttc acattttccg    300
tacacgttcg gaggggggac caagctggaa ataaaa                              336
```

<210> SEQ ID NO 82
<211> LENGTH: 112
<212> TYPE: PRT
<213> ORGANISM: artificial
<220> FEATURE:
<223> OTHER INFORMATION: VL of murM2e-hBiTE

<400> SEQUENCE: 82

```
Glu Leu Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Ile Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Phe Pro Tyr Thr Phe Gly Gly Gly Thr Lys Leu Glu Ile Lys
                100                 105                 110
```

<210> SEQ ID NO 83
<211> LENGTH: 726
<212> TYPE: DNA
<213> ORGANISM: artificial
<220> FEATURE:
<223> OTHER INFORMATION: VH-VL of murM2e-hBiTE

<400> SEQUENCE: 83

```
gaggtgcagc tgctcgagtc tgggggaggc tcagtgaagc tggagggtc cctgaaactc    60
tcctgttcag cctctggatt ctctttgagt acttatgcca tgtcttgggt tcgccagact    120
ccagagaaga ggctggaatg ggtcgcatcc atgagtagtg gtggtagtct ttattatcca    180
gacactgtga aggccgatt caccatctcc agagatactg tcaagaacat tgtgtacctg    240
caaatgagca gtctgaggtc tgaggacacg gccatgtatt actgtgtaag aggaggctac    300
```

```
ggaacttcgt actggggcca agggaccacg gtcaccgtct cctcaggtgg tggtggttct    360
ggcggcggcg gctccggtgg tggtggttct gagctcttgt tgacccaaac tccactctcc    420
ctgcctgtca gtcttggaga tcaggcctcc atctcttgca gatctagtca gagcattgtt    480
catagtattg gagacaccta tttagaatgg tacctgcaga aaccaggcca gtctccaaag    540
ctcctgatct acaaagtttc caaccgattt tctggggtcc cagacaggtt cagtggcagt    600
ggatcaggga cagatttcac actcaagatc agcagagtgg aggctgagga tctgggaatt    660
tattactgct ttcaaggttc acattttccg tacacgttcg gaggggggac caagctggaa    720
ataaaa                                                               726

<210> SEQ ID NO 84
<211> LENGTH: 242
<212> TYPE: PRT
<213> ORGANISM: artificial
<220> FEATURE:
<223> OTHER INFORMATION: VH-VL of murM2e-hBiTE

<400> SEQUENCE: 84
```

Glu Val Gln Leu Leu Glu Ser Gly Gly Gly Ser Val Lys Pro Gly Gly
1               5                   10                  15

Ser Leu Lys Leu Ser Cys Ser Ala Ser Gly Phe Ser Leu Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60

Gly Arg Phe Thr Ile Ser Arg Asp Thr Val Lys Asn Ile Val Tyr Leu
65                  70                  75                  80

Gln Met Ser Ser Leu Arg Ser Glu Asp Thr Ala Met Tyr Tyr Cys Val
                85                  90                  95

Arg Gly Gly Tyr Gly Thr Ser Tyr Trp Gly Gln Gly Thr Thr Val Thr
            100                 105                 110

Val Ser Ser Gly Gly Gly Gly Ser Gly Gly Gly Gly Ser Gly Gly Gly
        115                 120                 125

Gly Ser Glu Leu Leu Leu Thr Gln Thr Pro Leu Ser Leu Pro Val Ser
    130                 135                 140

Leu Gly Asp Gln Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Lys Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Leu Gly Ile Tyr Tyr Cys Phe
    210                 215                 220

Gln Gly Ser His Phe Pro Tyr Thr Phe Gly Gly Gly Thr Lys Leu Glu
225                 230                 235                 240

Ile Lys

```
<210> SEQ ID NO 85
<211> LENGTH: 1509
<212> TYPE: DNA
<213> ORGANISM: artificial
```

<220> FEATURE:
<223> OTHER INFORMATION: VH-VL of murM2e-hBiTE x anti-CD3

<400> SEQUENCE: 85

```
gaggtgcagc tgctcgagtc tgggggaggc tcagtgaagc ctggagggtc cctgaaactc      60
tcctgttcag cctctggatt ctctttgagt acttatgcca tgtcttgggt tcgccagact     120
ccagagaaga ggctggaatg ggtcgcatcc atgagtagtg gtggtagtct ttattatcca     180
gacactgtga aggccgatt caccatctcc agagatactg tcaagaacat tgtgtacctg     240
caaatgagca gtctgaggtc tgaggacacg gccatgtatt actgtgtaag aggaggctac     300
ggaacttcgt actggggcca aggaccacg gtcaccgtct cctcaggtgg tggtggttct     360
ggcggcggcg gctccggtgg tggtggttct gagctcttgt tgacccaaac tccactctcc     420
ctgcctgtca gtcttggaga tcaggcctcc atctcttgca gatctagtca gagcattgtt     480
catagtattg gagacaccta tttagaatgg tacctgcaga accaggcca gtctccaaag     540
ctcctgatct acaaagtttc caaccgattt tctggggtcc cagacaggtt cagtggcagt     600
ggatcaggga cagatttcac actcaagatc agcagagtgg aggctgagga tctgggaatt     660
tattactgct ttcaaggttc acattttccg tacacgttcg gaggggggac caagctggaa     720
ataaaatccg gaggtggtgg atccgaggtg cagctggtcg agtctggagg aggattggtg     780
cagcctggag ggtcattgaa actctcatgt gcagcctctg gattcacctt caataagtac     840
gccatgaact gggtccgcca ggctccagga aagggttgg aatgggttgc tcgcataaga     900
agtaaatata ataattatgc aacatattat gccgattcag tgaaagacag gttcaccatc     960
tccagagatg attcaaaaaa cactgcctat ctacaaatga caacttgaa gactgaggac    1020
actgccgtgt actactgtgt gagacatggg aacttcggta atagctacat atcctactgg    1080
gcttactggg gccaagggac tctggtcacc gtctcctcag gtggtggtgg ttctggcggc    1140
ggcggctccg gtggtggtgg ttctcagact gttgtgactc aggaaccttc actcaccgta    1200
tcacctggtg gaacagtcac actcacttgt ggctcctcga ctgggctgt tacatctggc    1260
aactacccaa ctgggtcca acaaaaacca ggtcaggcac cccgtggtct aataggtggg    1320
actaagttcc tcgcccccgg tactcctgcc agattctcag gctccctgct tggaggcaag    1380
gctgccctca ccctctcagg ggtacagcca gaggatgagg cagaatatta ctgtgttcta    1440
tggtacagca accgctgggt gttcggtgga ggaaccaaac tgactgtcct acatcatcac    1500
catcatcat                                                              1509
```

<210> SEQ ID NO 86
<211> LENGTH: 503
<212> TYPE: PRT
<213> ORGANISM: artificial
<220> FEATURE:
<223> OTHER INFORMATION: VH-VL of murM2e-hBiTE x anti-CD3

<400> SEQUENCE: 86

```
Glu Val Gln Leu Leu Glu Ser Gly Gly Gly Ser Val Lys Pro Gly Gly
 1               5                  10                  15

Ser Leu Lys Leu Ser Cys Ser Ala Ser Gly Phe Ser Leu Ser Thr Tyr
            20                  25                  30

Ala Met Ser Trp Val Arg Gln Thr Pro Glu Lys Arg Leu Glu Trp Val
        35                  40                  45

Ala Ser Met Ser Ser Gly Gly Ser Leu Tyr Tyr Pro Asp Thr Val Lys
    50                  55                  60
```

```
Gly Arg Phe Thr Ile Ser Arg Asp Thr Val Lys Asn Ile Val Tyr Leu
 65                  70                  75                  80

Gln Met Ser Ser Leu Arg Ser Glu Asp Thr Ala Met Tyr Tyr Cys Val
                 85                  90                  95

Arg Gly Gly Tyr Gly Thr Ser Tyr Trp Gly Gln Gly Thr Thr Val Thr
            100                 105                 110

Val Ser Ser Gly Gly Gly Gly Ser Gly Gly Gly Gly Ser Gly Gly Gly
        115                 120                 125

Gly Ser Glu Leu Leu Leu Thr Gln Thr Pro Leu Ser Leu Pro Val Ser
    130                 135                 140

Leu Gly Asp Gln Ala Ser Ile Ser Cys Arg Ser Ser Gln Ser Ile Val
145                 150                 155                 160

His Ser Ile Gly Asp Thr Tyr Leu Glu Trp Tyr Leu Gln Lys Pro Gly
                165                 170                 175

Gln Ser Pro Lys Leu Leu Ile Tyr Lys Val Ser Asn Arg Phe Ser Gly
            180                 185                 190

Val Pro Asp Arg Phe Ser Gly Ser Gly Thr Asp Phe Thr Leu
        195                 200                 205

Lys Ile Ser Arg Val Glu Ala Glu Asp Leu Gly Ile Tyr Tyr Cys Phe
    210                 215                 220

Gln Gly Ser His Phe Pro Tyr Thr Phe Gly Gly Gly Thr Lys Leu Glu
225                 230                 235                 240

Ile Lys Ser Gly Gly Gly Gly Ser Glu Val Gln Leu Val Glu Ser Gly
                245                 250                 255

Gly Gly Leu Val Gln Pro Gly Gly Ser Leu Lys Leu Ser Cys Ala Ala
        260                 265                 270

Ser Gly Phe Thr Phe Asn Lys Tyr Ala Met Asn Trp Val Arg Gln Ala
            275                 280                 285

Pro Gly Lys Gly Leu Glu Trp Val Ala Arg Ile Arg Ser Lys Tyr Asn
        290                 295                 300

Asn Tyr Ala Thr Tyr Tyr Ala Asp Ser Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Gly Asn Phe
            340                 345                 350

Gly Asn Ser Tyr Ile Ser Tyr Trp Ala Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Gly Ser Gln Thr Val Val Thr Gln Glu Pro Ser Leu Thr Val
385                 390                 395                 400

Ser Pro Gly Gly Thr Val Thr Leu Thr Cys Gly Ser Ser Thr Gly Ala
                405                 410                 415

Val Thr Ser Gly Asn Tyr Pro Asn Trp Val Gln Gln Lys Pro Gly Gln
            420                 425                 430

Ala Pro Arg Gly Leu Ile Gly Gly Thr Lys Phe Leu Ala Pro Gly Thr
        435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Val Leu
465                 470                 475                 480
```

```
              Trp Tyr Ser Asn Arg Trp Val Phe Gly Gly Gly Thr Lys Leu Thr Val
                              485                 490                 495

Leu His His His His His
                      500

<210> SEQ ID NO 87
<211> LENGTH: 720
<212> TYPE: DNA
<213> ORGANISM: artificial
<220> FEATURE:
<223> OTHER INFORMATION: anti-murine CD3 binding moiety

<400> SEQUENCE: 87
gaggtgaagc tggtcgagtc tgggggcggt ttagtgaagc ctggcgggtc cctgaaactc        60
tcctgtgcag cctcaggatt cactttcagt acctttccaa tggcctgggt ccgccagtct       120
ccagcgaagc gtctggagtg ggtcgcaacc cttagtccta gtggtgatag cacttactat       180
cgagattccg tgaagggccg attcactatc tccagagata cgcaaaaaa cacccctatac      240 ctccagatga gcagtctgaa gtctgaggac acggccactt attactgcac aagagtcgga       300
tttaccacct tctatttga tttctggggc caaggaacca cggtcaccgt ctcctcaggt        360
ggtggtggtt ctggcggcgg cggctccggt ggtggtggtt ctgacatcca gatgacccag       420
actccttcat tcctgtctgc atctgtggga gacagagtaa ctatcaactg caaagcaagt       480
cagaatatta caagtacttt ggactggtat cagcaaaagc ctgatgggac tgtcaaactc       540
ctgatatata atataaacaa tttgcattca ggagtcccat caaggttcag tggcagtgga       600
tctggtactg atttctcact taccatcagc aacctggagc ctgaagatgt tgccacatat       660
tactgccttc aacatcgcac tgggtggacg ttcggtggag gcaccaagct ggaaatcaaa       720

<210> SEQ ID NO 88
<211> LENGTH: 240
<212> TYPE: PRT
<213> ORGANISM: artificial
<220> FEATURE:
<223> OTHER INFORMATION: anti-murine CD3 binding moiety

<400> SEQUENCE: 88

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Thr Phe
                20                  25                  30

Pro Met Ala Trp Val Arg Gln Ser Pro Ala Lys Arg Leu Glu Trp Val
            35                  40                  45

Ala Thr Leu Ser Pro Ser Gly Asp Ser Thr Tyr Tyr Arg Asp Ser Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Thr Tyr Tyr Cys
                85                  90                  95

Thr Arg Val Gly Phe Thr Thr Phe Tyr Phe Asp Phe Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Thr Pro Ser Phe
    130                 135                 140

Leu Ser Ala Ser Val Gly Asp Arg Val Thr Ile Asn Cys Lys Ala Ser
145                 150                 155                 160
```

```
                                 -continued

Gln Asn Ile Asn Lys Tyr Leu Asp Trp Tyr Gln Gln Lys Pro Asp Gly
                165                 170                 175

Thr Val Lys Leu Leu Ile Tyr Asn Ile Asn Asn Leu His Ser Gly Val
            180                 185                 190

Pro Ser Arg Phe Ser Gly Ser Gly Ser Gly Thr Asp Phe Ser Leu Thr
            195                 200                 205

Ile Ser Asn Leu Glu Pro Glu Asp Val Ala Thr Tyr Tyr Cys Leu Gln
        210                 215                 220

His Arg Thr Gly Trp Thr Phe Gly Gly Gly Thr Lys Leu Glu Ile Lys
225                 230                 235                 240

<210> SEQ ID NO 89
<211> LENGTH: 97
<212> TYPE: PRT
<213> ORGANISM: artificial
<220> FEATURE:
<223> OTHER INFORMATION: M2 Influenza A / strain Puerto Rico 8/34

<400> SEQUENCE: 89

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 90
<211> LENGTH: 24
<212> TYPE: PRT
<213> ORGANISM: artificial
<220> FEATURE:
<223> OTHER INFORMATION: Influenza M2e consensus

<400> SEQUENCE: 90

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 91
<211> LENGTH: 5
<212> TYPE: PRT
<213> ORGANISM: artificial
<220> FEATURE:
<223> OTHER INFORMATION: peptide linker

<400> SEQUENCE: 91

Gly Gly Gly Gly Ser
1               5
```